United States Patent
Schnall-Levin et al.

(10) Patent No.: US 12,249,402 B2
(45) Date of Patent: *Mar. 11, 2025

(54) SEQUENCING METHODS

(71) Applicant: 10x Genomics, Inc., Pleasanton, CA (US)

(72) Inventors: Michael Schnall-Levin, Palo Alto, CA (US); Mirna Jarosz, Mountain View, CA (US); Serge Saxonov, Oakland, CA (US); Kevin Ness, Pleasanton, CA (US); Benjamin Hindson, Pleasanton, CA (US)

(73) Assignee: 10X GENOMICS, INC., Pleasanton, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/198,763

(22) Filed: May 17, 2023

(65) Prior Publication Data

US 2023/0335220 A1 Oct. 19, 2023

Related U.S. Application Data

(63) Continuation of application No. 16/428,656, filed on May 31, 2019, which is a continuation of application No. 14/470,746, filed on Aug. 27, 2014, now Pat. No. 10,395,758.

(60) Provisional application No. 61/979,973, filed on Apr. 15, 2014, provisional application No. 61/916,566, filed on Dec. 16, 2013, provisional application No. 61/872,597, filed on Aug. 30, 2013.

(51) Int. Cl.
*G16B 30/10* (2019.01)
*G16B 30/00* (2019.01)
*G16B 30/20* (2019.01)

(52) U.S. Cl.
CPC ............. *G16B 30/10* (2019.02); *G16B 30/00* (2019.02); *G16B 30/20* (2019.02)

(58) Field of Classification Search
None
See application file for complete search history.

(56) References Cited

U.S. PATENT DOCUMENTS

| | | | |
|---|---|---|---|
| 4,124,638 A | 11/1978 | Hansen | |
| 5,149,625 A | 9/1992 | Church et al. | |
| 5,185,099 A | 2/1993 | Delpuech et al. | |
| 5,202,231 A | 4/1993 | Drmanac et al. | |
| 5,270,183 A | 12/1993 | Corbett et al. | |
| 5,413,924 A | 5/1995 | Kosak et al. | |
| 5,436,130 A | 7/1995 | Mathies et al. | |
| 5,478,893 A | 12/1995 | Ghosh et al. | |
| 5,512,131 A | 4/1996 | Kumar et al. | |
| 5,587,128 A | 12/1996 | Wilding et al. | |
| 5,605,793 A | 2/1997 | Stemmer et al. | |
| 5,618,711 A | 4/1997 | Gelfand et al. | |
| 5,695,940 A | 12/1997 | Drmanac et al. | |
| 5,736,330 A | 4/1998 | Fulton | |
| 5,756,334 A | 5/1998 | Perler et al. | |
| 5,834,197 A | 11/1998 | Parton | |
| 5,846,719 A | 12/1998 | Brenner et al. | |
| 5,851,769 A | 12/1998 | Gray et al. | |
| 5,856,174 A | 1/1999 | Lipshutz et al. | |
| 5,900,481 A | 5/1999 | Lough et al. | |
| 5,942,609 A | 8/1999 | Hunkapiller et al. | |
| 5,958,703 A | 9/1999 | Dower et al. | |
| 5,994,056 A | 11/1999 | Higuchi | |
| 6,033,880 A | 3/2000 | Haff et al. | |
| 6,046,003 A | 4/2000 | Mandecki | |
| 6,051,377 A | 4/2000 | Mandecki | |
| 6,057,107 A | 5/2000 | Fulton | |
| 6,057,149 A | 5/2000 | Burns et al. | |
| 6,103,537 A | 8/2000 | Ullman et al. | |
| 6,123,798 A | 9/2000 | Gandhi et al. | |
| 6,143,496 A | 11/2000 | Brown et al. | |
| 6,171,850 B1 | 1/2001 | Nagle et al. | |
| 6,172,218 B1 | 1/2001 | Brenner | |
| 6,176,962 B1 | 1/2001 | Soane et al. | |
| 6,297,006 B1 | 10/2001 | Drmanac et al. | |
| 6,297,017 B1 | 10/2001 | Schmidt et al. | |
| 6,306,590 B1 | 10/2001 | Mehta et al. | |
| 6,327,410 B1 | 12/2001 | Walt et al. | |
| 6,355,198 B1 | 3/2002 | Kim et al. | |
| 6,361,950 B1 | 3/2002 | Mandecki | |
| 6,372,813 B1 | 4/2002 | Johnson et al. | |

(Continued)

FOREIGN PATENT DOCUMENTS

| | | |
|---|---|---|
| EP | 0249007 A2 | 12/1987 |
| EP | 0637996 B1 | 7/1997 |

(Continued)

OTHER PUBLICATIONS

Co-pending U.S. Appl. No. 18/152,650, inventor Shastry; Shankar, filed Jan. 10, 2023.
10X Genomics, Inc. CG000153 Rev A. Chromium Single Cell DNA Reagent Kits User Guide. 2018.
10X Genomics, Inc. CG000184 Rev A. Chromium Single Cell 3' Reagent Kits v3 User Guide with Feature Barcoding Technology for CRISPR Screening. 2018.
10X Genomics, Inc. CG000185 Rev B. Chromium Single Cell 3' Reagent Kits User Guide with Feature Barcoding Technology for Cell Surface Protein. 2018.

(Continued)

*Primary Examiner* — Joseph Woitach
(74) *Attorney, Agent, or Firm* — Wilson Sonsini Goodrich & Rosati

(57) ABSTRACT

The invention described herein solves challenges in providing a proficient, rapid and meaningful analysis of sequencing data. Methods and computer program products of the invention allow for a system to receive, analyze, and display sequencing data in real-time. The invention provides solutions to several difficulties encountered in assembling short sequencing-reads, and by doing so the invention improves the worth and significance of sequencing data.

20 Claims, 21 Drawing Sheets

(56) References Cited

U.S. PATENT DOCUMENTS

| | | |
|---|---|---|
| 6,379,929 B1 | 4/2002 | Burns et al. |
| 6,406,848 B1 | 6/2002 | Bridgham et al. |
| 6,409,832 B2 | 6/2002 | Weigl et al. |
| 6,432,360 B1 | 8/2002 | Church |
| 6,485,944 B1 | 11/2002 | Church et al. |
| 6,492,118 B1 | 12/2002 | Abrams et al. |
| 6,511,803 B1 | 1/2003 | Church et al. |
| 6,524,456 B1 | 2/2003 | Ramsey et al. |
| 6,586,176 B1 | 7/2003 | Trnovsky et al. |
| 6,632,606 B1 | 10/2003 | Ullman et al. |
| 6,632,655 B1 | 10/2003 | Mehta et al. |
| 6,670,133 B2 | 12/2003 | Knapp et al. |
| 6,767,731 B2 | 7/2004 | Hannah |
| 6,800,298 B1 | 10/2004 | Burdick et al. |
| 6,806,052 B2 | 10/2004 | Bridgham et al. |
| 6,806,058 B2 | 10/2004 | Jesperson et al. |
| 6,859,570 B2 | 2/2005 | Walt et al. |
| 6,913,935 B1 | 7/2005 | Thomas |
| 6,915,679 B2 | 7/2005 | Chien et al. |
| 6,929,859 B2 | 8/2005 | Chandler et al. |
| 6,969,488 B2 | 11/2005 | Bridgham et al. |
| 6,974,669 B2 | 12/2005 | Mirkin et al. |
| 7,041,481 B2 | 5/2006 | Anderson et al. |
| 7,115,400 B1 | 10/2006 | Adessi et al. |
| 7,129,091 B2 | 10/2006 | Ismagilov et al. |
| 7,268,167 B2 | 9/2007 | Higuchi et al. |
| 7,282,370 B2 | 10/2007 | Bridgham et al. |
| 7,294,503 B2 | 11/2007 | Quake et al. |
| 7,323,305 B2 | 1/2008 | Leamon et al. |
| 7,425,431 B2 | 9/2008 | Church et al. |
| 7,536,928 B2 | 5/2009 | Kazuno |
| 7,544,473 B2 | 6/2009 | Brenner |
| 7,604,938 B2 | 10/2009 | Takahashi et al. |
| 7,622,076 B2 | 11/2009 | Davies et al. |
| 7,622,280 B2 | 11/2009 | Holliger et al. |
| 7,638,276 B2 | 12/2009 | Griffiths et al. |
| 7,645,596 B2 | 1/2010 | Williams et al. |
| 7,666,664 B2 | 2/2010 | Sarofim et al. |
| 7,708,949 B2 | 5/2010 | Stone et al. |
| 7,709,197 B2 | 5/2010 | Drmanac |
| 7,745,178 B2 | 6/2010 | Dong |
| 7,772,287 B2 | 8/2010 | Higuchi et al. |
| 7,776,927 B2 | 8/2010 | Chu et al. |
| RE41,780 E | 9/2010 | Anderson et al. |
| 7,799,553 B2 | 9/2010 | Mathies et al. |
| 7,842,457 B2 | 11/2010 | Berka et al. |
| 7,901,891 B2 | 3/2011 | Drmanac |
| 7,910,354 B2 | 3/2011 | Drmanac et al. |
| 7,927,797 B2 | 4/2011 | Nobile et al. |
| 7,960,104 B2 | 6/2011 | Drmanac et al. |
| 7,968,287 B2 | 6/2011 | Griffiths et al. |
| 7,972,778 B2 | 7/2011 | Brown et al. |
| 8,003,312 B2 | 8/2011 | Krutzik et al. |
| 8,053,192 B2 | 11/2011 | Bignell et al. |
| 8,067,159 B2 | 11/2011 | Brown et al. |
| 8,133,719 B2 | 3/2012 | Drmanac et al. |
| 8,168,385 B2 | 5/2012 | Brenner |
| 8,252,539 B2 | 8/2012 | Quake et al. |
| 8,268,564 B2 | 9/2012 | Roth et al. |
| 8,273,573 B2 | 9/2012 | Ismagilov et al. |
| 8,278,071 B2 | 10/2012 | Brown et al. |
| 8,298,767 B2 | 10/2012 | Brenner et al. |
| 8,304,193 B2 | 11/2012 | Ismagilov et al. |
| 8,318,433 B2 | 11/2012 | Brenner |
| 8,329,407 B2 | 12/2012 | Ismagilov et al. |
| 8,337,778 B2 | 12/2012 | Stone et al. |
| 8,592,150 B2 | 11/2013 | Drmanac et al. |
| 8,603,749 B2 | 12/2013 | Gillevet |
| 8,658,430 B2 | 2/2014 | Miller et al. |
| 8,748,094 B2 | 6/2014 | Weitz et al. |
| 8,748,102 B2 | 6/2014 | Berka et al. |
| 8,765,380 B2 | 7/2014 | Berka et al. |
| 8,822,148 B2 | 9/2014 | Ismagliov et al. |
| 8,835,358 B2 | 9/2014 | Fodor et al. |
| 8,871,444 B2 | 10/2014 | Griffiths et al. |
| 8,889,083 B2 | 11/2014 | Ismagilov et al. |
| 8,975,302 B2 | 3/2015 | Light et al. |
| 9,012,370 B2 | 4/2015 | Hong |
| 9,012,390 B2 | 4/2015 | Holtze et al. |
| 9,017,948 B2 | 4/2015 | Agresti et al. |
| 9,029,083 B2 | 5/2015 | Griffiths et al. |
| 9,029,085 B2 | 5/2015 | Agresti et al. |
| 9,085,798 B2 | 7/2015 | Chee |
| 9,089,844 B2 | 7/2015 | Hiddessen et al. |
| 9,126,160 B2 | 9/2015 | Ness et al. |
| 9,156,010 B2 | 10/2015 | Colston et al. |
| 9,194,861 B2 | 11/2015 | Hindson et al. |
| 9,216,392 B2 | 12/2015 | Hindson et al. |
| 9,238,206 B2 | 1/2016 | Rotem et al. |
| 9,266,104 B2 | 2/2016 | Link |
| 9,290,808 B2 | 3/2016 | Fodor et al. |
| 9,328,382 B2 | 5/2016 | Drmanac et al. |
| 9,347,059 B2 | 5/2016 | Saxonov |
| 9,371,598 B2 | 6/2016 | Chee |
| 9,388,465 B2 | 7/2016 | Hindson et al. |
| 9,410,201 B2 | 8/2016 | Hindson et al. |
| 9,417,190 B2 | 8/2016 | Hindson et al. |
| 9,486,757 B2 | 11/2016 | Romanowsky et al. |
| 9,498,761 B2 | 11/2016 | Holtze et al. |
| 9,500,664 B2 | 11/2016 | Ness et al. |
| 9,567,631 B2 | 2/2017 | Hindson et al. |
| 9,593,365 B2 | 3/2017 | Frisen et al. |
| 9,623,384 B2 | 4/2017 | Hindson et al. |
| 9,637,799 B2 | 5/2017 | Fan et al. |
| 9,644,204 B2 | 5/2017 | Hindson et al. |
| 9,689,024 B2 | 6/2017 | Hindson et al. |
| 9,694,361 B2 | 7/2017 | Bharadwaj et al. |
| 9,695,468 B2 | 7/2017 | Hindson et al. |
| 9,701,998 B2 | 7/2017 | Hindson et al. |
| 9,764,322 B2 | 9/2017 | Hiddessen et al. |
| 9,824,068 B2 | 11/2017 | Wong |
| 9,868,979 B2 | 1/2018 | Chee et al. |
| 9,879,313 B2 | 1/2018 | Chee et al. |
| 9,946,577 B1 | 4/2018 | Stafford et al. |
| 9,951,386 B2 | 4/2018 | Hindson et al. |
| 9,957,558 B2 | 5/2018 | Leamon et al. |
| 9,975,122 B2 | 5/2018 | Masquelier et al. |
| 10,011,872 B1 | 7/2018 | Belgrader et al. |
| 10,017,759 B2 | 7/2018 | Kaper et al. |
| 10,030,261 B2 | 7/2018 | Frisen et al. |
| 10,059,989 B2 | 8/2018 | Giresi et al. |
| 10,119,167 B2 | 11/2018 | Srinivasan et al. |
| 10,221,436 B2 | 3/2019 | Hardenbol et al. |
| 10,221,442 B2 | 3/2019 | Hindson et al. |
| 10,253,364 B2 | 4/2019 | Hindson et al. |
| 10,273,541 B2 | 4/2019 | Hindson et al. |
| 10,323,279 B2 | 6/2019 | Hindson et al. |
| 10,347,365 B2 | 7/2019 | Wong et al. |
| 10,357,771 B2 | 7/2019 | Bharadwaj et al. |
| 10,395,758 B2 | 8/2019 | Schnall-Levin |
| 10,400,280 B2 | 9/2019 | Hindson et al. |
| 10,428,326 B2 | 10/2019 | Belhocine et al. |
| 10,450,607 B2 | 10/2019 | Hindson et al. |
| 10,533,221 B2 | 1/2020 | Hindson et al. |
| 10,544,413 B2 | 1/2020 | Bharadwaj et al. |
| 10,549,279 B2 | 2/2020 | Bharadwaj et al. |
| 10,557,158 B2 | 2/2020 | Hardenbol et al. |
| 10,590,244 B2 | 3/2020 | Delaney et al. |
| 10,745,742 B2 | 8/2020 | Bent et al. |
| 10,752,949 B2 | 8/2020 | Hindson et al. |
| 10,774,374 B2 | 9/2020 | Frisen et al. |
| 10,815,525 B2 | 10/2020 | Lucero et al. |
| 10,829,815 B2 | 11/2020 | Bharadwaj et al. |
| 10,837,047 B2 | 11/2020 | Delaney et al. |
| 10,874,997 B2 | 12/2020 | Weitz et al. |
| 10,995,333 B2 | 5/2021 | Pfeiffer |
| 11,371,094 B2 | 6/2022 | Ryvkin et al. |
| 11,459,607 B1 | 10/2022 | Terry et al. |
| 11,467,153 B2 | 10/2022 | Belhocine et al. |
| 11,655,499 B1 | 5/2023 | Pfeiffer |
| 11,845,983 B1 | 12/2023 | Belhocine et al. |
| 11,851,683 B1 | 12/2023 | Maheshwari et al. |
| 11,851,700 B1 | 12/2023 | Bava et al. |
| 11,920,183 B2 | 3/2024 | Bharadwaj et al. |

(56) References Cited

U.S. PATENT DOCUMENTS

| | | |
|---|---|---|
| 11,952,626 B2 | 4/2024 | Pfeiffer et al. |
| 2001/0020588 A1 | 9/2001 | Adourian et al. |
| 2001/0044109 A1 | 11/2001 | Mandecki |
| 2002/0005354 A1 | 1/2002 | Spence et al. |
| 2002/0034737 A1 | 3/2002 | Drmanac |
| 2002/0051971 A1 | 5/2002 | Stuelpnagel et al. |
| 2002/0051992 A1 | 5/2002 | Bridgham et al. |
| 2002/0058332 A1 | 5/2002 | Quake et al. |
| 2002/0089100 A1 | 7/2002 | Kawasaki |
| 2002/0092767 A1 | 7/2002 | Bjornson et al. |
| 2002/0119455 A1 | 8/2002 | Chan |
| 2002/0127736 A1 | 9/2002 | Chou et al. |
| 2002/0179849 A1 | 12/2002 | Maher et al. |
| 2003/0008285 A1 | 1/2003 | Fischer |
| 2003/0008323 A1 | 1/2003 | Ravkin et al. |
| 2003/0027221 A1 | 2/2003 | Scott et al. |
| 2003/0028981 A1 | 2/2003 | Chandler et al. |
| 2003/0036206 A1 | 2/2003 | Chien et al. |
| 2003/0044777 A1 | 3/2003 | Beattie |
| 2003/0044836 A1 | 3/2003 | Levine et al. |
| 2003/0075446 A1 | 4/2003 | Culbertson et al. |
| 2003/0104466 A1 | 6/2003 | Knapp et al. |
| 2003/0108897 A1 | 6/2003 | Drmanac |
| 2003/0124509 A1 | 7/2003 | Kenis et al. |
| 2003/0149307 A1 | 8/2003 | Hai et al. |
| 2003/0170698 A1 | 9/2003 | Gascoyne et al. |
| 2003/0182068 A1 | 9/2003 | Battersby et al. |
| 2003/0207260 A1 | 11/2003 | Trnovsky et al. |
| 2003/0215862 A1 | 11/2003 | Parce et al. |
| 2004/0019005 A1 | 1/2004 | Van Ness et al. |
| 2004/0063138 A1 | 4/2004 | McGinnis et al. |
| 2004/0067493 A1 | 4/2004 | Matsuzaki et al. |
| 2004/0068019 A1 | 4/2004 | Higuchi et al. |
| 2004/0132122 A1 | 7/2004 | Banerjee et al. |
| 2004/0258701 A1 | 12/2004 | Dominowski et al. |
| 2005/0019839 A1 | 1/2005 | Jespersen et al. |
| 2005/0042625 A1 | 2/2005 | Schmidt et al. |
| 2005/0130188 A1 | 6/2005 | Walt et al. |
| 2005/0181379 A1 | 8/2005 | Su et al. |
| 2005/0202429 A1 | 9/2005 | Trau et al. |
| 2005/0202489 A1 | 9/2005 | Cho et al. |
| 2005/0221339 A1 | 10/2005 | Griffiths et al. |
| 2005/0244850 A1 | 11/2005 | Huang et al. |
| 2005/0250147 A1 | 11/2005 | Macevicz |
| 2005/0266582 A1 | 12/2005 | Modlin et al. |
| 2005/0287572 A1 | 12/2005 | Mathies et al. |
| 2006/0020371 A1 | 1/2006 | Ham et al. |
| 2006/0073487 A1 | 4/2006 | Oliver et al. |
| 2006/0153924 A1 | 7/2006 | Griffiths et al. |
| 2006/0163385 A1 | 7/2006 | Link et al. |
| 2006/0177832 A1 | 8/2006 | Brenner |
| 2006/0199193 A1 | 9/2006 | Koo et al. |
| 2006/0240506 A1 | 10/2006 | Kushmaro et al. |
| 2006/0263888 A1 | 11/2006 | Fritz et al. |
| 2006/0275782 A1 | 12/2006 | Gunderson et al. |
| 2006/0292583 A1 | 12/2006 | Schneider et al. |
| 2007/0003442 A1 | 1/2007 | Link et al. |
| 2007/0020617 A1 | 1/2007 | Trnovsky et al. |
| 2007/0020640 A1 | 1/2007 | McCloskey et al. |
| 2007/0042419 A1 | 2/2007 | Barany et al. |
| 2007/0054119 A1 | 3/2007 | Garstecki et al. |
| 2007/0077572 A1 | 4/2007 | Tawfik et al. |
| 2007/0092914 A1 | 4/2007 | Griffiths et al. |
| 2007/0099208 A1 | 5/2007 | Drmanac et al. |
| 2007/0111241 A1 | 5/2007 | Cereb et al. |
| 2007/0154903 A1 | 7/2007 | Marla et al. |
| 2007/0172873 A1 | 7/2007 | Brenner et al. |
| 2007/0190543 A1 | 8/2007 | Livak |
| 2007/0195127 A1 | 8/2007 | Ahn et al. |
| 2007/0196397 A1 | 8/2007 | Torii et al. |
| 2007/0207060 A1 | 9/2007 | Zou et al. |
| 2007/0228588 A1 | 10/2007 | Noritomi et al. |
| 2007/0264320 A1 | 11/2007 | Lee et al. |
| 2008/0003142 A1 | 1/2008 | Link et al. |
| 2008/0004436 A1 | 1/2008 | Tawfik et al. |
| 2008/0014589 A1 | 1/2008 | Link et al. |
| 2008/0056948 A1 | 3/2008 | Dale et al. |
| 2008/0166720 A1 | 7/2008 | Hsieh et al. |
| 2008/0213766 A1 | 9/2008 | Brown et al. |
| 2008/0241820 A1 | 10/2008 | Krutzik et al. |
| 2008/0242560 A1 | 10/2008 | Gunderson et al. |
| 2008/0268431 A1 | 10/2008 | Choy et al. |
| 2009/0005252 A1 | 1/2009 | Drmanac et al. |
| 2009/0011943 A1 | 1/2009 | Drmanac et al. |
| 2009/0012187 A1 | 1/2009 | Chu et al. |
| 2009/0025277 A1 | 1/2009 | Takanashi |
| 2009/0035770 A1 | 2/2009 | Mathies et al. |
| 2009/0047713 A1 | 2/2009 | Handique |
| 2009/0048124 A1 | 2/2009 | Leamon et al. |
| 2009/0053169 A1 | 2/2009 | Castillo et al. |
| 2009/0068170 A1 | 3/2009 | Weitz et al. |
| 2009/0099041 A1 | 4/2009 | Church et al. |
| 2009/0118488 A1 | 5/2009 | Drmanac et al. |
| 2009/0131543 A1 | 5/2009 | Weitz et al. |
| 2009/0137404 A1 | 5/2009 | Drmanac et al. |
| 2009/0137414 A1 | 5/2009 | Drmanac et al. |
| 2009/0143244 A1 | 6/2009 | Bridgham et al. |
| 2009/0148961 A1 | 6/2009 | Luchini et al. |
| 2009/0155563 A1 | 6/2009 | Petsev et al. |
| 2009/0155781 A1 | 6/2009 | Drmanac et al. |
| 2009/0197772 A1 | 8/2009 | Griffiths et al. |
| 2009/0202984 A1 | 8/2009 | Cantor |
| 2009/0203531 A1 | 8/2009 | Kurn |
| 2009/0235990 A1 | 9/2009 | Beer |
| 2009/0264299 A1 | 10/2009 | Drmanac et al. |
| 2009/0269248 A1 | 10/2009 | Falb et al. |
| 2009/0286687 A1 | 11/2009 | Dressman et al. |
| 2010/0021973 A1 | 1/2010 | Makarov et al. |
| 2010/0021984 A1 | 1/2010 | Edd et al. |
| 2010/0022414 A1 | 1/2010 | Link et al. |
| 2010/0035254 A1 | 2/2010 | Williams |
| 2010/0069263 A1 | 3/2010 | Shendure et al. |
| 2010/0086914 A1 | 4/2010 | Bentley et al. |
| 2010/0105866 A1 | 4/2010 | Fraden et al. |
| 2010/0130369 A1 | 5/2010 | Shenderov et al. |
| 2010/0137163 A1 | 6/2010 | Link et al. |
| 2010/0184928 A1 | 7/2010 | Kumacheva |
| 2010/0210479 A1 | 8/2010 | Griffiths et al. |
| 2010/0216153 A1 | 8/2010 | Lapidus et al. |
| 2010/0248991 A1 | 9/2010 | Roesler et al. |
| 2010/0304982 A1 | 12/2010 | Hinz et al. |
| 2011/0033854 A1 | 2/2011 | Drmanac et al. |
| 2011/0071053 A1 | 3/2011 | Drmanac et al. |
| 2011/0091366 A1 | 4/2011 | Kendall et al. |
| 2011/0092376 A1 | 4/2011 | Colston, Jr. et al. |
| 2011/0160078 A1 | 6/2011 | Fodor et al. |
| 2011/0195496 A1 | 8/2011 | Muraguchi et al. |
| 2011/0217736 A1 | 9/2011 | Hindson |
| 2011/0218123 A1 | 9/2011 | Weitz et al. |
| 2011/0257889 A1 | 10/2011 | Klammer et al. |
| 2011/0263457 A1 | 10/2011 | Krutzik et al. |
| 2011/0267457 A1 | 11/2011 | Weitz et al. |
| 2011/0281738 A1 | 11/2011 | Drmanac et al. |
| 2011/0305761 A1 | 12/2011 | Shum et al. |
| 2011/0319281 A1 | 12/2011 | Drmanac |
| 2012/0000777 A1 | 1/2012 | Garrell et al. |
| 2012/0010098 A1 | 1/2012 | Griffiths et al. |
| 2012/0010107 A1 | 1/2012 | Griffiths et al. |
| 2012/0015382 A1 | 1/2012 | Weitz et al. |
| 2012/0015822 A1 | 1/2012 | Weitz et al. |
| 2012/0041727 A1 | 2/2012 | Mishra et al. |
| 2012/0071331 A1 | 3/2012 | Casbon et al. |
| 2012/0121481 A1 | 5/2012 | Romanowsky et al. |
| 2012/0132288 A1 | 5/2012 | Weitz et al. |
| 2012/0135893 A1 | 5/2012 | Drmanac et al. |
| 2012/0172259 A1 | 7/2012 | Rigatti et al. |
| 2012/0184449 A1 | 7/2012 | Hixson et al. |
| 2012/0190032 A1 | 7/2012 | Ness et al. |
| 2012/0196288 A1 | 8/2012 | Beer |
| 2012/0211084 A1 | 8/2012 | Weitz et al. |
| 2012/0219947 A1 | 8/2012 | Yurkovetsky et al. |
| 2012/0220494 A1 | 8/2012 | Samuels et al. |
| 2012/0220497 A1 | 8/2012 | Jacobson et al. |
| 2012/0222748 A1 | 9/2012 | Weitz et al. |

(56) References Cited

U.S. PATENT DOCUMENTS

| | | |
|---|---|---|
| 2012/0230338 A1 | 9/2012 | Ganeshalingam et al. |
| 2012/0309002 A1 | 12/2012 | Link |
| 2013/0028812 A1 | 1/2013 | Prieto et al. |
| 2013/0079231 A1 | 3/2013 | Pushkarev et al. |
| 2013/0109575 A1 | 5/2013 | Kleinschmidt et al. |
| 2013/0130919 A1 | 5/2013 | Chen et al. |
| 2013/0157870 A1 | 6/2013 | Pushkarev et al. |
| 2013/0157899 A1 | 6/2013 | Adler, Jr. et al. |
| 2013/0178368 A1 | 7/2013 | Griffiths et al. |
| 2013/0185096 A1 | 7/2013 | Giusti et al. |
| 2013/0189700 A1 | 7/2013 | So et al. |
| 2013/0203605 A1 | 8/2013 | Shendure et al. |
| 2013/0210639 A1 | 8/2013 | Link et al. |
| 2013/0225418 A1 | 8/2013 | Watson |
| 2013/0268206 A1 | 10/2013 | Porreca et al. |
| 2013/0274117 A1 | 10/2013 | Church et al. |
| 2013/0311106 A1 | 11/2013 | White et al. |
| 2013/0317755 A1 | 11/2013 | Mishra et al. |
| 2014/0037514 A1 | 2/2014 | Stone et al. |
| 2014/0057799 A1 | 2/2014 | Johnson et al. |
| 2014/0065234 A1 | 3/2014 | Shum et al. |
| 2014/0155295 A1 | 6/2014 | Hindson et al. |
| 2014/0194323 A1 | 7/2014 | Gillevet et al. |
| 2014/0199731 A1 | 7/2014 | Agresti et al. |
| 2014/0200166 A1 | 7/2014 | Van Rooyen et al. |
| 2014/0214334 A1 | 7/2014 | Plattner et al. |
| 2014/0221239 A1 | 8/2014 | Carman et al. |
| 2014/0227706 A1 | 8/2014 | Kato et al. |
| 2014/0235506 A1 | 8/2014 | Hindson et al. |
| 2014/0272996 A1 | 9/2014 | Bemis |
| 2014/0274740 A1 | 9/2014 | Srinivasan et al. |
| 2014/0287963 A1 | 9/2014 | Hindson et al. |
| 2014/0302503 A1 | 10/2014 | Lowe et al. |
| 2014/0323316 A1 | 10/2014 | Drmanac et al. |
| 2014/0338753 A1 | 11/2014 | Sperling et al. |
| 2014/0378322 A1 | 12/2014 | Hindson et al. |
| 2014/0378345 A1 | 12/2014 | Hindson et al. |
| 2014/0378349 A1 | 12/2014 | Hindson et al. |
| 2015/0005199 A1 | 1/2015 | Hindson et al. |
| 2015/0005200 A1 | 1/2015 | Hindson et al. |
| 2015/0011430 A1 | 1/2015 | Saxonov |
| 2015/0011432 A1 | 1/2015 | Saxonov et al. |
| 2015/0066385 A1 | 3/2015 | Schnall-Levin et al. |
| 2015/0111256 A1 | 4/2015 | Church et al. |
| 2015/0133344 A1 | 5/2015 | Shendure et al. |
| 2015/0218633 A1 | 8/2015 | Hindson et al. |
| 2015/0220532 A1 | 8/2015 | Wong |
| 2015/0224466 A1 | 8/2015 | Hindson et al. |
| 2015/0267191 A1 | 9/2015 | Steelman et al. |
| 2015/0275289 A1 | 10/2015 | Otwinowski et al. |
| 2015/0298091 A1 | 10/2015 | Weitz et al. |
| 2015/0299772 A1 | 10/2015 | Zhang |
| 2015/0361418 A1 | 12/2015 | Reed |
| 2015/0376605 A1 | 12/2015 | Jarosz et al. |
| 2015/0376608 A1 | 12/2015 | Kaper et al. |
| 2015/0376609 A1 | 12/2015 | Hindson et al. |
| 2015/0376700 A1 | 12/2015 | Schnall-Levin et al. |
| 2015/0379196 A1 | 12/2015 | Schnall-Levin et al. |
| 2016/0008778 A1 | 1/2016 | Weitz et al. |
| 2016/0024558 A1 | 1/2016 | Hardenbol et al. |
| 2016/0024572 A1 | 1/2016 | Shishkin et al. |
| 2016/0053253 A1 | 2/2016 | Salathia et al. |
| 2016/0059204 A1 | 3/2016 | Hindson et al. |
| 2016/0060621 A1 | 3/2016 | Agresti et al. |
| 2016/0122753 A1 | 5/2016 | Mikkelsen et al. |
| 2016/0122817 A1 | 5/2016 | Jarosz et al. |
| 2016/0203196 A1 | 7/2016 | Schnall-Levin et al. |
| 2016/0232291 A1 | 8/2016 | Kyriazopoulou-Panagiotopoulou et al. |
| 2016/0244809 A1 | 8/2016 | Belgrader et al. |
| 2016/0281160 A1 | 9/2016 | Jarosz et al. |
| 2016/0289769 A1 | 10/2016 | Schwartz et al. |
| 2016/0304860 A1 | 10/2016 | Hindson et al. |
| 2016/0314242 A1 | 10/2016 | Schnall-Levin et al. |
| 2016/0348093 A1 | 12/2016 | Price et al. |
| 2016/0350478 A1 | 12/2016 | Chin et al. |
| 2017/0016041 A1 | 1/2017 | Greenfield et al. |
| 2017/0128937 A1 | 5/2017 | Hung et al. |
| 2017/0144161 A1 | 5/2017 | Hindson et al. |
| 2017/0145476 A1 | 5/2017 | Ryvkin et al. |
| 2017/0159109 A1 | 6/2017 | Zheng et al. |
| 2017/0235876 A1 | 8/2017 | Jaffe et al. |
| 2017/0260584 A1 | 9/2017 | Zheng et al. |
| 2018/0030515 A1 | 2/2018 | Regev et al. |
| 2018/0080075 A1 | 3/2018 | Brenner et al. |
| 2018/0105808 A1 | 4/2018 | Mikkelsen et al. |
| 2018/0196781 A1 | 7/2018 | Wong |
| 2018/0216162 A1 | 8/2018 | Belhocine et al. |
| 2018/0265928 A1 | 9/2018 | Schnall-Levin et al. |
| 2018/0312822 A1 | 11/2018 | Lee et al. |
| 2018/0312873 A1 | 11/2018 | Zheng |
| 2018/0340169 A1 | 11/2018 | Belhocine et al. |
| 2018/0371545 A1 | 12/2018 | Wong et al. |
| 2019/0060890 A1 | 2/2019 | Bharadwaj et al. |
| 2019/0060904 A1 | 2/2019 | Bharadwaj et al. |
| 2019/0060905 A1 | 2/2019 | Bharadwaj et al. |
| 2019/0064173 A1 | 2/2019 | Bharadwaj et al. |
| 2019/0071656 A1 | 3/2019 | Chang et al. |
| 2019/0085391 A1 | 3/2019 | Hindson et al. |
| 2019/0127731 A1 | 5/2019 | McDermott |
| 2019/0134633 A1 | 5/2019 | Bharadwaj et al. |
| 2019/0136316 A1 | 5/2019 | Hindson et al. |
| 2019/0153532 A1 | 5/2019 | Bharadwaj et al. |
| 2019/0176152 A1 | 6/2019 | Bharadwaj et al. |
| 2019/0177800 A1 | 6/2019 | Boutet et al. |
| 2019/0249226 A1 | 8/2019 | Bent et al. |
| 2019/0323088 A1 | 10/2019 | Boutet et al. |
| 2019/0345636 A1 | 11/2019 | McDermott et al. |
| 2019/0352717 A1 | 11/2019 | Schnall-Levin |
| 2019/0367997 A1 | 12/2019 | Bent et al. |
| 2019/0376118 A1 | 12/2019 | Belhocine et al. |
| 2020/0002763 A1 | 1/2020 | Belgrader et al. |
| 2020/0005902 A1 | 1/2020 | Mellen et al. |
| 2020/0020417 A1 | 1/2020 | Schnall-Levin et al. |
| 2020/0032335 A1 | 1/2020 | Martinez |
| 2020/0033237 A1 | 1/2020 | Hindson et al. |
| 2020/0033366 A1 | 1/2020 | Alvarado Martinez |
| 2020/0056223 A1 | 2/2020 | Bell |
| 2020/0105373 A1 | 4/2020 | Zheng |
| 2020/0263232 A1 | 8/2020 | Bell et al. |
| 2020/0291454 A1 | 9/2020 | Belhocine et al. |
| 2020/0407775 A1 | 12/2020 | Bharadwaj et al. |
| 2021/0190770 A1 | 6/2021 | Delaney et al. |
| 2021/0270703 A1 | 9/2021 | Abousoud |
| 2022/0162671 A1 | 5/2022 | Pfeiffer et al. |
| 2022/0403375 A1 | 12/2022 | Martinez |
| 2024/0002914 A1 | 1/2024 | Pfeiffer et al. |
| 2024/0044877 A1 | 2/2024 | Price et al. |
| 2024/0272044 A1 | 8/2024 | Bava |

FOREIGN PATENT DOCUMENTS

| | | |
|---|---|---|
| EP | 1019496 B1 | 9/2004 |
| EP | 1482036 B1 | 10/2007 |
| EP | 1841879 A2 | 10/2007 |
| EP | 1594980 B1 | 11/2009 |
| EP | 1967592 B1 | 4/2010 |
| EP | 2258846 A2 | 12/2010 |
| EP | 2145955 B1 | 2/2012 |
| EP | 1905828 B1 | 8/2012 |
| EP | 2136786 B1 | 10/2012 |
| EP | 1908832 B1 | 12/2012 |
| EP | 2540389 A1 | 1/2013 |
| EP | 2635679 B1 | 4/2017 |
| GB | 2097692 A | 11/1982 |
| GB | 2097692 B | 5/1985 |
| GB | 2485850 A | 5/2012 |
| JP | S5949832 A | 3/1984 |
| JP | 2006507921 A | 3/2006 |
| JP | 2006289250 A | 10/2006 |
| JP | 2007193708 A | 8/2007 |
| JP | 2007268350 A | 10/2007 |
| JP | 2009208074 A | 9/2009 |
| JP | 2012525147 A | 10/2012 |

(56) References Cited

FOREIGN PATENT DOCUMENTS

| | | |
|---|---|---|
| RU | 2321638 C2 | 4/2008 |
| WO | WO-84/02000 | 5/1984 |
| WO | WO-95/30782 | 11/1995 |
| WO | WO-9629629 A2 | 9/1996 |
| WO | WO-9641011 A1 | 12/1996 |
| WO | WO-9909217 A1 | 2/1999 |
| WO | WO-99/52708 | 10/1999 |
| WO | WO-0008212 A1 | 2/2000 |
| WO | WO-2000008212 A1 | 2/2000 |
| WO | WO-0026412 A1 | 5/2000 |
| WO | WO-2001002850 A1 | 1/2001 |
| WO | WO-0114589 A2 | 3/2001 |
| WO | WO-0190418 A1 | 11/2001 |
| WO | WO--2001089787 A2 | 11/2001 |
| WO | WO-0231203 A2 | 4/2002 |
| WO | WO-02086148 A1 | 10/2002 |
| WO | WO-03096223 A1 | 11/2003 |
| WO | WO-2004002627 A2 | 1/2004 |
| WO | WO-2004010106 A2 | 1/2004 |
| WO | WO-2004065617 A2 | 8/2004 |
| WO | WO-2004069849 A2 | 8/2004 |
| WO | WO-2004091763 A2 | 10/2004 |
| WO | WO-2004102204 A1 | 11/2004 |
| WO | WO-2004103565 A2 | 12/2004 |
| WO | WO-2004105734 A1 | 12/2004 |
| WO | WO-2005002730 A1 | 1/2005 |
| WO | WO-2005021151 A1 | 3/2005 |
| WO | WO-2005023331 A2 | 3/2005 |
| WO | WO-2005040406 A1 | 5/2005 |
| WO | WO-2005049787 A9 | 6/2005 |
| WO | WO-2005082098 A2 | 9/2005 |
| WO | WO-2006030993 A1 | 3/2006 |
| WO | WO-2006040551 A2 | 4/2006 |
| WO | WO-2006078841 A1 | 7/2006 |
| WO | WO-2006096571 A2 | 9/2006 |
| WO | WO-2007001448 A2 | 1/2007 |
| WO | WO-2007002490 A2 | 1/2007 |
| WO | WO-2007024840 A2 | 3/2007 |
| WO | WO-2007081385 A2 | 7/2007 |
| WO | WO-2007081387 A1 | 7/2007 |
| WO | WO-2007089541 A2 | 8/2007 |
| WO | WO-2007114794 A1 | 10/2007 |
| WO | WO-2007121489 A2 | 10/2007 |
| WO | WO-2007133710 A2 | 11/2007 |
| WO | WO-2007138178 A2 | 12/2007 |
| WO | WO-2007139766 A2 | 12/2007 |
| WO | WO-2007140015 A2 | 12/2007 |
| WO | WO-2007147079 A2 | 12/2007 |
| WO | WO-2007149432 A2 | 12/2007 |
| WO | WO-2008021123 A1 | 2/2008 |
| WO | WO-2008091792 A2 | 7/2008 |
| WO | WO-2008102057 A1 | 8/2008 |
| WO | WO-2008109176 A2 | 9/2008 |
| WO | WO-2008121342 A2 | 10/2008 |
| WO | WO-2008134153 A1 | 11/2008 |
| WO | WO-2008150432 A1 | 12/2008 |
| WO | WO-2009005680 A1 | 1/2009 |
| WO | WO-2009011808 A1 | 1/2009 |
| WO | WO-2009015296 A1 | 1/2009 |
| WO | WO-2009023821 A1 | 2/2009 |
| WO | WO-2009061372 A1 | 5/2009 |
| WO | WO-2009085215 A1 | 7/2009 |
| WO | WO-2009152928 A2 | 12/2009 |
| WO | WO-2010004018 A2 | 1/2010 |
| WO | WO-2010033200 A2 | 3/2010 |
| WO | WO-2010104604 A1 | 9/2010 |
| WO | WO-2010115154 A1 | 10/2010 |
| WO | WO-2010117620 A2 | 10/2010 |
| WO | WO-2010127304 A2 | 11/2010 |
| WO | WO-2010148039 A2 | 12/2010 |
| WO | WO-2010151776 A2 | 12/2010 |
| WO | WO-2011028539 A1 | 3/2011 |
| WO | WO-2011047870 A1 | 4/2011 |
| WO | WO-2011056546 A1 | 5/2011 |
| WO | WO-2011066476 A1 | 6/2011 |
| WO | WO-2011074960 A1 | 6/2011 |
| WO | WO-2012012037 A1 | 1/2012 |
| WO | WO-2012048341 A1 | 4/2012 |
| WO | WO-2012055929 A1 | 5/2012 |
| WO | WO-2012061832 A1 | 5/2012 |
| WO | WO-2012083225 A2 | 6/2012 |
| WO | WO-2012100216 A2 | 7/2012 |
| WO | WO-2012106546 A2 | 8/2012 |
| WO | WO-2012112804 A1 | 8/2012 |
| WO | WO-2012112970 A2 | 8/2012 |
| WO | WO-2012116331 A2 | 8/2012 |
| WO | WO-2012142531 A2 | 10/2012 |
| WO | WO-2012142611 A2 | 10/2012 |
| WO | WO-2012149042 A2 | 11/2012 |
| WO | WO-2012166425 A2 | 12/2012 |
| WO | WO-2012167142 A2 | 12/2012 |
| WO | WO-2013019751 A1 | 2/2013 |
| WO | WO-2013035114 A1 | 3/2013 |
| WO | WO-2013036929 A1 | 3/2013 |
| WO | WO-2013055955 A1 | 4/2013 |
| WO | WO-2013096643 A1 | 6/2013 |
| WO | WO-2013123125 A1 | 8/2013 |
| WO | WO-2013126741 A1 | 8/2013 |
| WO | WO-2013134261 A1 | 9/2013 |
| WO | WO-2013177220 A1 | 11/2013 |
| WO | WO-2014028378 A2 | 2/2014 |
| WO | WO-2014028537 A1 | 2/2014 |
| WO | WO-2014093676 A1 | 6/2014 |
| WO | WO-2014108810 A2 | 7/2014 |
| WO | WO-2014132497 A1 | 9/2014 |
| WO | WO-2014165559 A2 | 10/2014 |
| WO | WO-2015015199 A2 | 2/2015 |
| WO | WO-2015044428 A1 | 4/2015 |
| WO | WO-2015157567 A1 | 10/2015 |
| WO | WO-2015164212 A1 | 10/2015 |
| WO | WO-2015200891 A1 | 12/2015 |
| WO | WO-2016040476 A1 | 3/2016 |
| WO | WO-2016061517 A2 | 4/2016 |
| WO | WO-2016126871 A2 | 8/2016 |
| WO | WO-2016130578 A1 | 8/2016 |
| WO | WO-2016168584 A1 | 10/2016 |
| WO | WO-2017015075 A1 | 1/2017 |
| WO | WO-2017066231 A1 | 4/2017 |
| WO | WO-2017180949 A1 | 10/2017 |
| WO | WO-2017184707 A1 | 10/2017 |
| WO | WO-2017197343 A2 | 11/2017 |
| WO | WO-2018039338 A1 | 3/2018 |
| WO | WO-2018091676 A1 | 5/2018 |
| WO | WO-2018119301 A1 | 6/2018 |
| WO | WO-2018119447 A2 | 6/2018 |
| WO | WO-2018172726 A1 | 9/2018 |
| WO | WO-2018191701 A1 | 10/2018 |
| WO | WO-2018213643 A1 | 11/2018 |
| WO | WO-2018226546 A1 | 12/2018 |
| WO | WO-2018236615 A1 | 12/2018 |
| WO | WO-2019028166 A1 | 2/2019 |
| WO | WO-2019040637 A1 | 2/2019 |
| WO | WO-2019083852 A1 | 5/2019 |
| WO | WO-2019084043 A1 | 5/2019 |
| WO | WO-2019084165 A1 | 5/2019 |
| WO | WO-2019108851 A1 | 6/2019 |
| WO | WO-2019113235 A1 | 6/2019 |
| WO | WO-2019118355 A1 | 6/2019 |
| WO | WO-2019126789 A1 | 6/2019 |
| WO | WO-2019148042 A1 | 8/2019 |
| WO | WO-2019152108 A1 | 8/2019 |
| WO | WO-2019157529 A1 | 8/2019 |
| WO | WO-2019165318 A1 | 8/2019 |
| WO | WO-2019169028 A1 | 9/2019 |
| WO | WO-2019169347 A1 | 9/2019 |
| WO | WO-2019191321 A1 | 10/2019 |
| WO | WO-2019217758 A1 | 11/2019 |
| WO | WO-2020028882 A1 | 2/2020 |
| WO | WO-2020041148 A1 | 2/2020 |
| WO | WO-2020142779 A1 | 7/2020 |
| WO | WO-2020167862 A1 | 8/2020 |
| WO | WO-2020167866 A1 | 8/2020 |
| WO | WO-2020168013 A1 | 8/2020 |
| WO | WO-2020198532 A1 | 10/2020 |

(56) References Cited

FOREIGN PATENT DOCUMENTS

| WO | WO-2021046475 A1 | 3/2021 |
| WO | WO-2021133845 A1 | 7/2021 |
| WO | WO-2021207610 A1 | 10/2021 |
| WO | WO-2021212042 A1 | 10/2021 |
| WO | WO-2021/222302 A1 | 11/2021 |
| WO | WO-2021222301 A1 | 11/2021 |
| WO | WO-2022103712 A1 | 5/2022 |
| WO | WO-2022182682 A1 | 9/2022 |
| WO | WO-2022182785 A1 | 9/2022 |
| WO | WO-2022271908 A1 | 12/2022 |
| WO | WO-2023076528 A2 | 5/2023 |

OTHER PUBLICATIONS

10X Genomics, Inc. CG000208 Rev E. Chromium Next GEM Single Cell V(D)J reagent Kits v1.1 User Guide with Feature Barcode Technology for Cell Surface Protein. 2020.
10X Genomics, Inc. CG000209 Rev D. Chromium Next GEM Single Cell ATAC Reagent Kits v1.1 User Guide. 2020.
10X Genomics, Inc. CG000239 Rev B. Visium Spatial Gene Expression Reagent Kits User Guide. 2020.
10X Genomics, Inc. CG00026. Chromium Single Cell 3' Reagent Kit User Guide. 2016.
10X Genomics, Inc. LIT00003 Rev B Chromium Genome Solution Application Note. 2017.
Abate, A.R. et al. "Beating Poisson encapsulation statistics using close-packed ordering" Lab on a Chip (Sep. 21, 2009) 9(18):2628-2631.
Abate, et al. Beating Poisson encapsulation statistics using close-packed ordering. Lab Chip. Sep. 21, 2009;9(18):2628-31. doi: 10.1039/b909386a. Epub Jul. 28, 2009.
Abate, et al. High-throughput injection with microfluidics using picoinjectors. Proc Natl Acad Sci U S A. Nov. 9, 2010;107(45):19163-6. doi: 10.1073/pNas.1006888107. Epub Oct. 20, 2010.
Abate et al., Valve-based flow focusing for drop formation. Appl Phys Lett. 2009;94. 3 pages.
Adamson et al., "Production of arrays of chemically distinct nanolitre plugs via repeated splitting in microfluidic devices", Lab Chip 6(9): 1178-1186 (Sep. 2006).
Agasti, S.S. et al. "Photocleavable DNA barcode-antibody conjugates allow sensitive and multiplexed protein analysis in single cell" J Am Chem Soc (2012) 134(45):18499-18502.
Agresti, et al. Selection of ribozymes that catalyse multiple-turnover Diels-Alder cycloadditions by using in vitro compartmentalization. Proc Natl Acad Sci U S A. Nov. 8, 2005;102(45):16170-5. Epub Oct. 31, 2005.
Aitman, et al. Copy number polymorphism in Fcgr3 predisposes to glomerulonephritis in rats and humans. Nature. Feb. 16, 2006;439(7078):851-5.
Akselband, "Enrichment of slow-growing marine microorganisms from mixed cultures using gel microdrop (GMD) growth assay and fluorescence-activated cell sorting", J. Exp. Marine Bioi., 329: 196-205 (2006).
Akselband, "Rapid mycobacteria drug susceptibility testing using gel microdrop (GMD) growth assay and flow cytometry", J. Microbiol. Methods, 62:181-197 (2005).
Altemos et al., "Genomic Characterization of Large Heterochromatic Gaps in the Human Genome Assembly," PLOS Computational Biology, May 15, 2014, vol. 10, Issue 5, 14 pages.
Amini, S. et al. "Haplotype-resolved whole-genome sequencing by contiguity-preserving transposition and combinatorial indexing" Nature Genetics (2014) 46:1343-1349 doi:10.1038/ng.3119.
Anna et al.: Formation of dispersions using "flow focusing" in microchannels: Applied Physics Letters, vol. 82, No. 3, pp. 364-366 (2003).
Attia, et al. Micro-injection moulding of polymer microfluidic devices. Microfluidics and nanofluidics. 2009; 7(1):1-28.
Au et al. Improving PacBio Long Read Accuracy by Short Read Alignment. PLoS One 7(10):e46679 (Oct. 4, 2012).

Balikova, et al. Autosomal-dominant microtia linked to five tandem copy-number-variable region at chromosome 4p16. Am J Hum Genet. Jan. 2008;82(1):181-7. doi:10.1016/j.ajhg.2007.08.001.
Bansal et al. "An MCMC algorithm for haplotype assembly from whole-genome sequence data," (2008) Genome Res 18:1336-1346.
Bansal et al. "HapCUT: an efficient and accurate algorithm for the haplotype assembly problem," Bioinformatics (2008) 24:153-i159.
Baret, et al. Fluorescence-activated droplet sorting (FADS): efficient microfluidic cell sorting based on enzymatic activity. Lab Chip. Jul. 7, 2009;9(13):1850-8. doi: 10.1039/b902504a. Epub Apr. 23, 2009.
Baret, "Surfactants in droplet-based microfluidics" Lab Chip (12(3):422-433 (2012).
Bedtools: General Usage, http://bedtools.readthedocs.io/en/latest/content/generalusage .html; Retrieved from the Internet Jul. 8, 2016.
Beer et al. On-Chip, Real-Time, Single-Copy Polymerase Chain Reaction in Picoliter Droplets. Anal Chem 79:8471-8475 (2007).
Bentley et al. "Accurate whole human genome sequencing using reversible terminator chemistry," (2008) Nature 456:53-59.
Boone, et al. Plastic advances microfluidic devices. The devices debuted in silicon and glass, but plastic fabrication may make them hugely successful in biotechnology application. Analytical Chemistry. Feb. 2002; 78A-86A.
Braeckmans et al., Scanning the Code. Modern Drug Discovery. 2003:28-32.
Bransky, et al. A microfluidic droplet generator based on a piezoelectric actuator. Lab Chip. Feb. 21, 2009;9(4):516-20. doi: 10.1039/b814810d. Epub Nov. 20, 2008.
Bray, "The JavaScript Object Notation (JSON) Data Interchange Format," Mar. 2014, retrieved from the Internet Feb. 15, 2015; https://tools.ietf.org/html/rfc7159.
Brenner, et al. "In vitro cloning of complex mixtures of DNA on microbeads: physical separation of differentially expressed cDNAs." Proc Natl Acad Sci U S A. Feb. 15, 2000;97(4):1665-70.
Brouzes, et al. Droplet microfluidic technology for single-cell high-throughput screening. Proc Natl Acad Sci U S A. Aug. 25, 2009;106(34):14195-200. doi: 10.1073/pnas.0903542106. Epub Jul. 15, 2009.
Browning, S.R. et al. "Haplotype Phasing: Existing Methods and New Developments" NaRevGenet (Sep. 16, 2011) 12(10):703-714.
Buchman GW, et al. Selective RNA amplification: a novel method using dUMP-containing primers and uracil DNA glycosylase. PCR Methods Appl. Aug. 1993; 3(1):28-31.
Burns, et al. An Integrated Nanoliter DNA Analysis Device. Science. Oct. 16, 1998;282(5388):484-7.
Burns, et al. Microfabricated structures for integrated DNA analysis. Proc Natl Acad Sci U S A. May 28, 1996; 93(11): 5556-5561.
Burns, et al. The intensification of rapid reactions in multiphase systems using slug flow in capillaries. Lab Chip. Sep. 2001;1(1):10-15. Epub Aug. 9, 2001.
Cappuzzo, et al. Increased HER2 gene copy number is associated with response to gefitinib therapy in epidermal growth factor receptor-positive non-small-cell lung cancer patients. J Clin Oncol. Aug. 1, 2005;23(22):5007-18.
Carroll, "The selection of high-producing cell lines using flow cytometry and cell sorting", Exp. Op. Bioi. Therp., 4:11 1821-1829 (2004).
Chaudhary "A rapid method of cloning functional variable-region antibody genes in *Escherichia coli* as single-chain immunotoxins" Proc. Natl. Acad. Sci USA 87: 1066-1070 (Feb. 1990).
Chechetkin et al., Sequencing by hybridization with the generic 6-mer oligonucleotide microarray: an advanced scheme for data processing. J Biomol Struct Dyn. Aug. 2000;18(1):83-101.
Chen et al. BreakDancer: an algorithm for high-resolution mapping of genomic structural variation. Nature Methods (2009) 6(9):677-681.
Chen, et al. Chemical transfection of cells in picoliter aqueous droplets in fluorocarbon oil. Anal Chem. Nov. 15, 2011;83(22):8816-20. doi: 10.1021/ac2022794. Epub Oct. 17, 2011.
Chien et al. "Multiport flow-control system for lab-on-a-chip microfluidic devices", Fresenius J. Anal Chem, 371:106-111 (Jul. 27, 2001).

(56) References Cited

OTHER PUBLICATIONS

Choi, et al. Identification of novel isoforms of the EML4-ALK transforming gene in non-small cell lung cancer. Cancer Res. Jul. 1, 2008;68(13):4971-6. doi: 10.1158/0008-5472.CAN-07-6158.
Chokkalingam, et al. Probing cellular heterogeneity in cytokine-secreting immune cells using droplet-based microfluidics. Lab Chip. Dec. 21, 2013;13(24):4740-4. doi: 10.1039/c3lc50945a.
Chou, et al. Disposable Microdevices for DNA Analysis and Cell Sorting. Proc. Solid-State Sensor and Actuator Workshop, Hilton Head, SC. Jun. 8-11, 1998; 11-14.
Chu, et al. Controllable monodisperse multiple emulsions. Angew Chem Int Ed Engl. 2007;46(47):8970-4.
Clausell-Tormos et al., "Droplet-based microfluidic platforms for the encapsulation and screening of mammalian cells and multicellular organisms", Chem. Biol. 15:427-437 (2008).
Cleary et al. "Joint variant and de novo mutation identification on pedigrees from high throughput sequencing data," J Comput Biol (2014) 21:405-419.
Cook, et al. Copy-number variations associated with neuropsychiatric conditions. Nature. Oct. 16, 2008;455(7215):919-23. doi: 10.1038/nature07458.
Co-pending PCT/US2019/046940, filed Aug. 16, 2019.
Co-pending U.S. Appl. No. 16/434,076, inventor Giresi; Paul, filed Jun. 6, 2019.
Co-pending U.S. Appl. No. 16/434,084, inventor Giresi; Paul, filed Jun. 6, 2019.
Co-pending U.S. Appl. No. 16/434,102, inventors Price; Andrew D. et al., filed Jun. 6, 2019.
Co-pending U.S. Appl. No. 16/737,762, inventors Price; Andrew D. et al., filed Jan. 8, 2020.
Co-pending U.S. Appl. No. 16/737,770, inventors Belhocine; Zahara Kamila et al., filed Jan. 8, 2020.
Co-pending U.S. Appl. No. 16/789,273, inventors Maheshwari; Arundhati Shamoni et al., filed Feb. 12, 2020.
Co-pending U.S. Appl. No. 16/800,450, inventor Katherine; Pfeiffer, filed Feb. 25, 2020.
Co-pending U.S. Appl. No. 17/014,909, inventor Giresi; Paul, filed Sep. 8, 2020.
Co-pending U.S. Appl. No. 17/148,942, inventors McDermott; Geoffrey et al., filed Jan. 14, 2021.
Co-pending U.S. Appl. No. 17/166,982, inventors McDermott; Geoffrey et al., filed Feb. 3, 2021.
Co-pending U.S. Appl. No. 17/175,542, inventors Maheshwari; Arundhati Shamoni et al., filed Feb. 12, 2021.
Co-pending U.S. Appl. No. 17/220,303, inventor Walter; Dagmar, filed Apr. 1, 2021.
Co-pending U.S. Appl. No. 17/318,364, inventors Bava; Felice Alessio et al., filed May 12, 2021.
Co-pending U.S. Appl. No. 17/381,612, inventor Martinez; Luigi Jhon Alvarado, filed Jul. 21, 2021.
Co-pending U.S. Appl. No. 17/512,241, inventors Hill; Andrew John et al., filed Oct. 27, 2021.
Co-pending U.S. Appl. No. 17/517,408, inventors Salmanzadeh; Alireza et al., filed Nov. 2, 2021.
Co-pending U.S. Appl. No. 17/518,213, inventor Lund; Paul Eugene, filed Nov. 3, 2021.
Co-pending U.S. Appl. No. 17/522,741, inventors Zheng; Xinying et al., filed Nov. 9, 2021.
Co-pending U.S. Appl. No. 17/545,862, inventor Katherine; Pfeiffer, filed Dec. 8, 2021.
Co-pending U.S. Appl. No. 17/573,350, inventor Corey; M. Nemec, filed Jan. 11, 2022.
Co-pending U.S. Appl. No. 17/580,947, inventor Gibbons; Michael, filed Jan. 21, 2022.
Co-pending U.S. Appl. No. 17/957,781, inventor Bava; Felice Alessio, filed Sep. 30, 2022.
Co-pending U.S. Appl. No. 18/046,843, inventor Toh; Mckenzi, filed Oct. 14, 2022.
Co-pending U.S. Appl. No. 16/575,280, filed Sep. 18, 2019.

Damean, et al. Simultaneous measurement of reactions in microdroplets filled by concentration gradients. Lab Chip. Jun. 21, 2009;9(12):1707-13. doi: 10.1039/b821021g. Epub Mar. 19, 2009.
De Bruin et al., UBS Investment Research. Q-Series®: DNA Sequencing. UBS Securities LLC. Jul. 12, 2007. 15 pages.
Demirci, et al. Single cell epitaxy by acoustic picolitre droplets. Lab Chip. Sep. 2007;7(9):1139-45. Epub Jul. 10, 2007.
Depristo et al. A framework for variation discovery and genotyping using next-generation DNA sequencing data. Nature Genet 43:491-498 (2011).
Doerr, "The smallest bioreactor", Nature Methods, 2:5 326 (2005).
Dowding, et al. Oil core/polymer shell microcapsules by internal phase separation from emulsion droplets. II: controlling the release profile of active molecules. Langmuir. Jun. 7, 2005;21(12):5278-84.
Draper, et al. Compartmentalization of electrophoretically separated analytes in a multiphase microfluidic platform. Anal Chem. Jul. 3, 2012;84(13):5801-8. doi: 10.1021/ac301141x. Epub Jun. 13, 2012.
Dressler, et al. Droplet-based microfluidics enabling impact on drug discovery. J Biomol Screen. Apr. 2014; 19(4):483-96. doi: 10.1177/1087057113510401. Epub Nov. 15, 2013.
Drmanac et al., Sequencing by hybridization (SBH): advantages, achievements, and opportunities. Adv Biochem Eng Biotechnol. 2002;77 :75-101.
Droplet Based Sequencing (slides) dated (Mar. 12, 2008).
Duffy et al., Rapid Protyping of Microfluidic Systems and Polydimethylsiloxane, Anal Chem 70:4974-4984 (1998).
Eastburn, et al. Ultrahigh-throughput mammalian single-cell reverse-transcriptase polymerase chain reaction in microfluidic droplets. Anal Chem. Aug. 20, 2013;85(16):8016-21. doi: 10.1021/ac402057q. Epub Aug. 8, 2013.
Eid, et al. Real-time DNA sequencing from single polymerase molecules. Science. Jan. 2, 2009;323(5910):133-8. doi: 10.1126/science.1162986. Epub Nov. 20, 2008.
Ekblom, R. et al. "A field guide to whole-genome sequencing, assembly and annotation" Evolutionary Apps (Jun. 24, 2014) 7(9):1026-1042.
Esser-Kahn, et al. Triggered release from polymer capsules. Macromolecules. 2011; 44:5539-5553.
Fabi, et al. Correlation of efficacy between EGFR gene copy number and lapatinib/capecitabine therapy in HER2-positive metastatic breast cancer. J. Clin. Oncol. 2010; 28:15S. 2010 ASCO Meeting abstract Jun. 14, 2010:1059.
Fisher, et al. A scalable, fully automated process for construction of sequence-ready human exome targeted capture libraries. Genome Biol. 2011;12(1):R1. doi: 10.1186/GB-2011-12-1-r1. Epub Jan. 4, 2011.
Fredrickson, et al. Macro-to-micro interfaces for microfluidic devices. Lab Chip. Dec. 2004;4(6):526-33. Epub Nov. 10, 2004.
Freiberg, et al. Polymer microspheres for controlled drug release. Int J Pharm. Sep. 10, 2004;282(1-2):1-18.
Fu, "A micro fabricated fluorescence-activated cell sorter", Nature Biotech., 17:1109-1111 (1997).
Fulton, et al. Advanced multiplexed analysis with the FlowMetrix system. Clin Chem. Sep. 1997;43(9):1749-56.
Garstecki, et al. Formation of monodisperse bubbles in a microfluidic flow-focusing device. Applied Physics Letters. 2004; 85(13):2649-2651. DOI: 10.1063/1.1796526.
Gartner, et al. The Microfluidic Toolbox—examples for fluidic interfaces and standardization concepts. Proc. SPIE 4982, Microfluidics, BioMEMS, and Medical Microsystems, (Jan. 17, 2003); doi: 10.1117/12.479566.
Gericke, et al. Functional cellulose beads: preparation, characterization, and applications. Chemical reviews 113.7 (2013): 4812-4836.
Ghadessy, et al. Directed evolution of polymerase function by compartmentalized self-replication. Proc Natl Acad Sci USA. 2001;98:4552-4557.
Gonzalez, et al. The influence of CCL3L1 gene-containing segmental duplications on HIV-1/AIDS susceptibility. Science. Mar. 4, 2005;307(5714):1434-40. Epub Jan. 6, 2005.
Gordon et al. "Consed: A Graphical Tool for Sequence Finishing," Genome Research (1998) 8:198-202.

(56) References Cited

OTHER PUBLICATIONS

Granieri, Lucia. Droplet-based microfluidics and engineering of tissue plasminogen activator for biomedical applications. Ph.D. Thesis, Nov. 13, 2009 (131 pages).
Grasland-Mongrain, et al. Droplet coalescence in microfluidic devices. Jan.-Jul. 2003. 31 pages. http://www.eleves.ens.fr/home/grasland/rapports/stage4.pdf.
Guo, et al. Droplet microfluidics for high-throughput biological assays. Lab Chip. Jun. 21, 2012;12(12):2146-55. doi: 10.1039/c2lc21147e. Epub Feb. 9, 2012.
Gyarmati, et al. Reversible disulphide formation in polymer networks: a versatile functional group from synthesis to applications. European Polymer Journal. 2013; 49:1268-1286.
Hashimshony, et al. CEL-Seq: Single-Cell RNA-Seq by Multiplexed Linear Amplification. Cell Rep. Sep. 27, 2012;2(3):666-73. doi: 10.1016/j.celrep.2012.08.003. Epub Aug. 30, 2012.
He, "Selective Encapsulation of Single Cells and Subcellular Organelles into Picoliter- and Femtoliter-Volume Droplets" Anal. Chem 77: 1539-1544 (2005).
Hiatt, et al. Parallel, tag-directed assembly of locally derived short sequence reads. Nat Methods. Feb. 2010;7(2):119-22. Epub Jan. 17, 2010.
Holtze, et al. Biocompatible surfactants for water-in-fluorocarbon emulsions. Lab Chip. Oct. 2008;8(10):1632-9. doi: 10.1039/b806706f. Epub Sep. 2, 2008.
Huang et al. EagleView: A genome assembly viewer for next-generation sequencing technologies, Genome Research (2008) 18:1538-1543.
Huebner, "Quantitative detection of protein expression in single cells using droplet microfluidics", Chem. Commun. 1218-1220 (2007).
Hug, et al. Measurement of the number of molecules of a single mRNA species in a complex mRNA preparation. J Theor Biol. Apr. 21, 2003;221(4):615-24.
Illumina, Inc. An Introduction to Next-Generation Sequencing Technology. Feb. 28, 2012.
Islam, et al. Highly multiplexed and strand-specific single-cell RNA 5' end sequencing. Nat Protoc. Apr. 5, 2012;7(5):813-28. doi: 10.1038/nprot.2012.022.
Jaitin, et al. Massively parallel single-cell RNA-seq for marker-free decomposition of tissues into cell types. Science. Feb. 14, 2014;343(6172):776-9. doi: 10.1126/science.1247651.
Jarosz, M. et al. "Using 1ng of DNA to detect haplotype phasing and gene fusions from whole exome sequencing of cancer cell lines" Cancer Res (2015) 75(suppl5):4742.
Jena, et al. Cyclic olefin copolymer based microfluidic devices for biochip applications: Ultraviolet surface grafting using 2-methacryloyloxyethyl phosphorylcholine. Biomicrofluidics. Mar. 2012;6(1):12822-1 to 12822-12. doi: 10.1063/1.3682098. Epub Mar. 15, 2012.
Jung, et al. Micro machining of injection mold inserts for fluidic channel of polymeric biochips. Sensors. 2007; 7(8):1643-1654.
Kanehisa et al. "KEGG: Kyoto Encyclopedia of Genes and Genomes," Nucleic Acids Research (2000) 28:27-30.
Kaper, et al. Supporting Information for "Whole-genome haplotyping by dilution, amplification, and sequencing." Proc Natl Acad Sci U S A. Apr. 2, 2013;110(14):5552-7. doi: 10.1073/pnas.1218696110. Epub Mar. 18, 2013.
Kaper, et al. Whole-genome haplotyping by dilution, amplification, and sequencing. Proc Natl Acad Sci U S A. Apr. 2, 2013;110(14):5552-7. doi: 10.1073/pnas.1218696110. Epub Mar. 18, 2013.
Kenis, et al. Microfabrication Inside Capillaries Using Multiphase Laminar Flow Patterning. Science. 1999; 285:83-85.
Khomiakova et al., Analysis of perfect and mismatched DNA duplexes by a generic hexanucleotide microchip. Mol Biol(Mosk). Jul.-Aug. 2003;37(4):726-41. Russian. Abstract only.
Kim et al., Albumin loaded microsphere of amphiphilic poly(ethylene glycol)/poly(a-ester) multiblock copolymer. Eu. J. Pharm. Sci. 2004;23:245-51. Available online Sep. 27, 2004.

Kim, et al. Fabrication of monodisperse gel shells and functional microgels in microfluidic devices. Angew Chem Int Ed Engl. 2007;46(11):1819-22.
Kim et al. "HapEdit: an accuracy assessment viewer for haplotype assembly using massively parallel DNA-sequencing technologies," Nucleic Acids Research (2011) pp. W557-W561.
Kim, et al. Rapid prototyping of microfluidic systems using a PDMS/polymer tape composite. Lab Chip. May 7, 2009;9(9):1290-3. doi: 10.1039/b818389a. Epub Feb. 10, 2009.
Kirkness et al. Sequencing of isolated sperm cells for direct haplotyping of a human genome, â€ Genome Res (2013) 23:826-832.
Kitzman et al. "Haplotype-resolved genome sequencing of a Gujarati Indian individual." Nat Biotechnol (2011) 29:59-63.
Kitzman, et al. Noninvasive whole-genome sequencing of a human fetus. Sci Transl Med. Jun. 6, 2012;4(137):137ra76. doi: 10.1126/scitranslmed.3004323.
Kivioja, et al. Counting absolute numbers of molecules using unique molecular identifiers. Nat Methods. Nov. 20, 2011,9(1):72-4.
Klein, et al. Droplet barcoding for single-cell transcriptomics applied to embryonic stem cells. Cell. May 21, 2015;161(5):1187-201. doi: 10.1016/j.cell.2015.04.044.
Klein, et al. Droplet barcoding for single-cell transcriptomics applied to embryonic stem cells. Cell. May 21, 2015; 161:1187-1201.
Knight, et al. Subtle chromosomal rearrangements in children with unexplained mental retardation. Lancet. Nov. 13, 1999;354(9191):1676-81.
Korlach et al., Methods in Enzymology, Real-Time DNA Sequencing from Single Polymerase Molecules, (2010) 472:431-455.
Koster et al., "Drop-based microfluidic devices for encapsulation of single cells", Lab on a Chip The Royal Soc. of Chem. 8: 1110-1115 (2008).
Kutyavin, et al. Oligonucleotides containing 2-aminoadenine and 2-thiothymine act as selectively binding complementary agents. Biochemistry. Aug. 27, 1996;35(34):11170-6.
Lagally, et al. Single-Molecular DNA Amplification and Analysis in an Integrated Microfluidic Device. Anal Chem. Feb. 1, 2001;73(3):565-70.
Lagus, et al. A review of the theory, methods and recent applications of high-throughput single-cell droplet microfluidics. J. Phys. D: Appl. Phys. (2013) 46:114005. (21 pages).
Layer et al. "LUMPY: A probabilistic framework for structural variant discovery," Genome Biology (2014) 15(6):R84.
Lennon et al. A scalable, fully automated process for construction of sequence-ready barcoded libraries for 454. Genome Biology 11:R15 (2010).
Levene, M.J. et al., Zero-Mode Waveguides for Single-Molecule Analysis at High Concentrations, Science, 299(5607):682-686 (Jan. 31, 2003).
Li, et al. Fast and accurate long-read alignment with Burrows-Wheeler transform. Bioinformatics 26.5 (2010): 589-595.
Li, Y., et al., "PEGylated PLGA Nanoparticles as protein carriers: synthesis, preparation and biodistribution in rats," Journal of Controlled Release, vol. 71, pp. 203-211 (2001).
Lippert et al. Algorithmic strategies for the single nucleotide polymorphism haplotype assembly problem, Brief. Bionform (2002) 3:23-31.
Liu, et al. Preparation of uniform-sized PLA microcapsules by combining Shirasu porous glass membrane emulsification technique and multiple emulsion-solvent evaporation method. J Control Release. Mar. 2, 2005;103(1):31-43. Epub Dec. 21, 2004.
Liu, et al. Smart thermo-triggered squirting capsules for Nanoparticle delivery. Soft Matter. 2010; 6(16):3759-3763.
Lo, et al. On the design of clone-based haplotyping. Genome Biol. 2013;14(9):R100.
Loscertales, I.G., et al., "Micro/Nano Encapsulation via Electrified Coaxial Liquid Jets," Science, vol. 295, pp. 1695-1698 (2002).
Love, "A microengraving method for rapid selection of single cells producing antigen-specific antibodies", Nature Biotech, 24:6 703 (Jun. 2006).
Lowe, Adam J. Norbornenes and [n]polynorbornanes as molecular scaffolds for anion recognition. Ph.D. Thesis (May 2010). (361 pages).

(56) References Cited

OTHER PUBLICATIONS

LUPSKI. Genomic rearrangements and sporadic disease. Nat Genet. Jul. 2007;39(7 Suppl):S43-7.

Macosko, et al. Highly Parallel Genome-wide Expression Profiling of Individual Cells Using Nanoliter Droplets. Cell. May 21, 2015;161(5):1202-14. doi: 10.1016/j.cell.2015.05.002.

Madl, et al. "Bioorthogonal Strategies for Engineering Extracellular matrices", Madal, Chritopher, Adv. Funct. Master. Jan. 19, 2018, vol. 28, 1706046, pp. 1-21.

Mair, et al. Injection molded microfluidic chips featuring integrated interconnects. Lab Chip. Oct. 2006;6(10):1346-54. Epub Jul. 31, 2006.

Makino, et al. Preparation of hydrogel microcapsules: Effects of preparation conditions upon membrane properties. Colloids and Surfaces B: Biointerfaces. Nov. 1998; 12(2), 97-104.

Marcus. Gene method offers diagnostic hope. The Wall Street Journal. Jul. 11, 2012.

Margulies 2005 Supplementary methods (Year: 2005).

Margulies et al. "Genome sequencing in microfabricated high-density picoliter reactors", Nature (2005) 437:376-380.

Matochko, et al. Uniform amplification of phage display libraries in monodisperse emulsions. Methods. Sep. 2012;58(1):18-27. doi: 10.1016/j.ymeth.2012.07.012. Epub Jul. 20, 2012.

Mazutis, et al. Selective droplet coalescence using microfluidic systems. Lab Chip. Apr. 24, 2012;12(10):1800-6. doi: 10.1039/c2lc40121e. Epub Mar. 27, 2012.

McCoy, R. et al. "Illumina TruSeq Synthetic Long-Reads Empower De Novo Assembly and Resolve Complex, Highly-Repetitive Transposable Elements" PLOS (2014) 9(9):e1016689.

McKenna, Aaron et al. "The Genome Analysis Toolkit: A MapReduce Framework for Analyzing next-Generation DNA Sequencing Data." Genome Research 20.9 (2010): 1297-1303. PMC. Web. Feb. 2, 2017.

Merriman, et al. Progress in ion torrent semiconductor chip based sequencing. Electrophoresis. Dec. 2012;33(23):3397-417. doi: 10.1002/elps.201200424.

Microfluidic ChipShop. Microfluidic product catalogue. Oct. 2009.

Miller et al. "Assembly Algorithms for next-generation sequencing data," Genomics, 95 (2010), pp. 315-327.

Mirzabekov, "DNA Sequencing by Hybridization—a Megasequencing Method and A Diagnostic Tool?" Trends in Biotechnology 12(1): 27-32 (1994).

Moore, et al. Behavior of capillary valves in centrifugal microfluidic devices prepared by three-dimensional printing. Microfluidics and Nanofluidics. 2011; 10(4):877-888.

Mouritzen et al., Single nucleotide polymorphism genotyping using locked nucleic acid (LNa). Expert Rev Mol Diagn. Jan. 2003;3(1):27-38.

Myllykangas et al. "Efficient targeted resequencing of human germline and cancer genomes by oligonucleotide-selective sequencing," Nat Biotechnol, (2011) 29:1024-1027.

Nagashima, et al. Preparation of monodisperse poly (acrylamide-co-acrylic acid) hydrogel microspheres by a membrane emulsification technique and their size-dependent surface properties. Colloids and Surfaces B: Biointerfaces. Jun. 15, 1998; 11(1-2), 47-56.

Navin. The first five years of single-cell cancer genomics and beyond. Genome Res. Oct. 2015;25(10):1499-507. doi: 10.1101/gr.191098.115.

Nguyen, et al. In situ hybridization to chromosomes stabilized in gel microdrops. Cytometry. 1995; 21:111-119.

Nisisako, et al. Droplet formation in a microchannel network. Lab Chip. Feb. 2002;2(1):24-6. Epub Jan. 18, 2002.

Nisisako, T. et al. Droplet Formation in a Microchannel on PMMA Plate. Micro Total Analysis Systems. 2001. Kluwer Academic Publishers. pp. 137-138.

Nisisako, T. et al., Microfluidics large-scale integration on a chip for mass production of monodisperse droplets and particles, The Royal Society of Chemistry: Lab Chip, (Nov. 23, 2007) 8:287-293.

Novak, et al. Single cell multiplex gene detection and sequencing using microfluidically generated agarose emulsions. Angew Chem Int Ed Engl. Jan. 10, 2011;50(2):390-5. doi: 10.1002/anie.201006089.

Novak, R. et al., "Single cell multiplex gene detection and sequencing using microfluidically generated agarose emulsions" Angew. Chem. Int. Ed. Engl. (2011) 50(2):390-395.

Oberholzer, et al. Polymerase chain reaction in liposomes. Chem Biol. Oct. 1995;2(10):677-82.

Ogawa, et al. Production and characterization of O/W emulsions containing cationic droplets stabilized by lecithin-chitosan membranes. J Agric Food Chem. Apr. 23, 2003;51(9):2806-12.

Okushima, S., et al,. "Controlled Production ofMonodisperse Double Emulsions by Two-Step Droplet Breakup in Microfluidic Devices," Langmuir, vol. 20, pp. 9905-9908 (2004).

Orakdogen, N. "Novel responsive poly(N,N-dimethylaminoethyl methacrylate) gel beads: preparation, mechanical properties and pH-dependent swelling behavior" J Polym Res (2012) 19:9914.

Perez, C., et al., "Poly(lactic acid)-poly(ethylene glycol) Nanoparticles as new carriers for the delivery of plasmid DNA," Journal of Controlled Release, vol. 75, pp. 211-224 (2001).

Perrott, Jimmy. Optimization and Improvement of Emulsion PCR for the Ion Torrent Next-Generation Sequencing Platform. (2011) Thesis.

Peters, B.A. et al. Accurate whole-genome sequencing and haplotyping from 10 to 20 human cells. Nature, 487(7406):190-195 (Jul. 11, 2012).

Pinto, et al. Functional impact of global rare copy number variation in autism spectrum disorders. Nature. Jul. 15, 2010;466(7304):368-72. doi: 10.1038/nature09146. Epub Jun. 9, 2010.

Plunkett, et al. Chymotrypsin responsive hydrogel: application of a disulfide exchange protocol for the preparation of methacrylamide containing peptides. Biomacromolecules. Mar.-Apr. 2005;6(2):632-7.

Priest, et al. Generation of Monodisperse Gel Emulsions in a Microfluidic Device, Applied Physics Letters, 88:024106 (2006).

Pushkarev et al. Single-molecule sequencing of an individual human genome, Nature Biotech (2009) 17:847-850.

Ramsey, J.M. "The burgeoning power of the shrinking laboratory" Nature Biotech (1999) 17:1061-1062.

Ramskold et al. (2012) "Full-length mRNA-Seq from single-cell levels of RNA and individual circulating tumor cells" Nature Biotechnology 30(8):777-782.

Ritz, A. et al. "Characterization of structural variants with single molecule and hybrid sequencing approaches" Bioinformatics (2014) 30(24):3458-3466.

Roche. Using Multiplex Identifier (MID) Adaptors for the GS FLX Titanium Chemistry Basic MID Set Genome Sequencer FLX System, Technical Bulletin 004-2009, (Apr. 1, 2009) pp. 1-11. URL: http://454.com/downloads/my454/documentation/technical-bulletins/TCB-09004 Using MultiplexIdentifierAdaptorsForTheGSFLXTitaniumSeriesChemistry-BasicMIDSet.pdf.

Ropers. New perspectives for the elucidation of genetic disorders. Am J Hum Genet. Aug. 2007;81(2):199-207. Epub Jun. 29, 2007.

Rotem, A. et al., "High-throughput single-cell labeling (Hi-SCL) for RNA-Seq using drop-based microfluidics" PLOS One (May 22, 2015) 0116328 (14 pages).

Rotem, et al. High-Throughput Single-Cell Labeling (Hi-SCL) for RNA-Seq Using Drop-Based Microfluidics. PLoS One. May 22, 2015;10(5):e0116328. doi: 10.1371/journal.pone.0116328. eCollection 2015.

Rotem, et al. Single Cell Chip-Seq Using Drop-Based Microfluidics. Abstract #50. Frontiers of Single Cell Analysis, Stanford University Sep. 5-7, 2013.

Ryan, "Rapid assay for mycobacterial growth and antibiotic susceptibility using gel microdrop and encapsulation", J. Clinical Microbial., 33:7 1720-1726 (1995).

Saikia, et al. Simultaneous multiplexed amplicon sequencing and transcriptome profiling in single cells. Nat Methods. Jan. 2019;16(1):59-62. doi: 10.1038/s41592-018-0259-9. Epub Dec. 17, 2018.

Schirinzi et al., Combinatorial sequencing-by-hybridization: Analysis of the NF1 gene. Genet Test. 2006 Spring;10(1):8-17.

(56) References Cited

OTHER PUBLICATIONS

Schmitt, "Bead-based multiplex genotyping of human papillomaviruses", J. Clinical Microbial., 44:2 504-512 (2006).
Schubert, et al. Microemulsifying fluorinated oils with mixtures of fluorinated and hydrogenated surfactants. Colloids and Surfaces A; Physicochemical and Engineering Aspects, 84(1994) 97-106.
Sebat, et al. Strong association of de novo copy number mutations with autism. Science. Apr. 20, 2007;316(5823):445-9. Epub Mar. 15, 2007.
Seiffert, et al. Microfluidic fabrication of smart microgels from macromolecular precursors. 2010. Polymer.
Seiffert, et al. Smart microgel capsules from macromolecular precursors. J Am Chem Soc. May 12, 2010;132(18):6606-9. doi: 10.1021/ja102156h.
Seiffert, S. et al., "Smart microgel capsules from macromolecular precursors" J. Am. Chem. Soc. (2010) 132:6606-6609.
Shah, et al. "Fabrication of mono disperse thermosensitive microgels and gel capsules in micro fluidic devices", Soft Matter, 4:2303-2309 (2008).
Shendure, et al., Accurate Multiplex Polony Sequencing of an Evolved Bacterial Genome. Science 309.5741 (Sep. 2005): 1728-1732. XP002427180, ISSN: 0036-8075, DOI: 10.1126/Science.1117839.
Shimkus, et al. A chemically cleavable biotinylated nucleotide: usefulness in the recovery of protein-DNA complexes from avidin affinity columns. Proc Natl Acad Sci U S A. May 1985;82(9):2593-7.
Shlien, et al. Copy number variations and cancer. Genome Med. Jun. 16, 2009;1(6):62. doi:10.1186/gm62.
Shlien, et al. Excessive genomic DNA copy number variation in the Li-Fraumeni cancer predisposition syndrome. Proc Natl Acad Sci U S A. Aug. 12, 2008;105(32):11264-9. doi: 10.1073/pnas.0802970105. Epub Aug. 6, 2008.
Simeonov et al., Single nucleotide polymorphism genotyping using short, fluorescently labeled locked nucleic acid (LNA) probes and fluorescence polarization detection. Nucleic Acids Res. Sep. 1, 2002;30(17):e91.
Smith, et al. Highly-multiplexed barcode sequencing: an efficient method for parallel analysis of pooled samples. Nucleic Acids Research, 38(13): e142 (2010).
Song, et al. Reactions in droplets in microfluidic channels. Angew Chem Int Ed Engl. Nov. 13, 2006;45(44):7336-56.
Sorokin et al., Discrimination between perfect and mismatched duplexes with oligonucleotide gel microchips: role of thermodynamic and kinetic effects during hybridization. J Biomol Struct Dyn. Jun. 2005;22(6):725-34.
SSH Tunnel—Local and Remote Port Forwarding Explained With Examples, Trackets Blog, http://blog.trackets.com/2014/05/17/ssh-tunnel-local-and-remote-port-forwarding-explained-with-examples.html; Retrieved from the Internet Jul. 7, 2016.
Su, et al., Microfluidics-Based Biochips: Technology Issues, Implementation Platforms, and Design-Automation Challenges. IEEE Transactions on Computer-Aided Design of Integrated Circuits and Systems. 2006;25(2):211-23. (Feb. 2006).
Sun et al., Progress in research and application of liquid-phase chip technology. Chinese Journal Experimental Surgery. May 2005;22(5):639-40.
Tawfik, D.S., et al., "Man-made cell-like compartments for molecular evolution," Nature Biotechnology, vol. 16, pp. 652-656 (1998).
Tewhey, et al. Microdroplet-based PCR amplification for large-scale targeted sequencing. Nat Biotechnol. Nov. 2009;27(11):1025-31. doi: 10.1038/nbt.1583. Epub Nov. 1, 2009.
Tewhey et al. The importance of phase information for human genomics, Nat Rev Genet (2011) 12:215-223.
Thaxton, C.S. et al. "A Bio-Bar-Code Assay Based Upon Dithiothreitol Oligonucleotide Release" Anal Chem (2005) 77:8174-8178.
The SAM/BAM Format Specificatio Working Group, "Sequence Alignment/ Map Format Specification," Sep. 6, 2016.
Theberge, et al. Microdroplets in microfluidics: an evolving platform for discoveries in chemistry and biology. Angew Chem Int Ed Engl. Aug. 9, 2010;49(34):5846-68. doi: 10.1002/anie.200906653.
Thorsen, et al. Dynamic pattern formation in a vesicle-generating microfluidic device. Physical Review Letters. American Physical Society. 2001; 86(18):4163-4166.
Tonelli, et al. Perfluoropolyether functional oligomers: unusual reactivity in organic chemistry. Journal of fluorine chemistry. 2002; 118(1) 107-121.
Tubeleviciute, et al. Compartmentalized self-replication (CSR) selection of Thermococcus litoralis Sh1B DNa polymerase for diminished uracil binding. Protein Eng Des Sel. Aug. 2010;23(8):589-97. doi: 10.1093/protein/gzq032. Epub May 31, 2010.
Turchinovich, et al. "Capture and Amplification by Tailing and Switching (CATS): An Ultrasensitive Ligation-Independent Method for Generation of DNA Libraries for Deep Sequencing from Picogram Amounts of DNA and RNA." RNA Biology 11.7 (2014): 817-828. PMC. Web. Nov. 13, 2017.
Turner, et al. Methods for genomic partitioning. Annu Rev Genomics Hum Genet. 2009;10:263-84. doi: 10.1146/annurev-genom-082908-150112. Review.
Uttamapinant, et al. Fast, cell-compatible click chemistry with copper-chelating azides for biomolecular labeling. Angew. Chem. Int. End. Engl., Jun. 11, 2012: 51(24) pp. 5852-5856.
Voskoboynik, A. et al. The genome sequence of the colonial chordate, Botryllus schlosseri. eLife, 2:e00569 (2013). doi: 10.7554/eLife.00569. Epub Jul. 2, 2013.
Wagner, et al. Biocompatible fluorinated polyglycerols for droplet microfluidics as an alternative to PEG-based copolymer surfactants. Lab Chip. Jan. 7, 2016;16(1):65-9. doi: 10.1039/c5lc00823a. Epub Dec. 2, 2015.
Wang, et al. A novel thermo-induced self-bursting microcapsule with magnetic-targeting property. Chemphyschem. Oct. 5, 2009;10(14):2405-9.
Wang, et al. Digital karyotyping. Proc Natl Acad Sci U S A. Dec. 10, 2002;99(25):16156-61. Epub Dec. 2, 2002.
Wang et al., Single nucleotide polymorphism discrimination assisted by improved base stacking hybridization using oligonucleotide microarrays. Biotechniques. 2003;35:300-08.
Weaver, "Rapid clonal growth measurements at the single-cell level: gel microdroplets and flow cytometry", Biotechnology, 9:873-877 (1991).
Weigl, et al. Microfluidic Diffusion-Based Separation and Detection. Science. 1999; pp. 346-347.
Wheeler et al., "Database resources of the National Center for Biotechnology Information," Nucleic Acids Res. (2007) 35 (Database issue): D5-12.
Whitesides, "Soft lithography in biology and biochemistry", Annual Review of Biomedical Engineering, 3:335-373 (2001).
Williams, et al. Amplification of complex gene libraries by emulsion PCR. Nature Methods. 2006;3(7):545-50.
Woo, et al. G/C-modified oligodeoxynucleotides with selective complementarity: synthesis and hybridization properties. Nucleic Acids Res. Jul. 1, 1996;24(13):2470-5.
Xia and Whitesides, Soft Lithography, Ann. Rev. Mat. Sci. 28:153-184 (1998).
Yamamoto, et al. Chemical modification of Ce(IV)/EDTA-base artificial restriction DNA cutter for versatile manipulation of double-stranded DNA. Nucleic Acids Research. 2007; 35(7):e53.
Zerbino, Daniel, "Velvet Manual—version 1.1," Aug. 15, 2008, pp. 1-22.
Zerbino, D.R. "Using the Velvet de novo assembler for short-read sequencing technologies" Curr Protoc Bioinformatics. Sep. 2010;Chapter 11:Unit 11.5. doi: 10.1002/0471250953.bi1105s31.
Zerbino et al. "Velvet: Algorithms for de novo short read assembly using de Bruijn graphs," Genome Research (2008) 18:821-829.
Zhang, "Combinatorial marking of cells and organelles with reconstituted fluorescent proteins", Cell, 119:137-144 (Oct. 1, 2004).
Zhang, et al. Degradable disulfide core-cross-linked micelles as a drug delivery system prepared from vinyl functionalized nucleosides via the RAFT process. Biomacromolecules. Nov. 2008;9(11):3321-31. doi: 10.1021/bm800867n. Epub Oct. 9, 2008.

(56) References Cited

OTHER PUBLICATIONS

Zhang, et al. One-step fabrication of supramolecular microcapsules from microfluidic droplets. Science. Feb. 10, 2012;335(6069):690-4. doi: 10.1126/science.1215416.

Zhang, et al. Reconstruction of DNA sequencing by hybridization. Bioinformatics. Jan. 2003;19(1):14-21.

Zhao, J., et al., "Preparation of hemoglobin-loaded Nano-sized particles with porous structure as oxygen carriers," Biomaterials, vol. 28, pp. 1414-1422 (2007).

Zheng, et al. Massively parallel digital transcriptional profiling of single cells. Nat Commun. Jan. 16, 2017;8:14049. doi: 10.1038/ncomms14049.

Zheng, X. SeqArray: an R/Bioconductor Package for Big Data Management of Genome-Wide Sequencing Variants, Department of Biostatistics; University of Washington-Seattle; Dec. 28, 2014.

Zheng, X.Y. et al. "Haplotyping germline and cancer genomes with high-throughput linked-read sequencing" Nature Biotech (Feb. 1, 2016) 34(3):303-311.

Zhu, et al. Reverse transcriptase template switching: a SMART approach for full-length cDNA library construction. Biotechniques. Apr. 2001;30(4):892-7.

Zhu, et al. Synthesis and self-assembly of highly incompatible polybutadienepoly(hexafluoropropoylene oxide) diblock copolymers. Journal of Polymer Science Part B: Polymer Physics. 2005; 43(24):3685-3694.

ZIMMERMANN et at., Microscale production of hybridomas by hypo-osmolar electrofusion. Hum. Antibodies Hybridomas. Jan. 1992;3(1 ): 14-8.

Zong et al. Genome-Wide Detection of Single Nucleotide and Copy Number Variations of a Single Human Cell. Science 338(6114):1622-1626 (2012).

Co-pending U.S. Appl. No. 18/643,684, inventor Bava; Felice Alessio, filed Apr. 23, 2024.

Co-pending U.S. Appl. No. 18/743,583, inventor Nagendran; Monica, filed Jun. 14, 2024.

Co-pending U.S. Appl. No. 18/795,976, inventors Meer; Elliott et al., filed Aug. 6, 2024.

Co-pending U.S. Appl. No. 18/392,684, inventors Fernandes; Sunjay Jude et al., filed Dec. 21, 2023.

SEQUENCING METHODS

CROSS REFERENCE

This application is a continuation of U.S. application Ser. No. 16/428,656, filed May 31, 2019, which is a continuation of U.S. application Ser. No. 14/470,746, filed Aug. 27, 2014, now U.S. Pat. No. 10,395,758, which claims priority to U.S. Provisional Application No. 61/979,973, filed Apr. 15, 2014, U.S. Provisional Application No. 61/916,566, filed Dec. 16, 2013, and U.S. Provisional Application No. 61/872,597, filed Aug. 30, 2013, each of which is entirely incorporated herein by reference for all purposes.

BACKGROUND

The understanding of human genetics is rapidly expanding, fueled in part by developments in large-scale sequencing technologies. The results obtained from the sequencing of a genome, however, still present numerous production and bioinformatics challenges. The sheer volume of data obtained in a single sequencing experiment poses a remarkable data analysis challenge. The quality of the data, which often comprise millions to hundreds of millions of small sequence reads, poses yet another challenge. The development of streamlined, highly automated pipelines for data analysis is critical for transition from technology adoption to accelerated research and publication. Many obstacles remain in developing methods, algorithms, and computer program products for the analysis of sequencing data.

SUMMARY OF THE INVENTION

In some embodiments, the invention provides a method of analyzing sequencing data associated with a sample, the method comprising: a) receiving by a computer system a first sequencing read associated with a sequencing assay while the sequencing assay is in progress, wherein the computer system comprises a processor; and b) comparing by the processor the first sequencing read with another sequence to provide a comparison before the sequencing assay is complete.

In some embodiments, the invention provides a computer program product comprising a computer-readable medium having computer-executable code encoded therein, the computer-executable code adapted to be executed to implement a method of analyzing sequencing data, the method comprising: a) providing a sequencing data analysis system, wherein the sequencing data analysis system comprises: i) a receiving module configured to receive sequencing data associated with a sequencing assay while the sequencing assay is in progress; and ii) an alignment module configured to align sequencing data while the sequencing assay is in progress; b) receiving by the receiving module a set of sequencing reads associated with the sequencing assay while the sequencing assay is in progress; and c) performing an alignment by the alignment module of at least one received sequencing read with another sequence while the sequencing assay is in progress.

DETAILED DESCRIPTION

Figure 1:
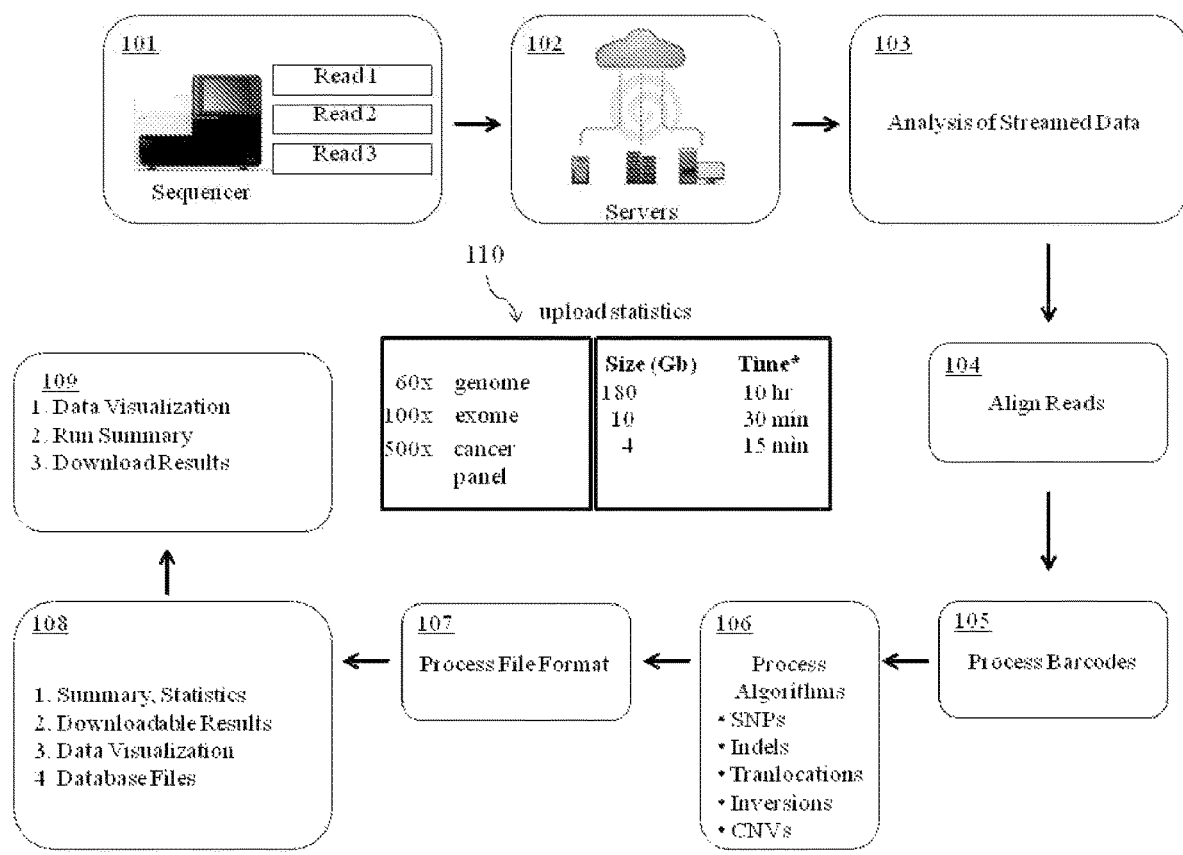
FIG. 1 is an overall schematic of a process wherein genomic data is streamed during sequencing and analyzed in real-time.

The disclosure provides methods and computer program products with applications in medical diagnosis and in the study of disease, health, population, and evolutionary genetics. The invention provides streaming, real-time processing of haplotype phasing, structural variant identification, variant correction, phasing of structural variants, de novo assembly, and barcoded alignment of sequencing reads. The invention can determine to which haplotype in a pair of haplotypes a sequencing read corresponds. A variant phasing algorithm of the invention can distinguish between alleles of maternal and of paternal origin. The invention presented herein can, for example, utilize a barcode present in a sequencing read to distinguish identified polymorphims onto separate haplotypes and reduce error rates.

Rapid advances in DNA and RNA sequencing technologies have generated a wealth of genomic data. Such data can provide a powerful new tool permitting the identification and annotation of the genome of an organism. Sequencing data can identify and characterize: a) genes responsible for giving an organism unique characteristics; b) genes conserved among species; c) genes that illustrate evolutionary changes among organisms; d) genes associated with health/disease; e) genes that confer disease resistance to an organism; f) genes associated with agricultural and nutritional properties; and/or g) genes associated with natural physiological processes, such as aging.

Despite the growing availability of sequencing data, the ability to process the information found within the data rapidly, effectively, and accurately remains a challenge. Sequencing diploid genomes presents the challenge of distinguishing nearly identical sequencing reads based on paternal or maternal origin. The ambiguity associated with distinguishing highly similar sequencing reads derived from distinct chromosomes introduces the issue of "phasing," or determining within which of the two chromosomes a sequencing read variant is associated. Questions of phasing are more complex than questions of distinguishing non-homologous chromosomes.

Single gene and/or genomic duplications provide another obstacle in the analysis of genomic data. Multiple copies of a variant/mutation can be present in one or more chromosomes, and the identification of the correct copy number can improve the value of genomic sequencing. Small insertions and/or deletions ("INDELs") can be found throughout a genome, the characterization of which is a challenge. The ability to characterize translocations and inversions, and corresponding breakpoints in a genome, can be valuable.

The invention provides an efficient solution to the greatest challenges in sequencing data analysis, and is capable of analyzing sequencing data that presented in distinct sequencing formats. The methods herein can distinguish variants on separate homologous chromosomes using phasing information. Phased sequencing can capture unique chromosomal content, including mutations that differ across chromosome copies, such as distinct mutations in distinct haplotypes, and variations within the same chromosome copy, while preserving haplotype phasing information. The computer program products and methods provided herein also distinguish between sequencing errors and real variations/mutations within a sequencing read with a low error rate, and identify and characterize, for example, INDELs, translocations, inversions, and multiple copies of a gene or chromosome.

Barcodes.

The term "barcode," as used herein, refers to a label, or identifier, that can be attached to an analyte to convey information about the analyte. Barcodes can have a variety of different formats, for example, barcodes can include: polynucleotide barcodes; random nucleic acid and/or amino acid sequences; and synthetic nucleic acid and/or amino acid sequences. A barcode can be attached to an analyte in a reversible or irreversible manner. A barcode can be added to, for example, a fragment of a DNA/RNA sample before, during, and/or after sequencing of the sample. Barcodes can allow for identification and/or quantification of individual sequencing-reads in real time.

Each partial-read, longer-partial, or full-read fragment generated during sequencing is associated with a barcode. In some embodiments, a sample can be associated with a plurality of distinct barcodes. As more data streams from a sequencer to one or a plurality of servers, the sequencing reads can be processed based on barcodes, thereby grouping partial-reads, longer-partial, and full-reads associated with a common barcode. Barcode analysis resolves ambiguity and provides haplotype phasing information.

Some embodiments, for example polynucleotide sequencing, can utilize unique barcodes to identify a sequencing read and, for example, to assemble a larger digital representation of a sample from shorter sequencing reads. Depending upon the specific application, barcodes can be added to a sample before or during a sequencing of the sample. For example, a sample can be fragmented and physically separated prior to sequencing. A barcode can be added to a fragmented sample, for example, by dividing the fragmented sample into partitions so that one or more barcodes can be introduced into a particular partition. Each partition can contain a different set of barcodes. The presence of the same barcode on multiple sequences can provide information about the origin of the sequence. For example, a barcode can indicate that the sequence came from a particular partition and/or a specific region of a genome. In some embodiments, a first sequencing read and another sequence share a common barcode. This feature can be particularly useful for an assembly of a larger sequencing read. Depending upon the specific application, barcodes can be attached to analyte fragments in a reversible or irreversible manner. In some embodiments, an algorithm and a computer program product can detect, process, distinguish, group, separate, filter out, and assemble in real-time a plurality of streaming sequencing reads associated with a plurality of barcodes.

Streaming Sequencing Data.

The streaming sequencing algorithms and computer program products herein allow for the analysis of sequencing data to start even before a sequencing experiment is complete. The systems and methods of the invention can process partial information as the partial information is received. A sequencing read can comprise a barcode. In some embodiments, the invention described herein comprises a method of analyzing sequencing data associated with a sample, the method comprising: a) receiving by a computer system a first sequencing read associated with a sequencing assay while the sequencing experiment is in progress, wherein the computer system comprises a processor; and b) comparing by the processor the first sequencing read with another sequence to provide a comparison before the sequencing assay is complete. The other sequence can be another sequencing read or a reference sequence, such as a partial or complete reference genome. The other sequence can be obtained, for example, from an experiment or a database.

Any of the alignments, comparisons, analysis, and processes described herein can occur in real-time while a sequencing assay is still running and inputting data into the system. Data acquired initially or later in the processes are integrated seamlessly as if all the data had been received together. However, the rate at which the streaming methods can process data is much faster than that of a system that cannot stream and process data in real-time.

FIG. 1 illustrates an overall schematic of a process wherein genomic data are streamed during sequencing and analyzed in real-time with methods and computer-program products of the invention. Sequencing reads are generated with a Sequencer 101. Data associated with the sequencing reads are streamed in real-time and uploaded on Servers 102, for example, Amazon EC2™ cloud computing servers. Real-time streaming can allow the transfer of data from partial sequencing reads into a server. As the data are streamed into servers, data analysis by one or more exemplary algorithms starts 103. A computer-program product of the invention permits the process of data analysis to commence even as the sequencing is ongoing. In some embodiments, data from a sequencer of partial, full, and/or complete sequencing reads is streamed from a sequencer to a server as the sequencer runs.

The data collected in the process of streaming data from a sequencer to a server as the sequencer is running can be analyzed by streaming sequencing algorithms of the invention. In some embodiments, a computer program product can process partial information as streamed in real-time. In some embodiments, a computer program product comprises specific modules to analyze sequencing read data comprising barcodes. A module of a computer program product can, for example, align 104 a plurality of partial and/or full sequencing reads to a reference genome. The computer program products and methods of the invention contemplate the analysis of a variety of file formats for data types.

A module of a computer program product of the invention can process a plurality of different file formats for distinct data types. Non-limiting examples of file formats and associated sources of data are listed in TABLE 2.

TABLE 2

| File Format | Source of Data |
| --- | --- |
| SAM (.sam) | Sequence alignment data |
| BAM (.bam) | Sequence alignment data |
| VCF (.vcf) | Variant call format |
| SEG (.seg) | Segmented data |
| CBS (.cbs) | Segmented data |
| MUT (.mut) | Mutation data |
| LOH (.loh) | Loss of Heterozygosity data |
| GFF (.gff) | Genome annotation data |
| GFF3 (.gff3) | Genome annotation data |
| BED (.bed) | Genome annotation data |
| GCT (.gct) | Gene expression data |
| RES (.res) | Gene expression data |
| GCT (.mai.gct) | RNAi data |
| IGV (.igv) | Numeric data |
| TAB (.tab) | Numeric data |
| WIG (.wig) | Numeric data |
| CN (.cn) | Copy number data |
| SNP (.snp) | Single nucleotide polymorphism data |
| TDF (.tdf) | ChIP-Seq, RNA-Seq data |
| GISTIC (.gistic) | Amplification/deletion data |
| FASTA | Reference sequence (nucleic acid or protein) |

The invention can process barcodes and BAM File 105, to perform a method described herein. A BAM file (.bam) is the binary version of a SAM file. A SAM file (.sam) is a tab-delimited text file that contains sequence alignment data. A module can process barcodes and BAM Files 105, thereby associating a plurality of partial-read sequences with a genomic region.

One or a plurality of modules can be specifically programmed to provide, for example, an accurate solution to problems of haplotype phasing, Single Nucleotide Polymorphism (SNPs) identification, small insertion and deletion (INDELs) analysis, translocation analysis, inversion analysis, and/or copy number variant analysis (CNV) 106. The data generated in 106 can be processed, for example, in Variant Call Format (VCF) File(s) format 107. A module of a computer-program product of the invention processes data generated in 106 into a VCF File or another useful format 107. The VCF specified format of a text file can be processed by an algorithm comprised within a computer program product of the invention to store gene sequence variations of a sequencing read. Other formats, for example, the General Feature Format (GFF), can be processed by an algorithm and a computer program product of the invention to store all of the genetic data, including redundant sequences across the genome. In some embodiments, the selection of a file format that differentiates between redundant and non-redundant regions of a genome contributes to the efficiency of an analysis of sequencing reads.

A module of a computer program product can be programmed to produce files 108 for front-end analysis. A module 108 can, for example, produce and archive files corresponding to a summary and statistical analysis of the data associated with 101-107. A module 108 can provide downloadable files, visualization files, and database files. All data associated with 101-108 can be visually displayed. A computer program product module 109 can be programmed to output the data on a visual display, to run a summary of the data, and to upload, transmit, save, store, and/or copy the results. Data can be drawn, for example, from a genome, from an exome, or from a cancer panel 110.

Figure 2:
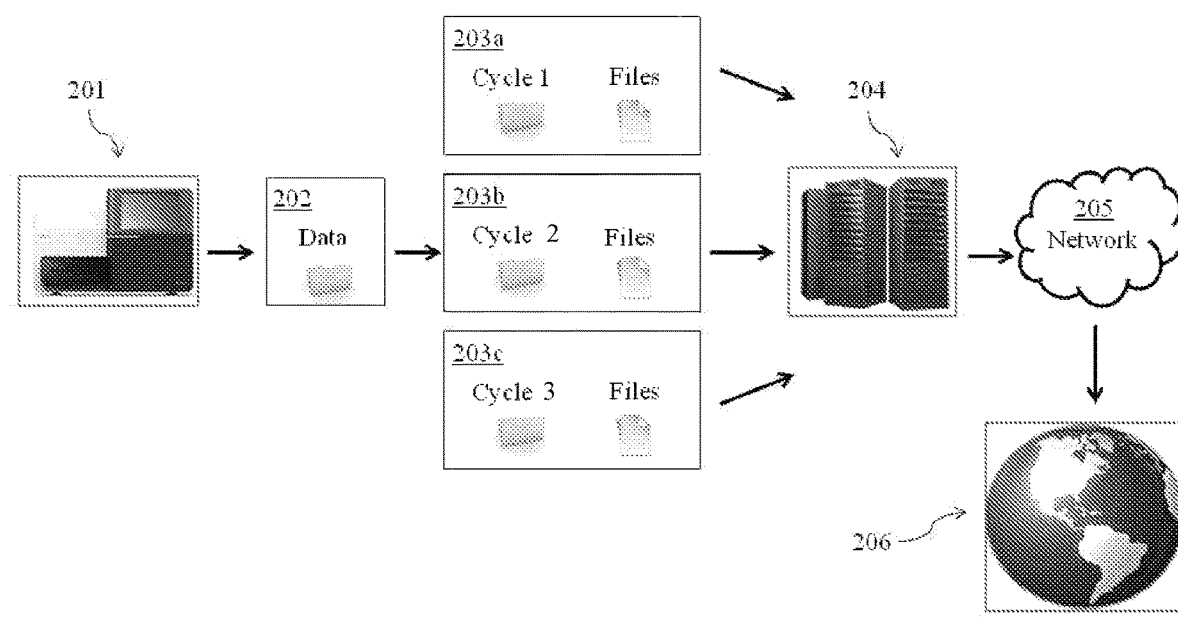
FIG. 2 is an overview of a process wherein genomic data can be shared within a global network.

FIG. 2 is an overall representation of the real-time transmission of a stream of data from partial-read sequences. 201 represents an illustrative sequencer generating sequencing reads from a sample. Data 202 from one or several sequencing cycles, for example, 203$a$, 203$b$, and 203$c$ is transmitted into a server 204. The server 204 can transmit data from 203$a$, 203$b$, and 203$c$ to a network 205. The network 205 can be a wired network or a wireless network, such as the cloud. All data described in 102-109 and 202-205 can be transmitted from one location to a different location. In some embodiments, the data can be transmitted from one geographic boundary to a second geographic boundary 206. In some embodiments, the methods and computer program products of the invention can provide a tangible product, such as a report characterizing the sequencing data of a subject.

Alignment.

A sequence alignment can be a way of arranging nucleic acid or amino acid sequences to identify regions of similarity or overlap. An alignment of sequencing reads to a reference sequence can arrange the sequencing reads for construction of a candidate sequence. An alignment of a sequencing read to a reference sequence can be a global-alignment or a local-alignment. A global alignment can align a sequencing read to an entire length of a reference sequence. A local alignment can align a sequencing read or portions of a sequencing read to a window of a reference sequence. A local alignment can identify regions of similarity within sequencing reads and that can be widely divergent overall. An alignment can use an individual sequencing read or a candidate sequence derived from multiple sequencing reads.

Figure 3:
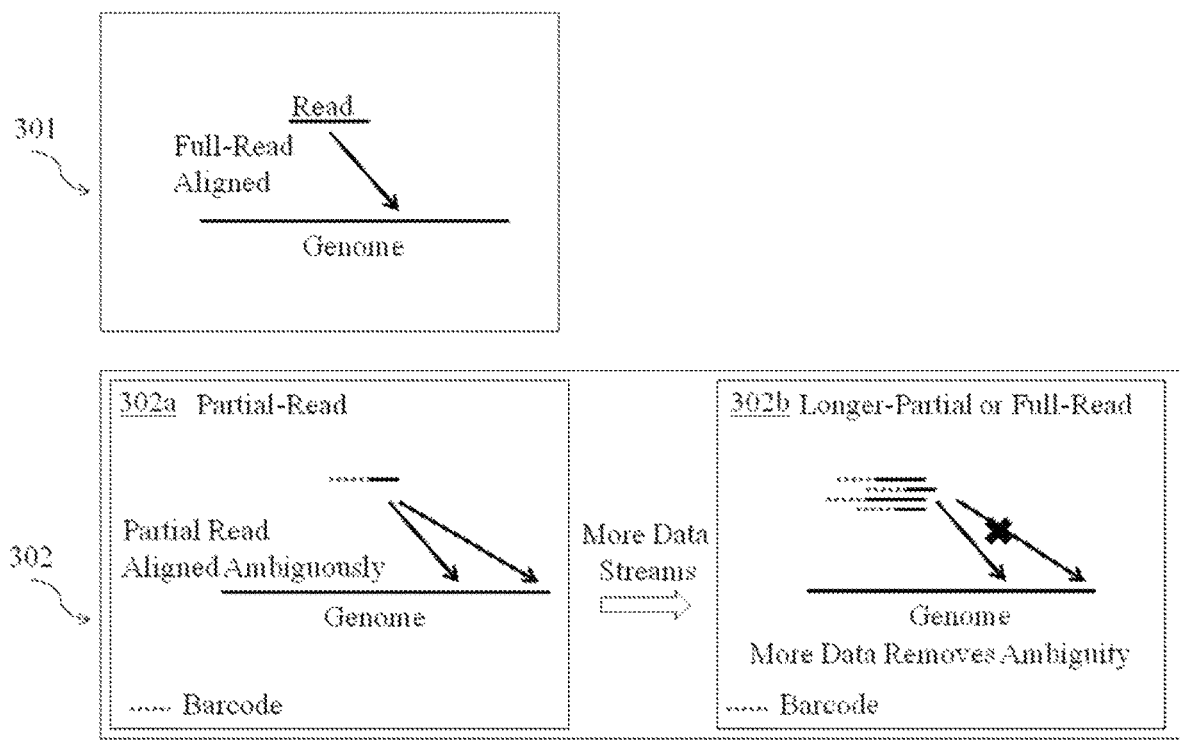
FIG. 3 illustrates example alignments of sequence reads to a reference genome.

FIG. 3 illustrates alignment of sequencing reads to a reference sequence. 301 illustrates an alignment of a full-read sequence to a reference genome. 302 illustrates reducing an ambiguity of an alignment (302$a$) of a partial-read sequence to a reference sequence as more data associated with longer-partial or full-read sequences with the same barcode are streamed and aligned to the reference genome (302$b$).

Variant Phasing and Non-Variant Phasing Algorithms.

Figure 4:
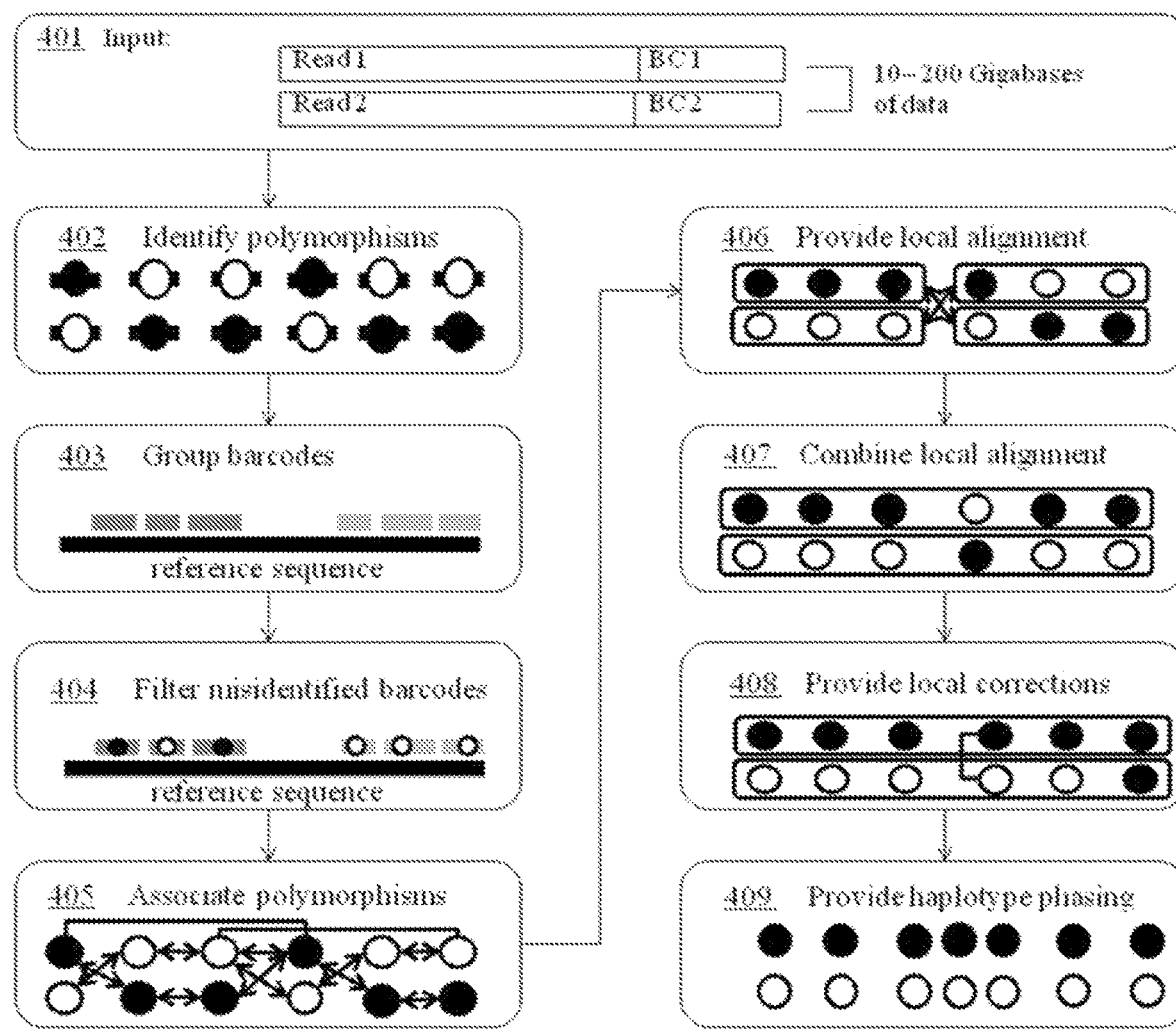
FIG. 4 is a visual representation of example modules of a variant phasing algorithm that separates polymorphisms onto separate haplotypes.

A method herein can sort sequencing reads into separate haplotypes based on mutations, such as single nucleotide polymorphisms (SNPs), or lack thereof, present in the sequencing reads. A mutation can be identified based on a comparison among sequencing reads or against a reference sequence. FIG. 4 is a visual representation of illustrative modules that can be programmed within a variant phasing algorithm to separate sequencing reads into separate haplotypes based on identified mutations. 401 illustrates sequencing Read 1, which is associated with Barcode 1, and sequencing Read 2, which is associated with Barcode 2. 401 also illustrates that an input received can be associated with a quantity of digital data, for example, 10-200 gigabases of data. A first module 402 can identify single nucleotide polymorphisms by comparing sequencing reads with a reference sequence. The module 402 can scan a sequencing-read for previously-characterized polymorphisms and uncharacterized polymorphisms. Each dot in 402 represents a SNP on a sequencing read, represented by a bar.

A module of a computer program product 403 can group sequencing reads sharing common barcodes for alignment against a reference sequence. A grouping of identical or similar barcodes can be aligned against a common region of the reference sequence to identify sequencing reads that originate from physically proximate regions of a sample. 403 illustrate two groups of sequencing reads represented by bars. The left triplet of reads share barcode and the right triplet of reads share the same barcode. Module 404 can filter out misidentified barcodes, for example, barcodes that are similar but not identical to those that had been previously grouped and barcodes associated with sequencing reads that do not contain an initially-identified single nucleotide polymorphism. 404 illustrates a sequencing read in the left triplet that mismatches those of the group, and is filtered out. Filtering out sequencing reads that do not comprise an initially-identified single nucleotide polymorphism can filter out a sequencing error.

Module 405 can associate and assemble sequencing reads comprising identical polymorphisms at the same position into a partial digital representation of a candidate sequence. 405 can associate sequencing reads with chromosome numbers, chromosomal position of the polymorphism, name of the polymorphism, and a p-value for the association of the sequencing reads. 405 can additionally provide a graphic representation of the association of sequencing reads comprising identical polymorphisms, for example, within a Manhattan plot, a Q-Q plot, or any other suitable graphical representation. A module 406 can provide a local alignment of 405 to a reference sequence.

Module 407 can combine local alignments into larger candidate sequences, including complete candidate chromosomes, as illustrated as the long horizontal bars in 407. A statistical analysis can be used to determine which local alignments to combine. The analysis can involve determining the pattern of SNPs on each local alignment, and determining a statistical likelihood that different groups of SNPs exist on a common candidate sequence or chromosome. Non-limiting examples of sources of such statistical information include the number of barcodes shared across local alignments, the probabilities of sequencing errors on these barcodes, and the probabilities of sequencing errors on the reads used to infer SNPs. Module 408 can use similar statistical information or alignment data to suggest corrections to possible alignment errors made earlier in the process. 408 illustrates a correction being made by exchanging a sequencing read from one chromosome to the other based on the SNPs or lack thereof associated with those sequencing reads.

Module 409 can then identify that one of the candidate sequences corresponds to one haplotype or a diplotype, for example, the maternal haplotype, and the other candidate sequence corresponds to the other haplotype, such as the paternal haplotype. As illustrated in 409, all SNPs or lack thereof represented by dark dots are associated with one haplotype, and all SNPs or lack thereof associated with white dots are associated with the other haplotype. The system of FIG. 4 can distinguish one haplotype from the other based on the unique SNP patterns of the haplotypes, notwithstanding that the sequencing reads of one haplotype are otherwise identical to the sequencing reads of the other haplotype.

Figure 5:
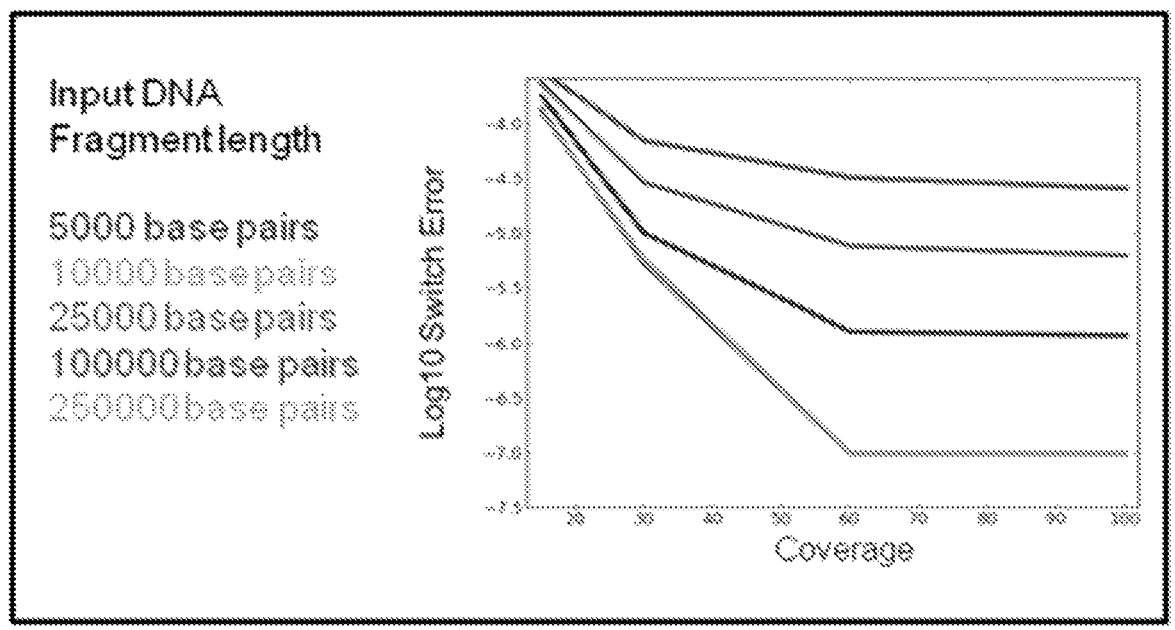
FIG. 5 is a graphic representation of error frequency based on a fragment length of input DNA.

FIG. 5 is a graphic representation of improvements in the error rate of switching sequencing reads between haplotypes as the size of DNA fragment length increases. Coverage is the average number of reads representing a given nucleotide in an assembly digital sequence. High coverage can reduce the error rate of assigning nucleotides and sequencing reads to haplotypes correctly.

Polymorphisms and Sequencing Errors.

Figure 6:
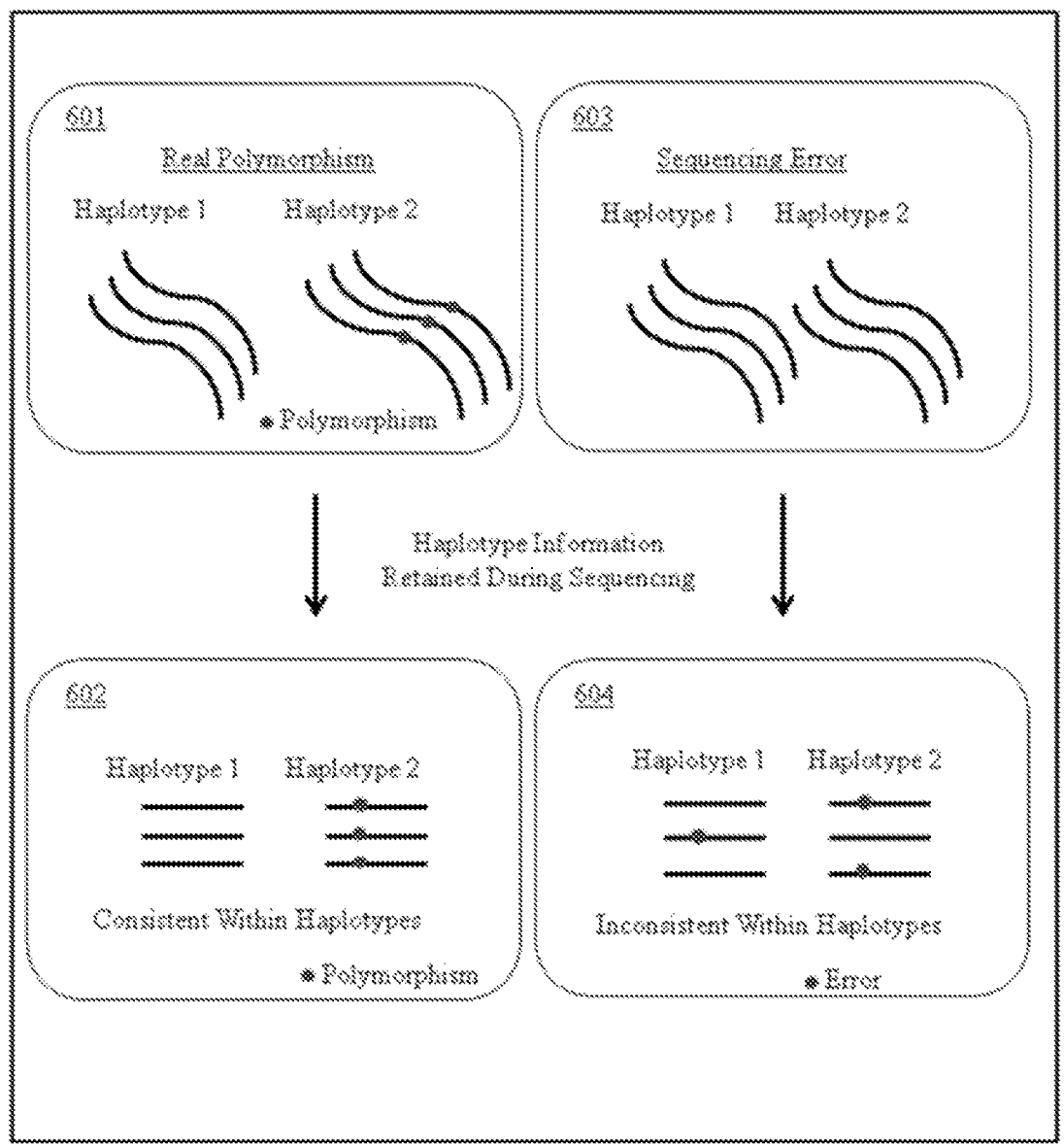
FIG. 6 illustrates a process that distinguishes a polymorphism from a sequencing error.

A method or a computer program product can distinguish single nucleotide polymorphisms from sequencing errors. FIG. 6 illustrates a process of variant correction utilizing haplotype phasing to distinguish a real mutation from sequencing errors. 601 represents a diploid sample wherein the haplotypes have already been distinguished by the process of FIG. 4. Haplotype 1 does not contain a mutation, but haplotype 2 does contain a SNP. Each haplotype is represented by a triplet of sequencing reads that overlap at the site of the SNP. 602 illustrates that as the sequencing reads are processed into candidate sequences, the SNP associated with haplotype 2 sequencing reads is unambiguously assigned to haplotype 2, and haplotype 1 does not show a SNP at that position.

The diploid sample of 603 does not possess a SNP on either haplotype, but does suffer from an error in sequencing. Each haploid is represented by a triplet of sequencing reads, none of which shows a SNP. 604 illustrates the outcome obtained in the event of a sequencing error. The error appears among the sequencing reads at random, and is not unambiguously associated with one of the haplotypes. This random distribution of the erroneous nucleic acid is clearly distinguishable from the scenario of 602, wherein the SNP is not distributed randomly among the sequencing reads of both haplotypes. Thus, when a putative SNP is identified in a sequencing assay, haploid phasing can verify the existence of a SNP instead of an error.

Translocations and Inversions.

Translocations and Inversions can lead to variability in the DNA, RNA, and protein constitution of a subject. Translocations have been identified as causes of cancers, infertility, and Down's syndrome. Translocations can occur naturally as reciprocal translocations between nonhomologous chromosomes. The invention provides computer program products and methods that identify previously known or unknown translocations and inversions within a set of sequencing reads of a sample.

In an analysis of a wild type genome, an individual barcode is ordinarily associated most prominently with one local region of the genome. Sequencing reads derived from physically-distant regions of a genome are less likely to share a common barcode. When barcoded sequencing reads are aligned to a reference genome, if remote portions of the reference genome are represented by sequencing reads that share a common barcode, then the possibility of a mutation, such as a translocation, can be investigated. A translocation in a sample would result in distant portions of a reference genome being proximate in a sample.

Figure 7:
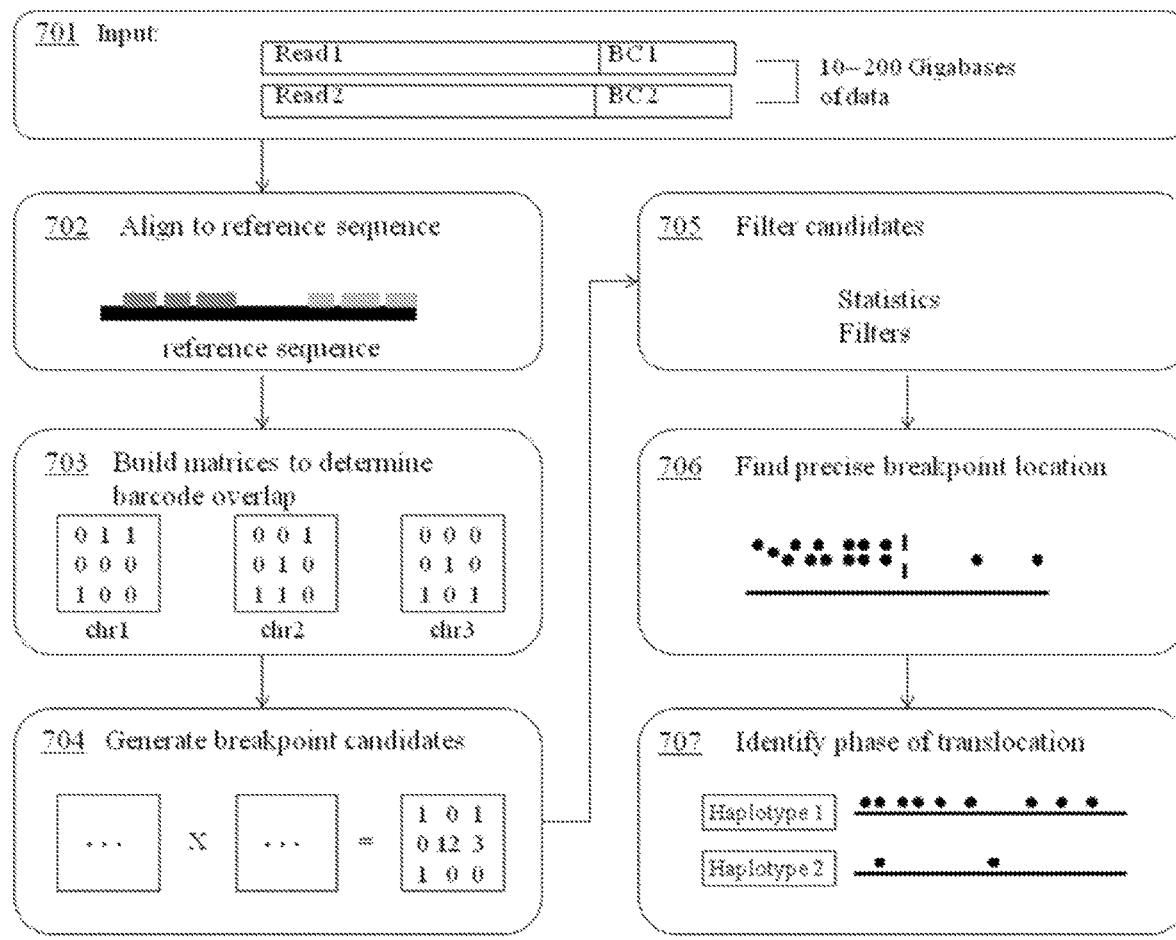
FIG. 7 is a graphic representation of an algorithm and example modules of a computer-program product that can identify a translocation.

FIG. 7 illustrates an algorithm and modules of a computer program product that can determine a translocation, thereby identifying distant regions of a genome that had been attached prior to translocation. 701 illustrates sequencing Read 1, which is associated with Barcode 1, and sequencing Read 2, which is associated with Barcode 2. 701 also illustrates the quantity of digital data associated with the sequencing reads, for example, 10-200 gigabases of data, which can be analyzed in real-time.

Module 702 aligns sequencing reads to a reference sequence, such as a reference chromosome or a reference genome, which can comprise multiple chromosomes. Each sequencing read independently comprises a barcode.

Module 703 represents barcodes distributed across three reference chromosomes (chr1, chr2, and chr3) in a reference genome. Each column of each matrix represents a region of each chromosome, and each row represents a specific barcode. The value at a point in a matrix indicates the number of times that the barcode was identified in the corresponding region of the chromosome. If regions have high numbers of barcodes in common, then those regions have a higher probability of being located close together in the sample, even if the regions appear far apart in the reference genome.

Module 704 processes matrices to identify candidate breakpoints. Matrices are multiplied, and the outcome can be scored to suggest a likelihood that a breakpoint exists on a certain reference chromosome in the reference genome. Module 705 then analyzes candidate breakpoints by p-value to determine which candidate breakpoints are most likely to be real.

Module 706 can identify the precise breakpoint in the reference genome leading to the translocation. Module 1006 aligns sequencing reads (dots) sharing a common barcode against a reference chromosome (horizontal bar) until a point is reached (vertical hash), beyond which sequencing reads possessing the common barcode no longer align with the reference chromosome. That point is the breakpoint of translocation. The breakpoint can be, for example, about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, or about 50 residues from a sequencing read that does align with the reference chromosome.

Module 707 can determine which haplotype in a pair of haplotypes is more likely to possess the translocation. Once the sequencing reads have been sorted by haplotype using the methods described herein, module 707 can determine which haplotype is more prominently associated with the translocation by determining which sequencing reads are associated with both the translocation and a particular haplotype.

Identifying Gained or Lost Copies.

Figure 8:
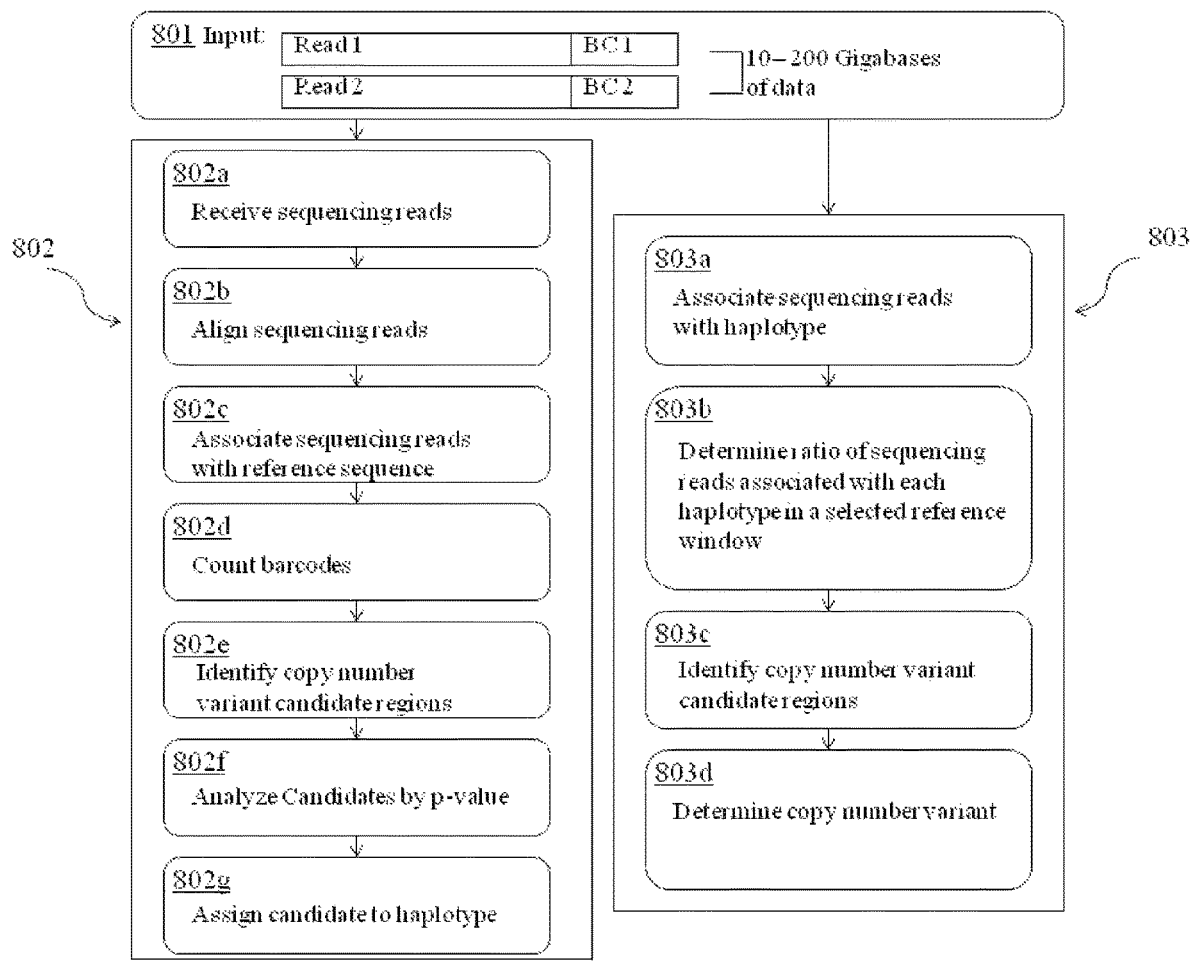
FIG. 8 is a visual representation of example modules of a computer program product that can identify regions of a genome that have gained or lost copies.

The methods disclosed herein can identify gained or lost copies of a residue, sequence, or fragment, for example, a nucleotide residue or an amino acid residue. FIG. 8 illustrates modules of computer program products that can identify a copy number variant within a sample. 801 illustrates example sequencing Read 1, which is associated with Barcode 1, and example sequencing Read 2, which is associated with Barcode 2. 1101 also illustrates that an input received from a first sequencing-read and a second sequencing-read can be associated with a quantity of digital data, for example, 10-200 gigabases of data, which can be analyzed in real-time. 802 and 803 illustrate alternative approaches for identifying copy number variants within a sample.

A system 802 can receive a first sequencing read and a second sequencing read. The first sequencing read and the second sequencing read can each be independently associated with barcodes, which can be identical or distinct. Module 802*a* can receive a plurality of sequencing reads, which can total in the hundreds, thousands, tens of thousands, or greater. Module 802*b* can align sequencing reads to a reference sequence and can further identify neighboring sequencing reads in the alignment, and determine whether the neighboring sequencing reads overlap at a non-barcode subsequence.

Module 802*c* can associate a set of sequencing reads comprising a common barcode to a region (a "window") of a reference sequence. The system can receive an additional sequencing read that does not comprise the common barcode, which can be filtered out by module 802*c*. Module 802*d* can count a number of distinct barcodes that have been associated with a region of a reference sequence. Module 802*e* can then identify candidate regions for a copy number variant based on the number of counted barcodes in a local region compared to global counts of the total number of barcodes in sample or in a region of the sample. If the number of barcode counts associated with a particular window is significantly greater than a statistical distribution, then the window can be designated as a candidate for a copy number mutation. The number of copies can be estimated based on the numbers of barcodes counted locally versus the numbers counted globally. Module 802*f* can filter the identified regions based, for example, on a p-value to determine which candidate windows are most likely to contain a real mutation. Module 802*g* can determine to which haplotype in a pair of haplotypes the copy number variant corresponds using a haplotype phasing algorithms provided herein.

In alternative 803, the system begins the analysis using phasing information associated with received sequencing reads. Module 803*a* phases a set of sequencing reads comprising barcodes by haplotype using methods described herein to provide two sets of sequencing reads: one associated with the first haplotype and the another associated with the second haplotype in a haplotype pair. Module 803*b* determines or approximates a ratio of received sequencing reads associated with the first haplotype and received sequencing reads associated with the second haplotype within a window of a reference sequence. Module 803*c* can identify candidate copy number variant regions based on a comparison of the number of barcodes within the window associated with one haplotype versus the other. For example, a ratio of barcodes associated with each haplotype that significantly deviates from a statistical expectation can suggest the presence of a copy number variant on a haplotype, and can provide an estimation of the number of copies. Module 803*d* can filter the identified regions based, for example, on a p-value to determine which candidate windows are most likely to contain a real mutation.

A module can be programmed to execute any useful statistical calculation to determine, for example, the statistical significance of data suggesting a polymorphism, a copy number variant, a translocation, or an inversion, or the statistical likelihood of the existence of any of the foregoing. Non limiting example of a statistical analysis that can be performed include: a) analysis of variance (ANOVA); b) chi-squared test; c) factor analysis; d) Mann-Whitney U analysis; e) mean square weighted deviation (MSWD); f) Pearson product-moment correlation coefficient; g) regression analysis; h) Spearman's rank correlation coefficient; i) Student's t-test; j) time series analysis; and k) p-value analysis.

Assembling Sequencing Reads.

Figure 9:
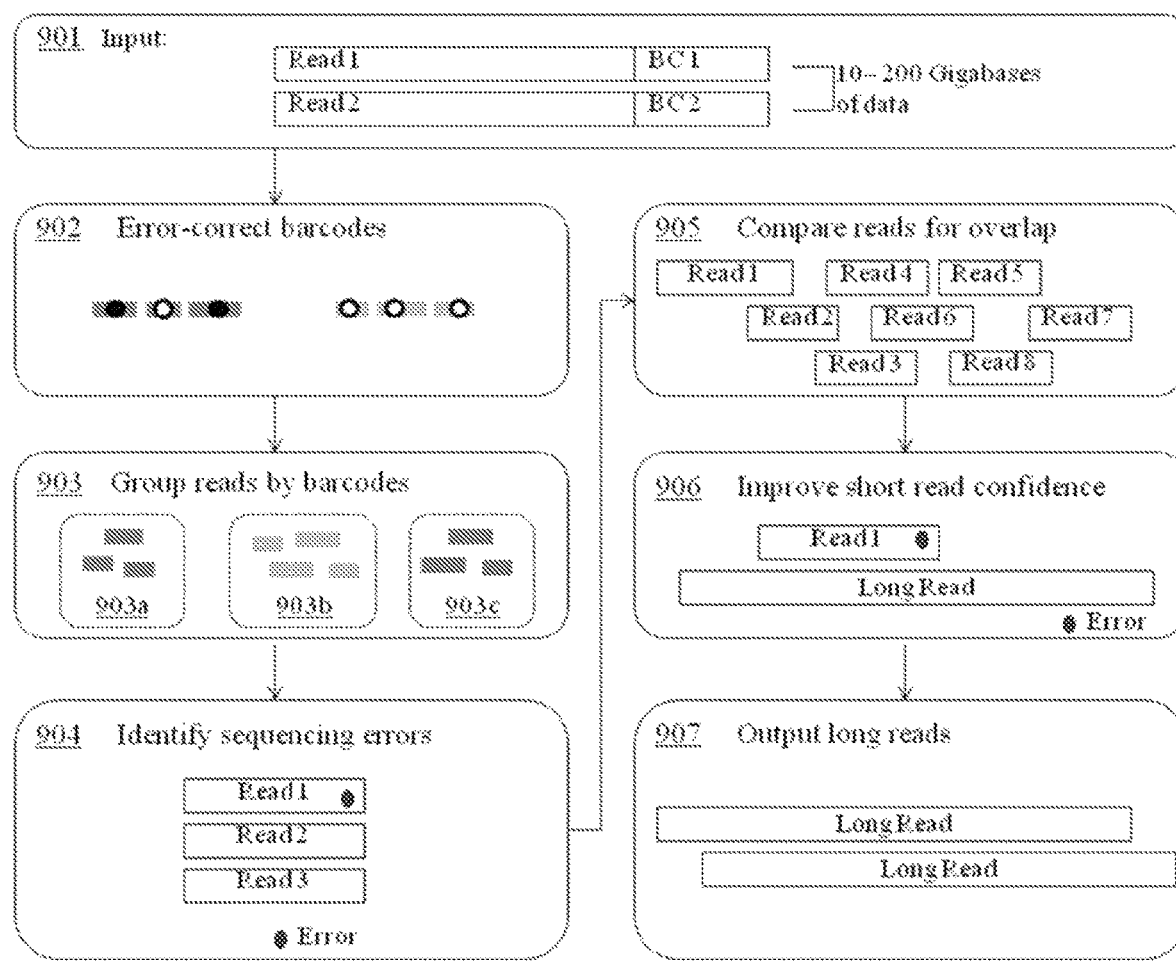
FIG. 9 is a visual representation of example modules of a computer program product that can provide a digital representation of a sequence of a sample based on an assembly of short sequencing-reads into long sequencing reads.

A challenge in the analysis of sequencing data is to assemble short sequencing reads obtained experimentally into a longer digital representation of the sample unambiguously. Longer sequencing reads can provide faster and more reliable processing, a lower error rate, and a greater confidence level in alignments and construction of candidate sequences. FIG. 9 illustrates modules that can be coded within an assembly algorithm that assembles short sequencing reads into long sequencing reads. 901 illustrates sequencing Read 1, which is associated with Barcode 1, and sequencing Read 2, which is associated with Barcode 2. 901 also illustrates that an input received can be associated with a quantity of digital data, for example, 10-200 gigabases of data, which can be analyzed in real-time.

Module 902 identifies barcodes in received sequencing reads and searches for errors in the barcode reads. An error in reading a barcode ordinarily produces a sequence that deviates from a barcode only slightly, or has a high degree of homology with a real barcode, such as about 80%, about 85%, about 90%, about 95%, or about 97% homology with a real barcode. Errors in reading barcodes can also be identified by a count of the number of identical barcodes received. A particular barcode error should be received in much lower frequency that a real barcode. Thus, a barcode observed with a frequency that is statistically low and possesses high homology with another barcode that is received in much higher quantity is most likely an error in reading the other barcode.

Module 902 corrects the error in the erroneous barcode so the corresponding sequencing read can be processed correctly. 902 illustrates two triplets of sequencing reads. The right triplet shares a common barcode represented by a white dot. The left triplet shares a common barcode represented by a black dot; however, one sequencing read possesses the wrong barcode. 902 finds and corrects this error.

Module 903 then groups sequencing reads based on barcodes associated with the sequencing reads. 903 illustrates three groups, A, B, and C, of sequencing reads obtained from a source. All sequencing reads in a group share a barcode in common with the other sequencing reads in the same group, but do not share a barcode in common with any other group. For example, all sequencing reads in Group A are associated with barcode A exclusively, all sequencing reads in Group B are associated with barcode B exclusively, and all sequencing reads in Group C are associated with barcode C exclusively.

Once the sequencing reads have been grouped, module 904 identifies sequencing errors in the sequencing reads. Errors can be identified based on the frequency of certain subsequences occurring among sequencing reads of the same group. The confidence that a subsequence is correct increases as the number of sequencing reads containing the subsequence increases. However, a small number of sequencing reads can possess a subsequence that differs in a small number of residues from another subsequence that has been identified with a higher confidence level. The deviant subsequence can be identified as a sequence error and corrected to match the subsequence obtained at a higher confidence level.

Module 905 can compare short sequencing reads for overlapping subsequences. Multiple overlaps can be found, and the greatest statistical significance and confidence is assigned to long overlaps that are observed over the greatest number of sequencing reads. As high-confidence overlaps are found, the smaller sequencing reads can be assembled into increasingly larger sequencing reads.

As the process continues, non-overlapping sequencing reads are eventually joined. For example, if a first sequencing read overlaps with a second sequencing read, but not with a third, and the second sequencing read does overlap with the third, module 905 can determine a candidate sequence organizing the first, second, and third sequencing reads into a single longer sequence.

Once longer sequencing reads have been generated, module 906 can improve data obtained from shorter sequencing reads by comparison of short sequencing reads with the longer sequencing reads. A short sequencing read can be aligned against a longer sequencing read that spans greater than the length of the short sequencing read. A high degree of homology in the alignment suggests with high confidence that both sequencing reads correspond to the same region of the sample. If the sequencing reads differ only slightly, such as in a single residue, module 906 can correct the short sequencing read to match the longer sequencing read because the longer sequencing read, being assembled from several barcoded sequencing reads, has a higher likelihood of being accurate. Module 907 can then output the long sequencing reads for use in development of candidate sequences.

Identifying Sequencing Reads Originating from a Common Source.

Figure 10:
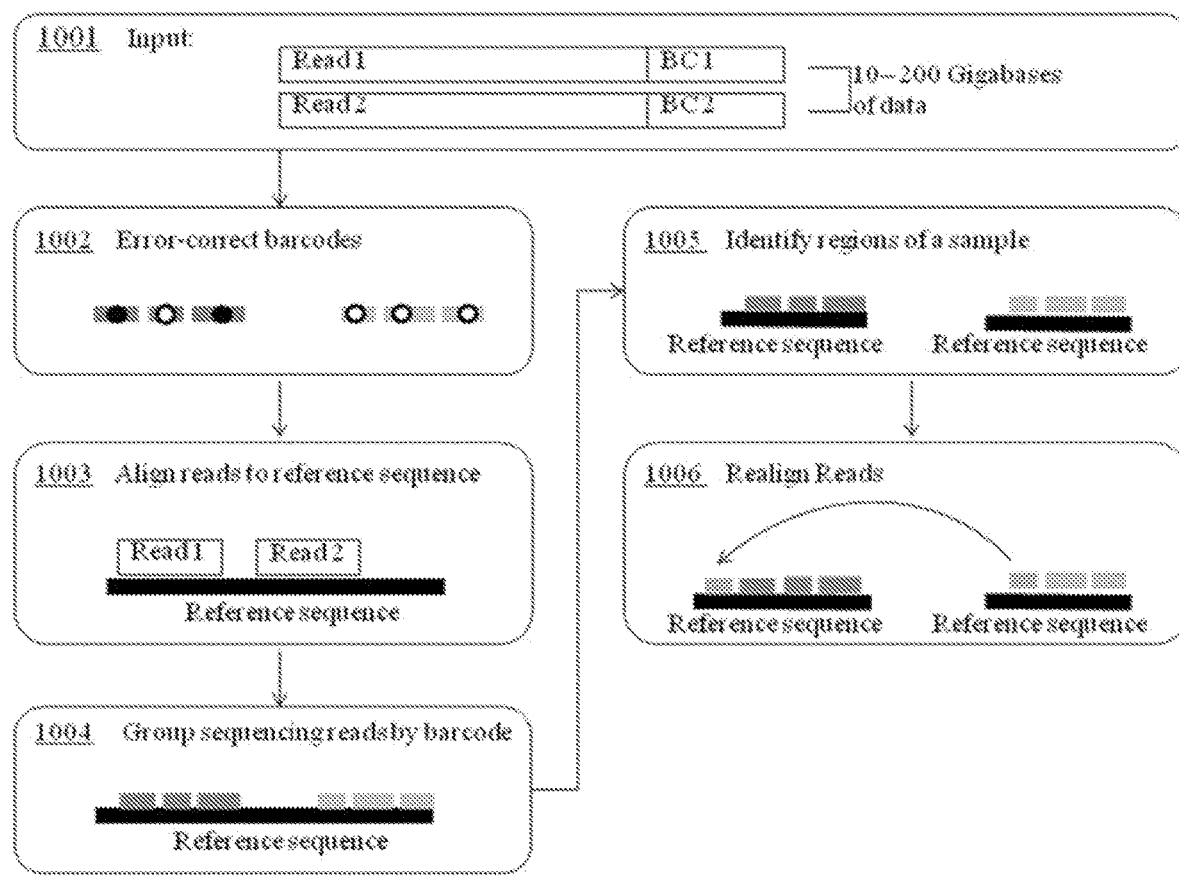
FIG. 10 is a visual representation of example modules of a computer program product that identifies sequencing reads originated from the same starting piece of DNA.

FIG. 10 is a visual representation of modules that can be encoded in an algorithm that identifies sequencing reads associated with a common biomolecule, such as a nucleic acid. 1001 illustrates sequencing Read 1, which is associated with Barcode 1, and sequencing Read 2, which is associated with Barcode 2. 1001 also illustrates that a sequencing read input received can be associated with a quantity of digital data, for example, 10-200 gigabases of data, which can be analyzed in real-time.

As sequencing reads are received and barcodes are recognized, module 1002 can correct errors in barcodes using methods described herein. The left triplet shown in 1002 illustrates a set of sequencing reads that have a mismatched barcode (white center). The right triplet shown in 1002 illustrates a set of sequencing reads that have properly matched barcodes. Module 1003 can then align sequencing reads to a reference, such as a reference genome. Module 1004 then groups sequencing reads within the alignment based on barcodes associated with each sequencing read, to provide groups of sequencing reads wherein each member of a group shares a common barcode. 1004 illustrates two such groups of barcoded sequencing reads aligned against the same reference genome, wherein both groups share the same common barcode.

Module 1005 can analyze the alignments to identify local regions of a sample. Overlapping sequencing reads sharing a common barcode that together provide a consensus region of a biomolecule represent a local region, and can be distinguished from another group of barcoded sequencing reads, which together provide a separate consensus region. As illustrated in 1004, both groups of sequencing reads share the same common barcode, and this commonality can suggest that both groups of sequencing reads represent local regions of a biomolecule that are spatially close. Very close regions can be physically contiguous in the sample.

Once close, or contiguous, regions have been identified, module 1006 can realign the sequencing reads to improve the quality of the alignment. When the local regions are contiguous, an individual sequencing read can potentially be aligned with one subregion that provides an alignment less accurate than that possible with another subregion. Dividing the barcoded group into distinguishable contiguous local regions provides a second opportunity to reexamine the alignments, and when necessary, transfer a sequencing read from one subregion to another contiguous subregion to provide a more optimal alignment, as illustrated in 1006.

Assembling Short Sequencing Reads into a Digital Representation of a Sample.

Figure 11:
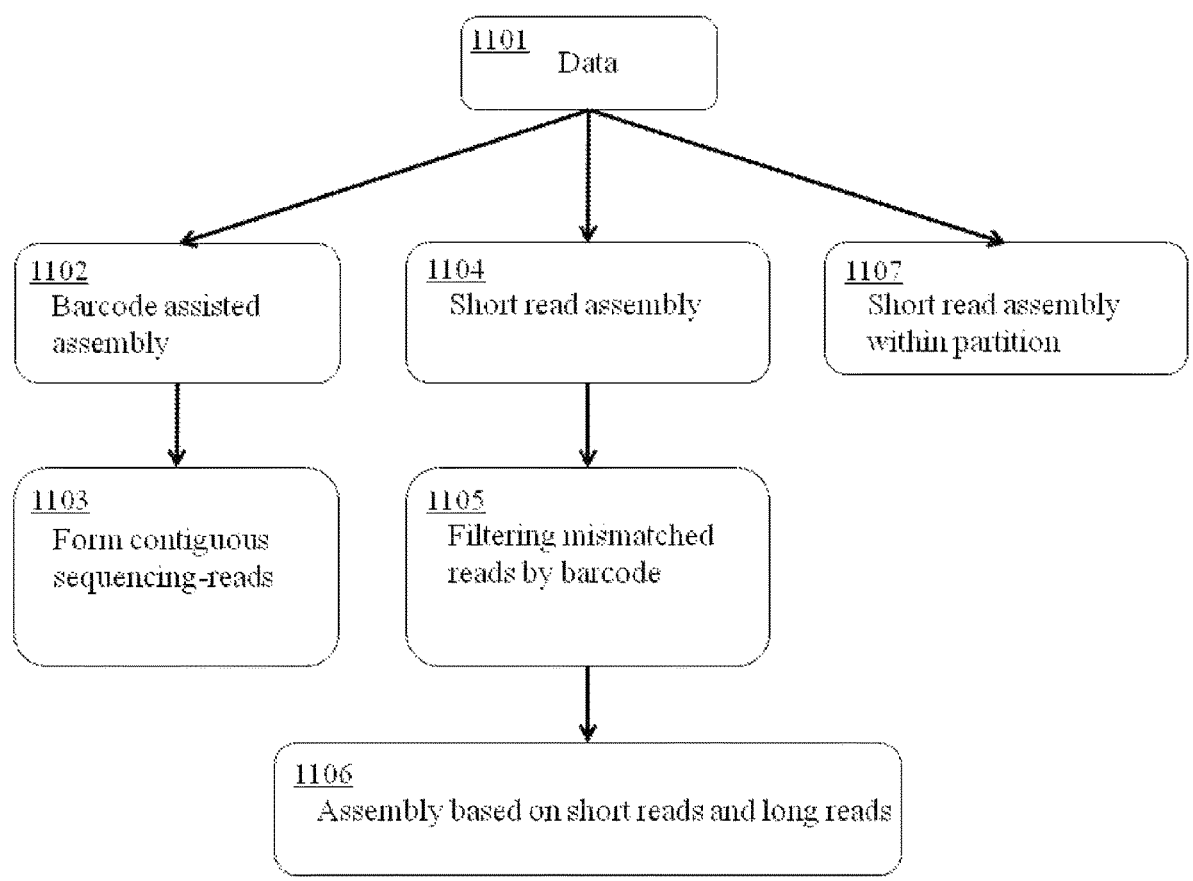
FIG. 11 is a diagram illustrating multiple possible approaches to an assembly of sequencing reads.

Assembling short sequencing reads into longer contiguous and overlapping sequences suitable for generating candidate sequences is an expensive and time-consuming aspect of sequencing data interpretation. FIG. 11 provides an overview of multiple approaches to a high-level assembly of short sequencing reads into long sequencing reads, made more rapid and efficient by the processes provided herein. Sequencing data 1101 can comprise short sequencing reads associated with barcodes. One approach 1102 is to assemble short sequencing reads comprising identical barcodes into contiguous sequences, and to infer a consensus sequence of overlapping residues based on sequence overlaps. A second approach 1103 is to form a scaffold of contiguous sequencing reads based on an overlap of the sequencing reads and partial/global alignment to a reference genome. The short sequencing reads assembled in 1103 can comprise barcodes, and a barcode can be used as described herein to resolve alignment ambiguities. A third approach is to assemble short barcoded sequencing reads based on alignment 1104 of the short sequencing reads, filtering 1105 of mismatched sequencing reads based on the barcodes, and assembly 1106 of candidate sequences using both long reads and the filtered short reads. A fourth approach 1107 is identification of a group of short sequencing reads based on an understanding of the origin of the sequencing reads within a sequencer apparatus. Such an approach can efficiently assemble a set of overlapping short sequencing reads into longer sequences, and the short and long sequencing reads can be used together. Alternatively, process 1106 can be used directly without first aligning and filtering the short sequencing reads. All approaches are accessible via real-time processing.

Figure 12:
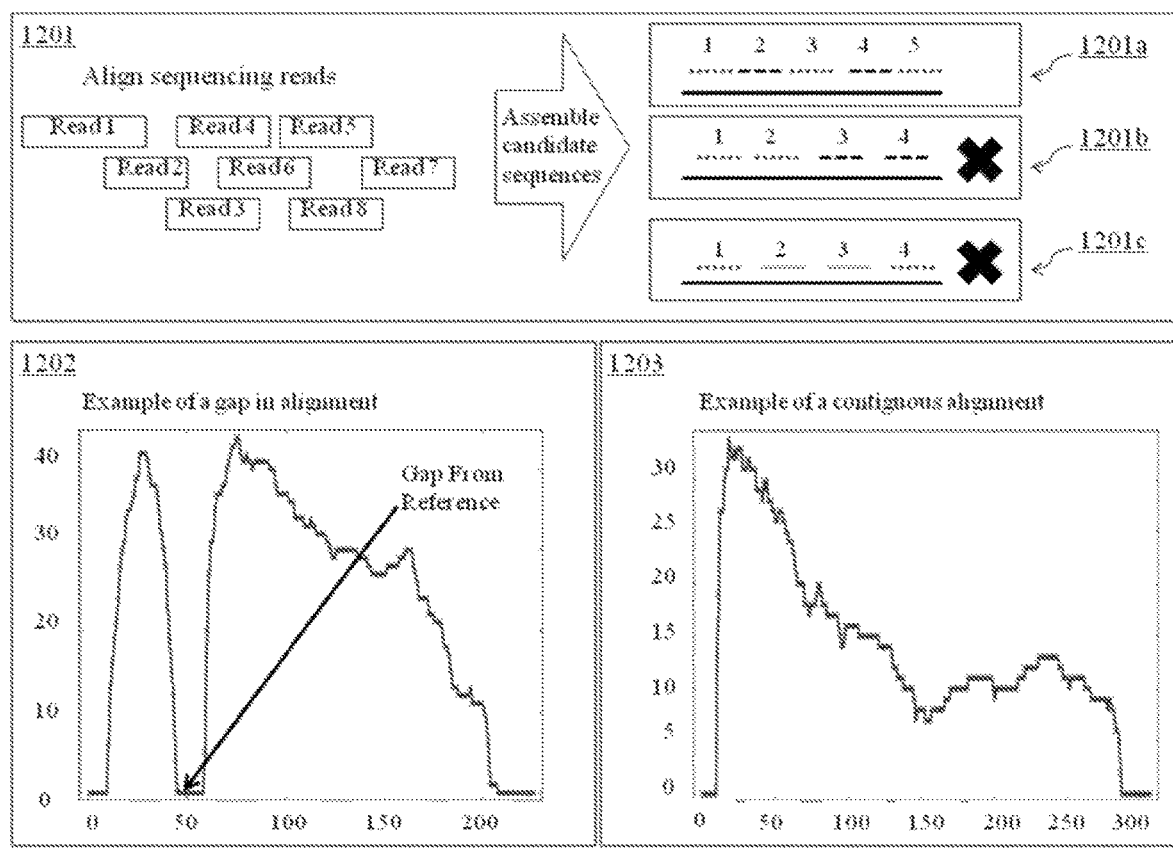
FIG. 12 illustrates a method of filtering continuous sequences with barcodes.

FIG. 12 illustrates advantages of barcode-assisted assembly of a sequencing read. Pane 1201 illustrates the assembly of a candidate sequence from sequencing reads, and a selection of the best candidate sequence based on barcode analysis. 1201a illustrates a candidate sequence derived from five sequencing reads, 1, 2, 3, 4, and 5, each of which corresponds to either barcode 1 (dashed) or barcode 2 (dotted). The pattern of barcodes 1 and 2 on the candidate sequence suggests that the sequencing reads associated with both barcodes originate from the same local region of the sample because both barcodes appear in overlapping series. Thus, the data obtained from the sequencing reads associated with barcode for barcode 2 mutually reinforce one another and add confidence to the candidate sequence of 1201a.

1201b illustrates a candidate sequence derived from four sequencing-reads, 1, 2, 3, and 4, each of which corresponds to either barcode 1 or barcode 2. The alignment of 1201b indicates that sequencing reads 1 and 2 are likely to correspond to proximate regions in a sample, and sequencing reads 3 and 4 are likely to correspond to proximate regions in a sample. However, since no overlap is observed between sequencing reads of differing barcodes, the data obtained from barcodes 1 and 2 do not reinforce one another. The analysis cannot ascertain unambiguously whether the alignment illustrated in 1201b corresponds to a contiguous set of overlapping sequences or to remote regions of the sample.

1201c illustrates a candidate sequence derived from four sequencing reads, 1, 2, 3, and 4, each of which corresponds to either barcode 1 or barcode 2. The alignment of 1201c indicates that sequencing reads 3 and 4 are likely to correspond to proximate regions in a sample, but cannot provide an unambiguous relationship between sequencing reads 1 and 4. Since no overlap is observed between the alignments of 1201c sequencing reads of differing barcodes, the data obtained from barcodes 1 and 2 do not reinforce one another. The analysis cannot ascertain unambiguously whether the alignment illustrated in 1201c corresponds to a contiguous set of overlapping sequences or to remote regions of the sample. Of the three alignments, 1201a offers the highest confidence option for constructing an accurate candidate sequence.

Panels 1202 and 1203 provide graphic representations of outputs of sequencing alignments against a reference sequence. Both graphs indicate the numbering of residues in the reference sequence on the x-axis, and, on the y-axis, the number of sequencing reads detected that correspond to the value of the x-axis.

1202 illustrates a negative spike around x=50, reaching down to y=0, over a span of residues of the reference sequence. This spike indicates a gap in the alignment between the sequencing reads and the reference sequence, a region of the reference sequence to which none of the sequencing reads correspond. The alignment producing this graph is unlikely to represent the sample accurately.

1203 illustrates a plot of a more accurate alignment. Each residue of the reference sequence is represented in multiple sequencing reads. The alignment producing this graph is more likely to represent the sample accurately.

Figure 13:
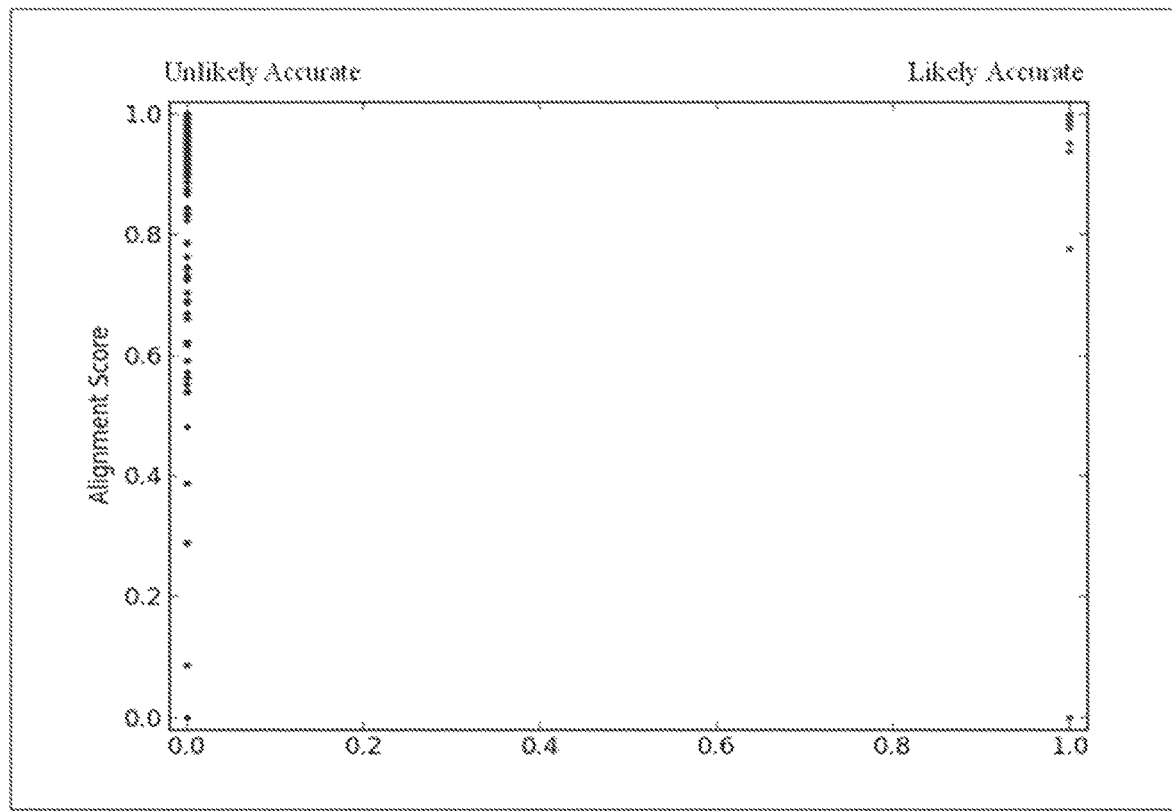
FIG. 13 is a graphical representation of a plot of alignment scores.

FIG. 13 illustrates a plot scoring alignments generated by the methods described herein. A quality control module can generate a score for an alignment based on numerous factors such as percentage of reference residues represented and number of time represented, degree of sequencing read overlap, percentage of duplicates, number of errors, and numbers and ratios of barcodes detected. In FIG. 13, an alignment producing the results of 1202 would be scored low, and would be grouped "Unlikely Accurate". An alignment producing the results of 1203 would be scored high, and would be grouped "Likely Accurate".

Figure 14:
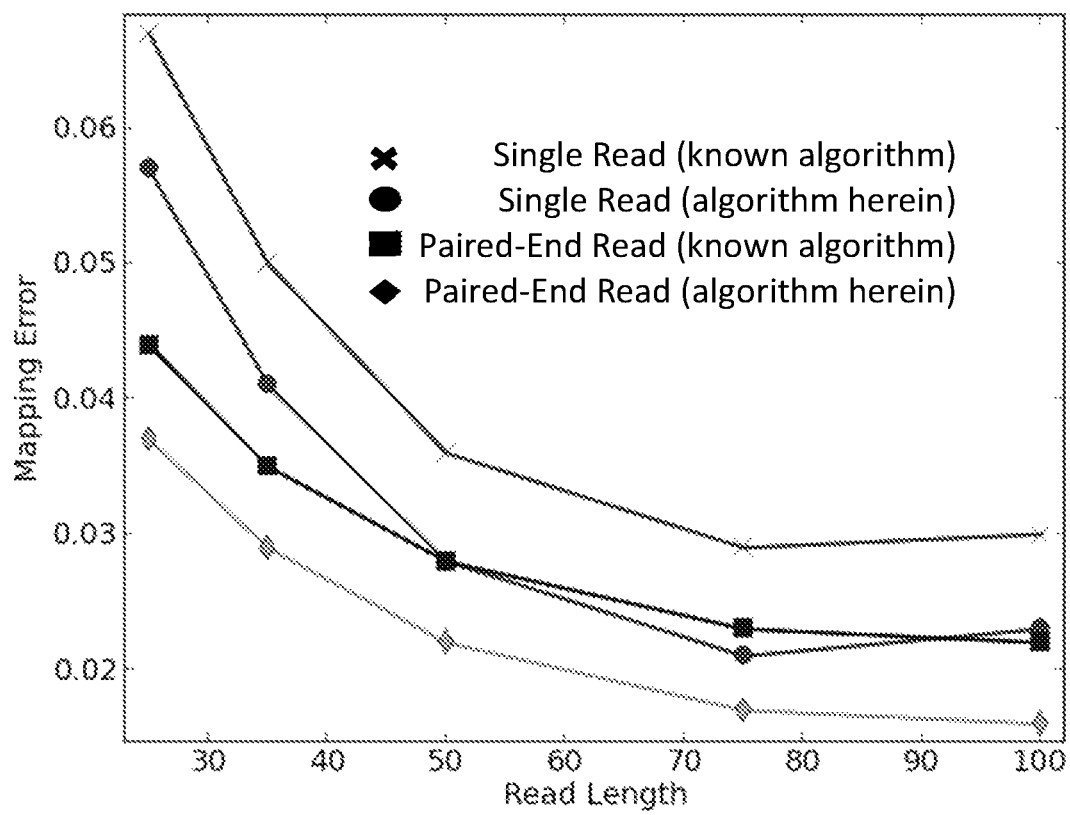
FIG. 14 is an overview of a method utilizing barcodes to improve alignments.

FIG. 14 illustrates simulated results of barcode-assisted alignments as a function of sequencing-read length and mapping error. Simulations were performed for both known sequencing analysis algorithms and for algorithms disclosed herein, using single barcode per read and paired-end barcodes per read systems. The plots indicate that in both cases of single or paired barcodes, the algorithms of the invention produce lower error rates at every read length investigated.

RNA Sequencing Algorithms.

Alternative splicing events, which can be common in eukaryotic RNA, pose challenges to the identification of distinct splicing variants with sequencing technologies. The invention provides an effective and accurate method to resolve ambiguities present in sequencing reads generated with RNA sequencing technologies. Non-limiting examples of classes of RNAs that can be analyzed with a method herein include: messenger RNAs (mRNAs), transfer RNAs (tRNAs), ribosomal RNAs (rRNAs), small nuclear RNAs (snRNAs), small interfering RNAs (siRNAs), piwi-interacting (piRNAs), non-coding RNAs (ncRNAs), long non-coding RNAs, (lncRNAs), and fragments of any of the foregoing.

Figure 15:
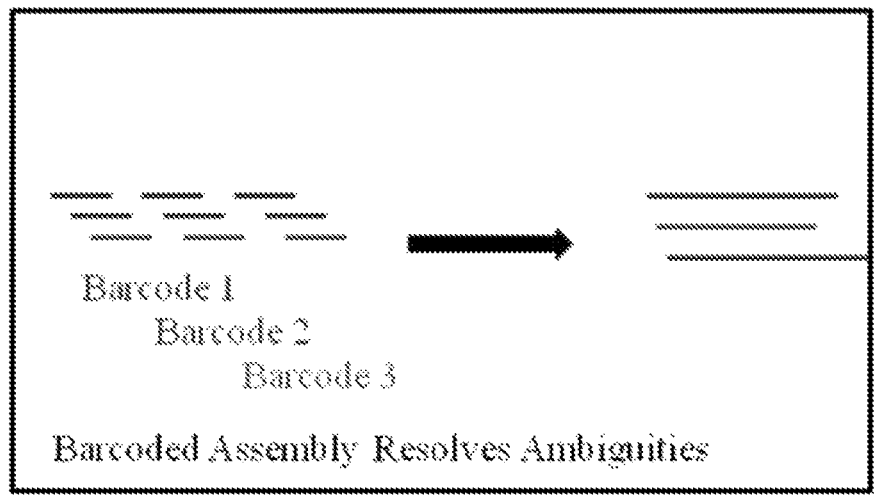
FIG. 15 is an illustration of a barcode-assisted assembly of RNA transcripts.
Figure 15:
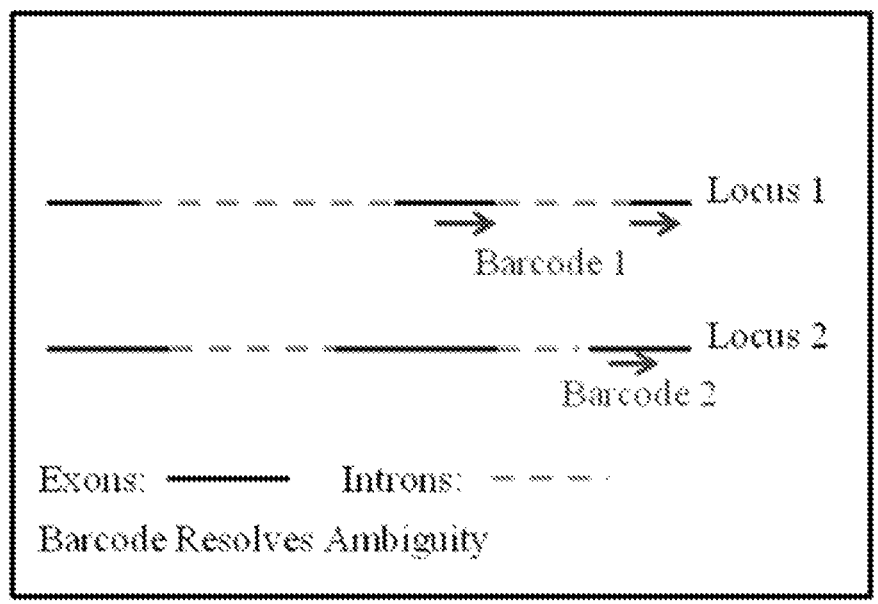

The methods herein of analyzing sequencing data solve challenges in analyzing RNA sequencing data associated with genes that are alternatively spliced. FIG. 15 illustrates a process wherein an association of a specific barcode with individual transcripts unambiguously identifies each transcript, whether the transcript contains alternatively spliced exons or not.

In 1501, each barcode is associated with a distinct transcript. For example, a translocation frequently identified in prostate cancer can include fusions of the TMPRSS2 gene, and the ETS transcription factor gene ERG to generate TMPRSS2-ERG translocations. The presence of an identical barcode in a transcript comprising a fragment of the TMPRSS2 gene and a fragment of the ERG gene can designate the presence of a TMPRSS2-ERG translocation in a sample.

1502 illustrates a method wherein an association of a barcode with a particular locus can indicate the locus of origin of a transcript. For example, a mutation within the first exon of the Adenomatous polyposis coli (APC) gene of a human subject can be associated with a 95% likelihood of the subject developing familial adenomatous polyposis (FAP). A method of the invention can associate an RNA transcript with a haplotype, thereby unambiguously identifying the entirety of the transcript comprising the mutation.

Figure 16:
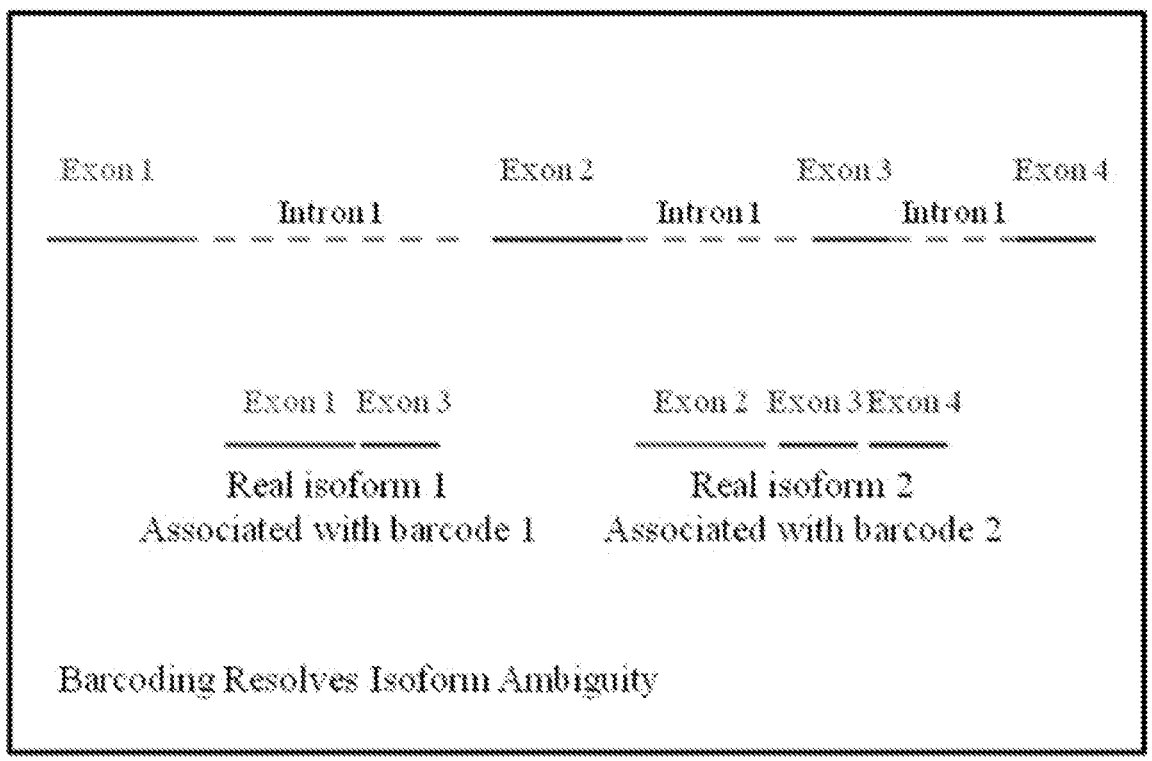
FIG. 16 is an illustration of a barcode-assisted assembly of RNA transcripts applied to resolving ambiguities in assembling sequencing-reads of distinct RNA isoforms.

Another challenge presented by RNA sequencing analysis is the reconstruction of short sequencing reads into correct isoforms. FIG. 16 illustrates a barcode-assisted assembly of RNA transcripts applied to resolving ambiguities in assembling sequencing reads of distinct RNA isoforms. The association of identical barcodes to different RNA isoforms provides an effective method to resolve ambiguities in assembling short sequencing-reads generated in RNA sequencing.

Visual Output.

The methods and computer program products provided herein can output information associated with a sequencing assay in real-time as an assay runs. Output information can include sequencing parameters, data, sequencing reads, candidate sequences, alignments, comparisons, mutations, errors, reference sequences used, and information associated with the assay instrument, user, or client. A system can track assays occurring on multiple instruments simultaneously and identify the instruments being used by make, model, serial number, owner, or user. In doing so, the output module can provide information about the end users and their preferences and parameters. A visual output can track the construction of multiple candidate sequences simultaneously, and display multiple candidate chromosomes simultaneously for comparison.

A user of the output system can monitor progress of an analysis, and can interact with information during the analysis, either in static or real time, and upon conclusion of an analysis. The user can make notations in the interface, such as posting comments on an analysis and flagging points of interest, such as potential errors. The user can obtain information from the interface, including data, data processing results, and information describing an instrument, computer, client, facility, sample, or subject associated with the sequencing data.

Figure 17:
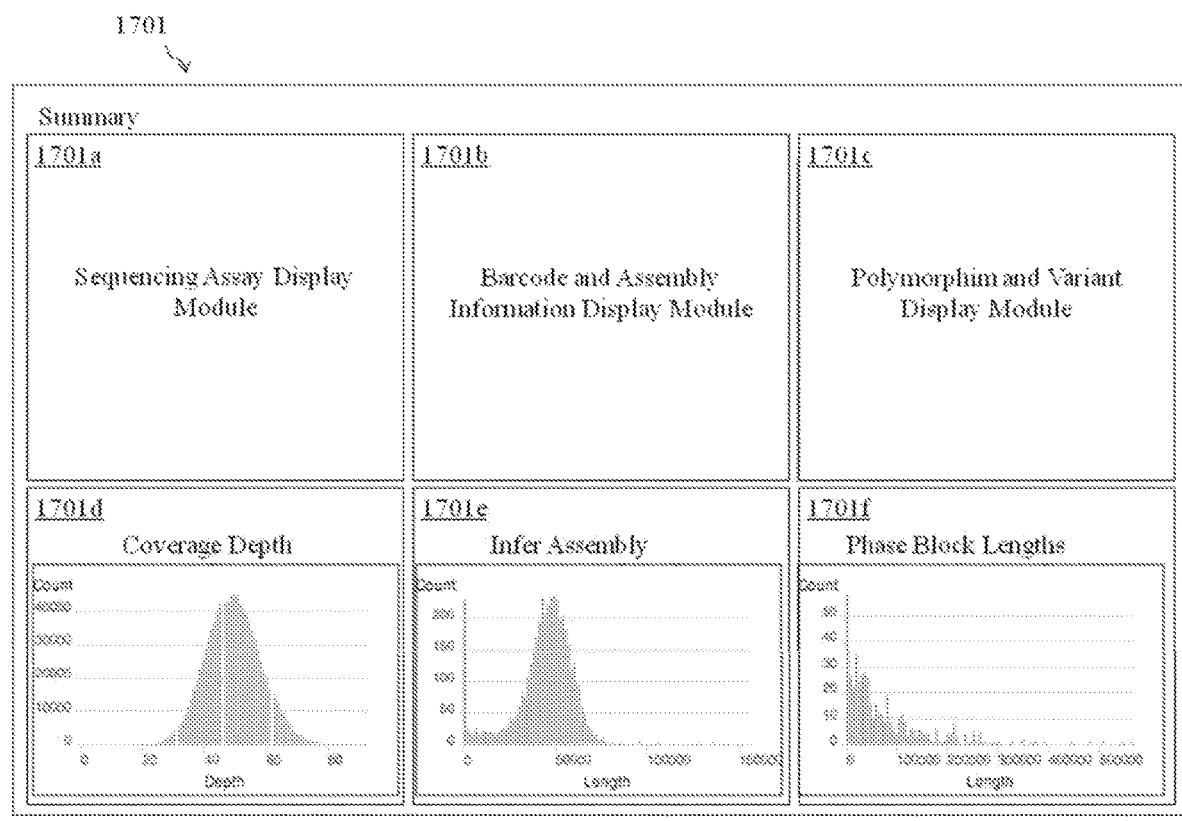
FIG. 17 illustrates a representative visual display of a data visualization/interface.

FIG. 17 is illustrates visual outputs. 1701 illustrates a visual display outputting data in real-time. 1701a illustrates a screen that displays sequencing assay parameters processed in real-time. Example output parameters include: a) median depth of sequencing; b) standard-deviation of depth of sequencing; c) total number of sequencing-reads received; d) percentage of pair aligned reads; e) percentage of single aligned reads; f) percentage of pair unaligned reads; g) percentage of zero coverage; h) percentage low coverage; i) mean insert size; and j) standard deviation of the insert size.

Display module 1701b illustrates displays parameters associated with barcode and sequencing read assembly in real-time. Examples of display information include: a) a total number of unique barcodes; b) percentage of barcodes with errors; c) final number of unique barcodes; d) mean reads per barcode; e) percentage of reads that are realigned; f) mean inferred contiguous sequence length; g) percentage of inferred contiguous sequences smaller than a threshold size; h) number of inferred contiguous sequences; i) mean or maximum contiguous sequence length per barcode; and j) standard deviation of contiguous sequence per barcode. Display module 1701c displays parameters associated with polymorphisms in real-time. Example parameters include: a) number of single nucleotide polymorphisms identified; b) number of INDELs identified; c) rate of identifying homozygous polymorphisms; d) number of translocations identified; e) number of translocations associated with a haplotype; f) % single nucleotide polymorphisms associated with a haplotype; and g) rate of INDELS associated with a haplotype.

The output modules can display graphical representations of the parameters above. 1701d illustrates a graphical representation of a coverage depth of sequencing. 1701e illustrates a graphical representation of an inferred assembly of a set of sequencing reads. 1701f illustrates a graphical representation of the length of a phase block.

Data Storage.

Output data from a sequencing experiment, and output results from data analysis, can be stored electronically in data archives. Any information described herein can be stored in a data archive, and specific information can be stored in files configured to contain or reference any barcodes associated with the information. A record can contain, for example, information associated with a variant that was identified in data analysis. Such information can include the identifying features of the variant, such as the chromosome bearing the variant, the position on the chromosome, and the identities of the nucleobases varied from a reference, for example, replacing adenosine with cytidine.

The record can contain the identities or sequences of any sequencing read associated with the variant. The record can further contain any barcode associated with the variant or associated sequencing reads. The inclusion of the barcodes in the records provides access to any information derivable from the barcodes, such as the error probability associated with the variant, and haplotype phasing.

The incorporation or association of barcodes with the records describing the variants allows for significant improvements in the efficiency of data analysis and manipulation. A user has access to the relevant barcodes without the need to search the raw data to find the barcodes associated with the variant. If further data analysis is done at a later time, the analysis can begin directly from the record rather than having to redo the initial data analysis. The avoidance of reanalyzing barcode/variant correlations established previously saves time and cost, and facilitates the performance of multiple successive analyses from the same data batch. Also, a user can focus subsequent data analysis on precisely the barcodes, or sequencing reads associated therewith, relevant to the variant of interest without the need to process all other barcodes associated with the original sample material. The data storage system promotes multiple bioinformatic applications, such as variant phasing, single-cell analysis, and metagenomics by using the barcodes to identify the place of origin of a variant.

Figure 21:
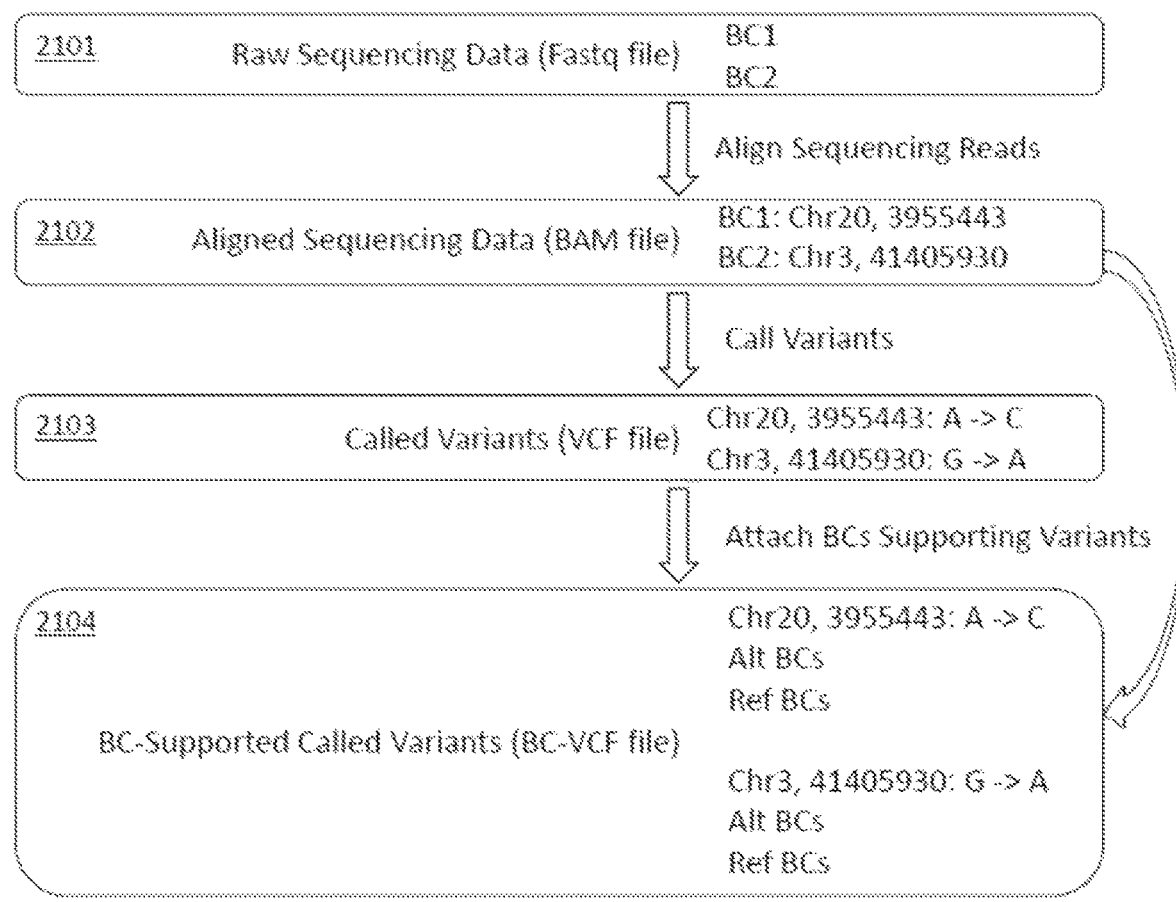
FIG. 21 illustrates a process for creating records in which variants identified in data analysis can be co-recorded with the barcodes used to identify the variant.

FIG. 21 illustrates a non-limiting example of the record system. 2101 illustrates obtaining the raw sequencing data in the form of a Fastq file. The Fastq file can contain many barcodes associated with a sequencing experiment. Alignment of the sequencing reads provides aligned data, which can be stored in a BAM file (2102). The barcodes can be associated with variants in the aligned data, and can identify the variant by location. 2102 shows that barcode 1 is associated with a variant at position 3,955,443 on chromosome 20, and barcode 2 is associated with a variant at position 41,405,930 on chromosome 3. In 2103, the variants have been called and recorded in a VCF file. The VCF file identifies the differences between the sequencing data and a reference. Position 3,955,443 on chromosome 20 of the sample has a cytidine residue, whereas the reference has an adenosine residue, and position 41,405,930 on chromosome 3 of the sample has an adenosine residue whereas the reference has a guanosine residue. Once the variants are identified, the record can be elaborated (through use of the bam file (2102)) with the identities of all barcodes that support the variant call, including barcodes supporting the called variant and barcodes supporting the reference allele (2104).

Generating and Analyzing DNA/RNA Sequencing Reads.

Sequencing experiments can be done individually or in parallel to provide tens, hundreds, or thousands of sequences simultaneously. In addition to identifying standard nucleotides and amino acids, methods herein can identify natural and non-natural modifications within a sample, for example, methylation of the cytosine base to produce 5-methylcytosine. In some embodiments, a sample comprises modifications within traditional base pairs, such as hypoxanthine, or xanthine, which can be purine derivatives. In some embodiments, a sample can include natural and non-natural RNA derivatives, such as Inosine (I), and modifications such as 2'-O-methylribose modifications.

A computer program products and methods herein can analyze data generated by any sequencing instrument. Non-limiting examples of sequencers include: a) DNA sequencers produced by Illumina™, for example, HiSeq™, HiScanSQ™, Genome Analyzer GAIIX™, and MiSeq™ models; b) DNA sequencers produced by Life Technologies™, for example, DNA sequencers under the AB Applied Biosystems™ and/or Ion Torrent™ brands; c) DNA sequencers manufactured by Beckman Coulter™; d) DNA sequencers manufactured by 454 Life Sciences™; and e) DNA sequencers manufactured by Pacific Biosciences™.

Methods of the invention can analyze data obtained in a variety of sequencing experiments. For example, sequencing-by-synthesis technology uses a unique fluorescent-label for each of adenine, cytidine, guanine, and thymidine. A nucleotide chain is synthesized based on a sample sequence, and during each sequencing cycle, a single labeled deoxynucleoside triphosphate (dNTP) is added to the nucleic acid chain. The nucleotide label terminates polymerization. After each dNTP incorporation, the fluorescent dye is irradiated to identify the newly-added residue and then the label is enzymatically cleaved to allow incorporation of the next nucleotide.

Semiconductor sequencing technology is based on the premise that when a nucleotide is incorporated into a strand of DNA by a polymerase, a hydrogen ion is released as a byproduct. A sequence is synthesized based on a template sample sequence. Each of adenine, cytidine, guanine, and thymidine is added sequentially. If one of the nucleotides is incorporated into the growing chain, the charge from the released hydrogen ion changes the pH of the reaction solution. A solid-state pH meter detects the pH change, thereby identifying the chain elongation. If a nucleotide is not incorporated, no voltage change will be recorded by the solid-state pH meter and no information will be incorporated into a sequencing read. A pattern of released hydrogen ions can provide the information needed to construct a sequencing read.

Samples.

A sequencing read can be generated from various samples. A sample can be derived from a variety of biological sources, such as blood, saliva, tissue, or a biopsy. A sequence of a sample can comprise information associated with a variety of biomolecules. Non-limiting examples of biomolecules include amino acids, peptides, peptide-mimetics, proteins, recombinant proteins, antibodies (monoclonal or polyclonal), antibody fragments, antigens, epitopes, carbohydrates, lipids, fatty acids, enzymes, natural products, nucleic acids (including DNA, mRNA, microRNA, tRNA, rRNA, long non-coding RNAs, snoRNA, nucleosides, nucleotides, structure analogues or combinations thereof), nutrients, receptors, and vitamins.

In some embodiments, the amount of sample requires to provide sufficient data for analysis, or analysis with a the confidence rates or error rates described herein, is no more than about 1 ng, no more than about 5 ngs, no more than about 10 ngs, no more than about 15 ngs, no more than about 20 ngs, no more than about 25 ngs, no more than about 30 ngs, no more than about 35 ngs, no more than about 40 ngs, no more than about 45 ngs, no more than about 50 ngs, no more than about 55 ngs, no more than about 60 ngs, no more than about 65 ngs, no more than about 70 ngs, no more than about 75 ngs, no more than about 80 ngs, no more than about 85 ngs, no more than about 90 ngs, no more than about 95 ngs, no more than about 100 ngs, no more than about 200 ngs, no more than about 300 ngs, no more than about 400 ngs, no more than about 500 ngs, no more than about 600 ngs, no more than about 700 ngs, no more than about 800 ngs, no more than about 900 ngs, or no more than about 1 mg. In some embodiments, the amount of sample requires to provide sufficient data for analysis, or analysis with a the confidence rates or error rates described herein, is no more than about 1 pg, no more than about 5 pgs, no more than about 10 pgs, no more than about 15 pgs, no more than about 20 pgs, no more than about 25 pgs, no more than about 30 pgs, no more than about 35 pgs, no more than about 40 pgs, no more than about 45 pgs, no more than about 50 pgs, no more than about 55 pgs, no more than about 60 pgs, no more than about 65 pgs, no more than about 70 pgs, no more than about 75 pgs, no more than about 80 pgs, no more than about 85 pgs, no more than about 90 pgs, no more than about 95 pgs, no more than about 100 pgs, no more than about 200 pgs, no more than about 300 pgs, no more than about 400 pgs, no more than about 500 pgs, no more than about 600 pgs, no more than about 700 pgs, no more than about 800 pgs, no more than about 900 pgs, or no more than about 1 ng.

DNA Sequencing Sample Preparation.

A non-limiting example of a comprehensive DNA sequencing protocol that generates sequencing-reads is as follows.

Sample preparation can include DNA shearing. DNA shearing can comprise: (1) Transferring 1-3 µg of DNA to a 1.5 mL tube; (2) Bringing the DNA up to a volume of up to 130 µL with nuclease-free water; and (3) Transferring DNA to a microtube in preparation for sonication at 4° C. for 1-10 minutes The sheared sample can be immobilized on a surface. Solid Phase Reversible Immobilization (SPRI™) beads can be used to immobilize a DNA or an RNA sample to a surface. The beads can be paramagnetic beads coated with nucleic acid binding moieties, such as carboxyl groups. To immobilize DNA to a set of beads, a user can: (1) Mix by vortex a quantity of beads to ensure a homogeneous solution; (2) Transfer 180 µL of bead solution to a 1.5 mL tube. (3) Add 100 µL of end-repaired DNA; (4) Mix by vortex for 5 minutes; (5) Place the tube on a magnet for 3-5 minutes, until the solution is clear; (6) Remove the cleared supernatant, while tube is on the magnet; (7) Add approximately 500 mL of 70% ethanol, while the tube is on the magnet; (8) Allow the beads to settle for approximately 1 minute; (9) Remove the ethanol and wash once with 500 µL of 70% ethanol; (10) Remove the ethanol; (11) Dry the sample on a heating block at 37° C. for 5 minutes to remove residual ethanol; (12) Add 10 µL of nuclease-free water to the beads; (13) Mix by vortex and incubate at room temperature for 2 minutes; (14) Place the tube on magnet for 2-3 minutes until the solution is clear; and (15) Transfer 15 µL of the solution to a fresh PCR tube, while being careful not to disturb the beads.

Sample preparation can include steps to add supplementary adenosine bases to immobilized/fragmented DNA. To add adenosine bases to immobilized/fragmented DNA, a user can: (1) Prepare a reaction (10 µL eluted DNA; 2 µL 10× Blue Buffer; 5 µL 1 mM dATP; and 3 µL Klenow exo-50,000 U/mL) in a 1.5 mL tube; (2) Incubate in the tube in a heat block at 37° C. for 30 minutes; and (3) Heat-inactivate the enzyme by incubating at 75° C. for 20 minutes.

Sample preparation can comprise ligating adapters to DNA fragments. An adapter can comprise a barcode. An adapter can be a structure used to attach a barcode to a target polynucleotide. A sample of DNA or RNA (total or fractionated, such as poly(A) enriched RNA) can be converted to a library of fragments with adaptors attached to one or both ends.

A non-limiting example of a protocol that can ligate an adapter to DNA fragments includes: (1) Prepare a reaction (20 µL DNA; 25 µL 2× rapid ligase buffer; 100 µM adapter mix; and 1 µL T4 DNA ligase) in a 1.5 mL tube; (2) Incubate on a thermal cycler at 20° C. for 30 minutes; and (3) Purify with AMPure™ XP beads.

The DNA-adapted ligated fragments can be purified prior to sequencing. A non-limiting example of a method of purification includes AMPure™ DNA Purification methods. (1) SPRI™ beads can be allowed to equilibrate at room temperature. (2) Beads are mixed by vortex to ensure a homogeneous solution. (3) 60 µL of bead solution is transferred to a 1.5 mL tube. (4) 50 µL of the adapter-ligated library is transferred to the tube. (5) Mix by vortex for 5 minutes. (6) The tube is placed on a magnet for 3-5 minutes, until the solution is clear. (7) The supernatant is removed, while the tube is on the magnet. (8) 500 µL of 70% ethanol is added to the sample while the tube is on the magnet. (9) Beads are allowed to settle for 1 minute. (10) Ethanol is removed and the beads are washed again with 500 µL of 70% ethanol. (11) Ethanol is removed. (12) The sample is dried on a 37° C. heat block for 5 minutes to remove residual ethanol. (13) Add 30 µL of nuclease-free water to the beads. (14) The sample is mixed by vortex and incubated at room temperature for about 2 minutes. (15) The tube is placed on a magnet for about 2-3 minutes until the solution is clear. (16) 30 µL of solution is transferred to fresh PCR tubes. To confirm the addition of adapters to DNA samples, 1 µL of sample can be evaluated on, for example, an Agilent 2100 Bioanalyzer™.

A non-limiting example of a protocol for sample library amplification includes: (1) Prepare a reaction (15 µL purified DNA template; 1.5 µL 25 µM forward primer; 1.5 µL 25 µM reverse primer; 25 µL 2× Mastermix; and 7 µL water) for each sample to be amplified. (2) Run a thermal cycler program (A: 98° C. for 2 minutes; B: 11 cycles of: i) 98° C. for 20 seconds; ii) 64° C. for 30 seconds; and iii) 72° C. for 5 minutes; C: 72° C. for 5 minutes; and D: hold at 4° C.). (3) Purify sample.

RNA Sequencing Sample Preparation.

A method and a computer program product of the invention can analyze RNA sequencing data. A non-limiting example of a protocol generating RNA sequencing reads is the following: Whole transcriptome RNA can be isolated and a library can be prepared for deep sequencing analysis. Library Construction: (1) mRNA is purified from Total RNA using magnetic beads: 5-100 ng of total RNA is diluted with nuclease-free water and heated to disrupt the secondary structures and then added to pre-prepared Magnetic Oligo (dT) Beads. After washing with washing buffer, 10 mM Tris-HCl is added to the beads and mRNA is eluted from the beads. (2) Fragmentation of the mRNA: The mRNA is fragmented into small pieces using divalent cations under elevated temperature. (3) Synthesis of the first and second strands of cDNA: The cleaved RNA fragments are copied into a first strand of cDNA using reverse transcriptase and random primers. Then the primary strand of mRNA is removed by RNaseH and a replacement strand is synthesized to generate double-stranded cDNA. (4) Overhang end repair into blunt ends: The overhangs resulting from fragmentation are converted into blunt ends using T4 DNA polymerase and E. coli DNA polymerase I Klenow fragment. The 3' to 5' exonuclease activity of these enzymes removes 3' overhangs, and the polymerase activity fills in the 5' overhangs. (5) Addition of 'A' Bases to the 3' End of the DNA Fragments: An 'A' base is added to the 3' end of the blunt phosphorylated DNA fragments, using the polymerase activity of Klenow fragment (3' to 5' exo minus). This step prepares the DNA fragments for ligation to the adapters, which have a single 'T' base overhang at the 3' end. (6) Ligation of Adapters to DNA Fragments: The adapters are ligated to the ends of the DNA fragments, preparing DNA fragments to be hybridized to a flow cell. (7) Purification of Ligation Products: The products of the ligation reaction are purified on a 2% TAE-agarose gel to remove all unligated adapters and any adapters that have ligated to one another, and selected in a size-range of templates (for example 200±25 bp) for downstream enrichment. (8) Enrichment of the Adapter-cDNA Fragments by PCR: The cDNA fragments with adapters on both ends are amplified for 15 cycles of PCR, with two primers complementary to the ends of the adapters. (9) Validate the Library: Check the size, purity, and concentration of the library constructs using standard methods.

Template hybridization, cluster amplification, linearization, blocking, and primer hybridization: (1) An example of a sequencing apparatus is the cBot™ fluidics device that hybridizes samples onto a flow cell and amplifies for later sequencing on the HiSeq2000/1000 ™. The instrument uses solid support amplification to create an ultra-high density sequencing flow cell with millions of clusters, each containing ~1,000 copies of template. Prior to sequencing, an initial in vitro clonal amplification step is used. The bridge PCR for cluster generation is achieved via the following steps: (2) Denaturation of the library construct and hybridization of the template DNA: Original dsDNA construct is denatured and converted to ssDNA that already has adapters ligated thereto, and is ready to hybridize via the homology of the adapters to a complementary adaptor primer on a grafted flowcell. (3) Amplification of template DNA: the template DNA is isothermally amplified to form a surface-bound colony (the clonal DNA cluster). (4) Linearization: dsDNA clusters are linearized as the first step of converting dsDNA to ssDNA that is suitable for sequencing. (5) Blocking: the free 3' OH ends of the linearized dsDNA clusters are blocked. This step prevents nonspecific sites from being sequenced. (6) Denaturation and hybridization of sequencing primers: in this step the denatured dsDNA is then hybridized to a sequencing primer, or multiple sequencing primers, onto the linearized and blocked clusters. After this step, the flow cell is ready for sequencing.

Reference Sequences, Genomes, and Databases.

A computer program product and a method of the invention can analyze sequencing reads drawn from a database. A database can provide DNA, RNA, or protein sequencing data. A database comprising sequencing information can be a public database or a private database. A database can be specialized in a particular type of digital sequencing read data, or can be a central database comprising a plurality of distinct data formats. Non-limiting examples of databases include the NCBI completely sequenced genomes database, the *Saccharomyces* Genome database, FlyBase, WormBase, *Arabidopsis* Information Resource, Zebrafish Information Network, Swiss-Prot, TrEMBL, Protein Information Resource, Uniprot, 1000 Genomes Project database, and a database of the International HapMap Project.

A reference genome can be assembled as a representative reference sequence of a gene, a set of genes, or of the genome of a creature. A creature can be any creature in the six kingdoms of a biological taxonomical rank: Animalia, Plantae, Fungi, Protista, Archaea, and Bacteria. A creature can be, for example, a Human (*H. sapiens*), a Mouse (*M. musculus*), a Rat (*R. norvegicus*), a Fly (*D. melanogaster*), a Fly (*D. pseudoobscura*), a Fly (*D. pmelanogaster*—multiple strains), a Honey bee (*A. mellifera*), a Sea urchin (*S. purpuratus*), Bovine (*B. taurus*), a Rhesus monkey (*M. mulatta*), an Orangutan (*P. pygmaeus*), a Marmoset (*C. jacchus*), a Pea aphid (*A. pisum*), a Wasp (*Nasonia* spp.), a Beetle (*T. castaneum*), a Wallaby (*M. eugenii*), an Acorn worm (*S. kowalevskii*), a Hyrax (*P. capensis*), a Megabat (*P. vampyrus*), an Armadillo (*D. novemcinctus*), a Baboon (*P. anubis*), a Bumble bee (*B. terrestris*), a California mouse (*P. californicus*), a Centipede (*S. maritima*), a Cotton bollworm (*H. armigera*), a Deer mouse (*P. maniculatus*), a Gibbon, a Dolphin, Bottlenose (*T. truncatus*), a Dwarf honey bee (*A. florea*), mayze (*Z. mays*), or any other creature.

A digital sequence of a reference sequence can be contained in a database of reference sequences. A database of reference sequences can comprise a plurality of genomes and/or proteomes, sequenced with a plurality of methods. A reference genome can be a haploid, a diploid, or a polyploid genome. In some embodiments, the reference genome is a human genome. In some embodiments, the reference genome is an annotated human genome. In some embodiments, a system, a method, an algorithm, and/or a computer program product of the invention can identify a mutation and/or a variant in a genomic sample based on a comparison of an experimentally-generated sequencing read with a reference genome.

A reference sequence can be a digital nucleic acid or amino acid sequence. A reference genome can be a reference sequence. A reference genome can comprise digital annotations of a known allele, even if the known allele is not present in either the physical or the digital version of the nucleic acid sequence. For example, humans have the A, B, AB, or O blood type as designated in the ABO blood system. A reference sequence containing only an O allele can be annotated with alleles corresponding to the A, B, and AB gene sequences.

Polymorphisms.

A large number of variants have been identified in sequenced genomes, including the human genome. Variants can be of functional significance, for example, leading to a missense mutation or a non-sense mutation in a protein coding gene. Variants can be of no functional significance, such as silent mutations. Single nucleotide polymorphims (SNPs) can be of functional significance.

In some embodiments, the invention provided herein can identify polymorphisms present in a genome. In some embodiments, the invention can associate an identified polymorphism with a condition. In some embodiments polymorphisms identified in a genome as compared to a reference genome represents from about 0.1% to about 0.05%, from about 0.1% to about 0.01%, from about 0.05% to about 0.01%, from about 0.05% to about 0.005%, from about 0.01% to about 0.005%, or from about 0.005% to about 0.0001% of a sequenced genome. In some embodiments, the invention identifies a mutation in a sample based on a comparison with a reference sequence.

TABLE 3 illustrates the physical organization and the number of polymorphisms reported within a human genome by chromosome.

TABLE 3

| Chromosome | Length (mm) | Base Pairs | No. of Reported Poly-morphims | Protein coding genes | Pseudo-genes | Micro RNA | Ribosomal RNA | Small nuclear RNA |
|---|---|---|---|---|---|---|---|---|
| 1 | 85 | 249,250,621 | 4,401,091 | 2,012 | 1,130 | 134 | 66 | 221 |
| 2 | 83 | 243,199,373 | 4,607,702 | 1,203 | 948 | 115 | 40 | 161 |
| 3 | 67 | 198,022,430 | 3,894,345 | 1,040 | 719 | 99 | 29 | 138 |
| 4 | 65 | 191,154,276 | 3,673,892 | 718 | 698 | 92 | 24 | 120 |
| 5 | 62 | 180,915,260 | 3,436,667 | 849 | 676 | 83 | 25 | 106 |
| 6 | 58 | 171,115,067 | 3,360,890 | 1,002 | 731 | 81 | 26 | 111 |
| 7 | 54 | 159,138,663 | 3,045,992 | 866 | 803 | 90 | 24 | 90 |
| 8 | 50 | 146,364,022 | 2,890,692 | 659 | 568 | 80 | 28 | 86 |
| 9 | 48 | 141,213,431 | 2,581,827 | 785 | 714 | 69 | 19 | 66 |
| 10 | 46 | 135,534,747 | 2,609,802 | 745 | 500 | 64 | 32 | 87 |
| 11 | 46 | 135,006,516 | 2,607,254 | 1,258 | 775 | 63 | 24 | 74 |
| 12 | 45 | 133,851,895 | 2,482,194 | 1,003 | 582 | 72 | 27 | 106 |
| 13 | 39 | 115,169,878 | 1,814,242 | 318 | 323 | 42 | 16 | 45 |
| 14 | 36 | 107,349,540 | 1,712,799 | 601 | 472 | 92 | 10 | 65 |
| 15 | 35 | 102,531,392 | 1,577,346 | 562 | 473 | 78 | 13 | 63 |

TABLE 3-continued

| Chromosome | Length (mm) | Base Pairs | No. of Reported Poly-morphims | Protein coding genes | Pseudo-genes | Micro RNA | Ribosomal RNA | Small nuclear RNA |
|---|---|---|---|---|---|---|---|---|
| 16 | 31 | 90,354,753 | 1,747,136 | 805 | 429 | 52 | 32 | 53 |
| 17 | 28 | 81,195,210 | 1,491,841 | 1,158 | 300 | 61 | 15 | 80 |
| 18 | 27 | 78,077,248 | 1,448,602 | 268 | 59 | 32 | 13 | 51 |
| 19 | 20 | 59,128,983 | 1,171,356 | 1,399 | 181 | 110 | 13 | 29 |
| 20 | 21 | 63,025,520 | 1,206,753 | 533 | 213 | 57 | 15 | 46 |
| 21 | 16 | 48,129,895 | 787,784 | 225 | 150 | 16 | 5 | 21 |
| 22 | 17 | 51,304,566 | 745,778 | 431 | 308 | 31 | 5 | 23 |
| X | 53 | 155,270,560 | 2,174,952 | 815 | 780 | 128 | 22 | 85 |
| Y | 20 | 59,373,566 | 286,812 | 45 | 327 | 15 | 7 | 17 |
| Mt. DNA | 0.0054 | 16,569 | 929 | 13 | 0 | 0 | 2 | 0 |

Therapies.

Integrating inherited genetic risk information into the clinical decision-making process early in life can have an important effect in ameliorating or even preventing disease symptoms or conditions. The computer program products and methods of the invention address pressing challenges in personalized medicine. By providing a streamlined and rapid method for effective interpretation and characterization of data generated in sequencing experiments, the invention can solve challenges in conveying meaningful interpretations of a genomic or proteomic sequence to physicians. The invention can facilitate characterization of various genetic conditions based on sequencing data.

Subjects can be afflicted by one or a plurality of conditions, or subjects can be healthy. Subjects can be of any age, including, for example, elderly adults, adults, adolescents, pre-adolescents, children, toddlers, and infants. Non limiting examples of subjects include humans, other primates, and mammals such as dogs, cats, horses, pigs, rabbits, rats, and mice.

In some embodiments, the invention can identify a condition based on an analysis of sequencing data associated with a sample.

A computer-program product and a method of the invention can identify genetic signatures associated with various conditions. Non-limiting examples of conditions include cystic fibrosis, Duchenne muscular dystrophy, Haemochromatosis, Tay-Sachs disease, Prader-Willi syndrome, Angelman syndrome, neurofibromatosis, phenylketonuria, Canavan disease, Coeliac disease, Acid beta-glucosidase deficiency, Gaucher, Charcot-Marie-Tooth disease, color blindness, Cri du chat, polycystic kidney disease, acrocephaly, familial adenomatous polyposis, adrenal gland disorders, amyotrophic lateral sclerosis (ALS), Alzheimer's disease, Parkinson's disease, anemia, ataxia, ataxia telangiectasia, autism, bone marrow diseases, Bonnevie-Ullrich syndrome, brain diseases, von Rippel-Lindau disease, congenital heart disease, Crohn's disease, dementia, myotonic dystrophy, Fabry disease, fragile X syndrome, galactosemia, genetic emphysema, retinoblastoma, Pendred syndrome, Usher syndrome, Wilson disease, neuropathies, Huntington's disease, immune system disorders, gout, X-linked spinal-bulbar muscle atrophy, learning disabilities, Li-Fraumeni syndrome, lipase D deficiency, Lou Gehrig disease, Marfan syndrome, metabolic disorders, Niemann-Pick, Noonan syndrome, Osteopsathyrosis, Peutz-Jeghers syndrome, Pfeiffer syndrome, porphyria, progeria, Rett syndrome, tuberous sclerosis, speech and communication disorders, spinal muscular atrophy, Treacher Collins syndrome, trisomies, and monosomies.

A computer-program product, a method, an algorithm, or a system herein can identify variants present in a various cancers. Non-limiting examples of cancers include: acute lymphoblastic leukemia, acute myeloid leukemia, adrenocortical carcinoma, AIDS-related cancers, AIDS-related lymphoma, anal cancer, appendix cancer, astrocytomas, basal cell carcinoma, bile duct cancer, bladder cancer, bone cancers, brain tumors, such as cerebellar astrocytoma, cerebral astrocytoma/malignant glioma, ependymoma, medulloblastoma, supratentorial primitive neuroectodermal tumors, visual pathway and hypothalamic glioma, breast cancer, bronchial adenomas, Burkitt lymphoma, carcinoma of unknown primary origin, central nervous system lymphoma, cerebellar astrocytoma, cervical cancer, childhood cancers, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, esophageal cancer, Ewing's sarcoma, germ cell tumors, gallbladder cancer, gastric cancer, gastrointestinal carcinoid tumor, gastrointestinal stromal tumor, gliomas, hairy cell leukemia, head and neck cancer, heart cancer, hepatocellular (liver) cancer, Hodgkin lymphoma, Hypopharyngeal cancer, intraocular melanoma, islet cell carcinoma, Kaposi sarcoma, kidney cancer, laryngeal cancer, lip and oral cavity cancer, liposarcoma, liver cancer, lung cancers, such as non-small cell and small cell lung cancer, lymphomas, leukemias, macroglobulinemia, malignant fibrous histiocytoma of bone/osteosarcoma, medulloblastoma, melanomas, mesothelioma, metastatic squamous neck cancer with occult primary, mouth cancer, multiple endocrine neoplasia syndrome, myelodysplastic syndromes, myeloid leukemia, nasal cavity and paranasal sinus cancer, nasopharyngeal carcinoma, neuroblastoma, non-Hodgkin lymphoma, non-small cell lung cancer, oral cancer, oropharyngeal cancer, osteosarcoma/malignant fibrous histiocytoma of bone, ovarian cancer, ovarian epithelial cancer, ovarian germ cell tumor, pancreatic cancer, pancreatic cancer islet cell, paranasal sinus and nasal cavity cancer, parathyroid cancer, penile cancer, pharyngeal cancer, pheochromocytoma, pineal astrocytoma, pineal germinoma, pituitary adenoma, pleuropulmonary blastoma, plasma cell neoplasia, primary central nervous system lymphoma, prostate cancer, rectal cancer, renal cell carcinoma, renal pelvis and ureter transitional cell cancer, retinoblastoma, rhabdomyosarcoma, salivary gland cancer, sarcomas, skin cancers, skin carcinoma merkel cell, small intestine cancer, soft tissue sarcoma, squamous cell carcinoma, stomach cancer, T-cell lymphoma, throat cancer, thymoma, thymic carcinoma, thyroid cancer, trophoblastic tumor (gestational), cancers of unknown primary site, urethral cancer, uterine sarcoma, vaginal cancer, vulvar cancer, Waldenström macroglobulinemia, and Wilms tumor.

The invention can further comprise recommending or providing a therapy to a subject based on an analysis of sequencing data. A therapy can be a medicinal intervention, such as a chemotherapy, or a medical procedure, such as a surgery. For example, an analysis of sequencing data can identify a polymorphim known to contribute to cystic fibrosis in a sample. Non-limiting examples of therapeutic interventions that can be provided to a subject afflicted by cystic fibrosis include antibiotics, anti-inflammatories, enzyme replacement, mucolytics, airway clearance, postural drainage, wearing an inflatable therapy vest, using a flutter device, diet regimens, exercise regimens, and organ transplants.

The therapy provided to the subject can be directed towards a genetic component of an identified condition. For example, mutations in the Abelson tyrosine kinase (ABL) gene can lead to Chronic Myeloid Leukemia (CML), and single nucleotide polymorphisms can render subjects resistant to Gleevec. An analysis of sequencing data associated with a sample can identify a polymorphisms associated with CIVIL, and a physician can use an output to determine that the subject is potentially non-responsive to Gleevec.

Data Processing and Error Rates.

Non-limiting examples of real-time analysis time-frames for a comparison of sequencing reads include: less than 1 second, less than 2 seconds, less than 3 seconds, less than 4 seconds, less than 5 seconds, less than 10 seconds, less than 15 seconds, less than 30 seconds, less than 45 seconds, less than 60 seconds; less than 2 minutes; less than 3 minutes; less than 4 minutes; less than 5 minutes; less than 6 minutes; less than 7 minutes; less than 8 minutes; less than 9 minutes; less than 10 minutes; less than 11 minutes; less than 12 minutes; less than 13 minutes; less than 14 minutes; less than 15 minutes, less than 16 minutes; less than 17 minutes; less than 18 minutes; less than 19 minutes; less than 20 minutes; less than 21 minutes; less than 22 minutes; less than 23 minutes; less than 24 minutes; less than 25 minutes; less than 26 minutes; less than 27 minutes; less than 28 minutes; less than 29 minutes; and less than 30 minutes.

Non-limiting examples of real-time analysis time-frames of complete sequencing experiments include less than 15 minutes; from about 10 minutes to about 30 minutes; from about 10 minutes to about 1 hour; from about 10 minutes to about 2 hours; from about 10 minutes to about 3 hours; from about 10 minutes to about 4 hours; from about 10 minutes to about 5 hours; from about 10 minutes to about 6 hours; from about 10 minutes to about 7 hours; from about 10 minutes to about 8 hours; from about 10 minutes to about 9 hours; from about 10 minutes to about 10 hours; from about 1 hour to about 2 hours; from about 1 hour to about 3 hours; from about 1 hour to about 4 hours; from about 1 hour to about 5 hours; from about 1 hour to about 6 hours; from about 1 hour to about 7 hours; from about 1 hour to about 8 hours; from about 1 hour to about 9 hours; from about 1 hour to about 10 hours; from about 2 hours to about 3 hours; from about 2 hours to about 4 hours; from about 2 hours to about 5 hours; from about 2 hours to about 6 hours; from about 2 hours to about 7 hours; from about 2 hours to about 8 hours; from about 2 hours to about 9 hours; from about 2 hours to about 10 hours; from about 3 hours to about 4 hours; from about 3 hours to about 5 hours; from about 3 hours to about 6 hours; from about 3 hours to about 7 hours; from about 3 hours to about 8 hours; from about 3 hours to about 9 hours; from about 3 hours to about 10 hours; from about 4 hours to about 5 hours; from about 4 hours to about 6 hours; from about 4 hours to about 7 hours; from about 4 hours to about 8 hours; from about 4 hours to about 9 hours; from about 4 hours to about 10 hours; from about 5 hours to about 6 hours; from about 5 hours to about 7 hours; from about 5 hours to about 8 hours; from about 5 hours to about 9 hours; from about 5 hours to about 10 hours; from about 6 hours to about 7 hours; from about 6 hours to about 8 hours; from about 6 hours to about 9 hours; from about 6 hours to about 10 hours; from about 7 hours to about 8 hours; from about 7 hours to about 9 hours; from about 7 hours to about 10 hours; from about 8 hours to about 9 hours; from about 8 hours to about 10 hours; from about 9 hours to about 10 hours; and about 10 hours.

A method of identifying sequencing errors can comprise comparing a first sequencing read, with a number of additional sequencing reads. The additional sequencing reads can comprise a common barcode or share a level of homology with the first sequencing read or one another. In some embodiments, a confidence level of determining that a variant in a sequencing assay is an error increases as the number of additional sequencing reads compared to the first sequencing read increases.

In some embodiments, a computer program product and an algorithm of the invention can detect, process, distinguish, and group at least 100 barcodes per sample; at least 500 barcodes per sample; at least 1,000 barcodes per sample; at least 2,000 barcodes per sample; at least 3,000 barcodes per sample; at least 4,000 barcodes per sample; at least 5,000 barcodes per sample; at least 6,000 barcodes per sample; at least 7,000 barcodes per sample; at least 8,000 barcodes per sample; at least 9,000 barcodes per sample; at least 10,000 barcodes per sample; at least 11,000 barcodes per sample; at least 12,000 barcodes per sample; at least 13,000 barcodes per sample; at least 14,000 barcodes per sample; at least 15,000 barcodes per sample; at least 16,000 barcodes per sample; at least 17,000 barcodes per sample; at least 18,000 barcodes per sample; at least 19,000 barcodes per sample; at least 20,000 barcodes per sample; at least 21,000 barcodes per sample; at least 22,000 barcodes per sample; at least 23,000 barcodes per sample; at least 24,000 barcodes per sample; at least 25,000 barcodes per sample; at least 26,000 barcodes per sample; at least 27,000 barcodes per sample; at least 28,000 barcodes per sample; at least 29,000 barcodes per sample; at least 30,000 barcodes per sample; at least 31,000 barcodes per sample; at least 32,000 barcodes per sample; at least 33,000 barcodes per sample; at least 34,000 barcodes per sample; at least 35,000 barcodes per sample; at least 36,000 barcodes per sample; at least 37,000 barcodes per sample; at least 38,000 barcodes per sample; at least 39,000 barcodes per sample; at least 40,000 barcodes per sample; at least 41,000 barcodes per sample; at least 42,000 barcodes per sample; at least 43,000 barcodes per sample; at least 44,000 barcodes per sample; at least 45,000 barcodes per sample; at least 46,000 barcodes per sample; at least 47,000 barcodes per sample; at least 48,000 barcodes per sample; at least 49,000 barcodes per sample; at least 50,000 barcodes per sample; at least 51,000 barcodes per sample; at least 52,000 barcodes per sample; at least 53,000 barcodes per sample; at least 54,000 barcodes per sample; at least 55,000 barcodes per sample; at least 56,000 barcodes per sample; at least 57,000 barcodes per sample; at least 58,000 barcodes per sample; at least 59,000 barcodes per sample; at least 60,000 barcodes per sample; at least 61,000 barcodes per sample; at least 62,000 barcodes per sample; at least 63,000 barcodes per sample; at least 64,000 barcodes per sample; at least 65,000 barcodes per sample; at least 66,000 barcodes per sample; at least 67,000 barcodes per sample; at least 68,000 barcodes per sample; at least 69,000 barcodes per sample; at least 70,000 barcodes per sample; at least 71,000 barcodes per sample; at least 72,000 barcodes per sample; at least 73,000 barcodes per sample; at least 74,000 barcodes per sample; at least 75,000 barcodes per sample; at least 76,000 barcodes per sample; at least 77,000 barcodes per sample; at least 78,000 barcodes per sample; at least 79,000 barcodes per sample; at least 80,000 barcodes per sample; at least 81,000 barcodes per sample; at least 82,000 barcodes per sample; at least 83,000 barcodes per sample; at least 84,000 barcodes per sample; at least 85,000 barcodes per sample; at least 86,000 barcodes per sample; at least 87,000 barcodes per sample; at least 88,000 barcodes per sample; at least 89,000 barcodes per sample; at least 90,000 barcodes per sample; at least 91,000 barcodes per sample; at least 92,000 barcodes per sample; at least 93,000 barcodes per sample; at least 94,000 barcodes per sample; at least 95,000 barcodes per sample; at least 96,000 barcodes per sample; at least 97,000 barcodes per sample; at least 98,000 barcodes per sample; at least 99,000 barcodes per sample; or at least 100,000 barcodes per sample.

In some embodiments, a computer program product and an algorithm of the invention can detect, process, distinguish, group, and/or separate no greater than 100 barcodes per sample; no greater than 500 barcodes per sample; no greater than 1,000 barcodes per sample; no greater than 2,000 barcodes per sample; no greater than 3,000 barcodes per sample; no greater than 4,000 barcodes per sample; no greater than 5,000 barcodes per sample; no greater than 6,000 barcodes per sample; no greater than 7,000 barcodes per sample; no greater than 8,000 barcodes per sample; no greater than 9,000 barcodes per sample; no greater than 10,000 barcodes per sample; no greater than 11,000 barcodes per sample; no greater than 12,000 barcodes per sample; no greater than 13,000 barcodes per sample; no greater than 14,000 barcodes per sample; no greater than 15,000 barcodes per sample; no greater than 16,000 barcodes per sample; no greater than 17,000 barcodes per sample; no greater than 18,000 barcodes per sample; no greater than 19,000 barcodes per sample; no greater than 20,000 barcodes per sample; no greater than 21,000 barcodes per sample; no greater than 22,000 barcodes per sample; no greater than 23,000 barcodes per sample; no greater than 24,000 barcodes per sample; no greater than 25,000 barcodes per sample; no greater than 26,000 barcodes per sample; no greater than 27,000 barcodes per sample; no greater than 28,000 barcodes per sample; no greater than 29,000 barcodes per sample; no greater than 30,000 barcodes per sample; no greater than 31,000 barcodes per sample; no greater than 32,000 barcodes per sample; no greater than 33,000 barcodes per sample; no greater than 34,000 barcodes per sample; no greater than 35,000 barcodes per sample; no greater than 36,000 barcodes per sample; no greater than 37,000 barcodes per sample; no greater than 38,000 barcodes per sample; no greater than 39,000 barcodes per sample; no greater than 40,000 barcodes per sample; no greater than 41,000 barcodes per sample; no greater than 42,000 barcodes per sample; no greater than 43,000 barcodes per sample; no greater than 44,000 barcodes per sample; no greater than 45,000 barcodes per sample; no greater than 46,000 barcodes per sample; no greater than 47,000 barcodes per sample; no greater than 48,000 barcodes per sample; no greater than 49,000 barcodes per sample; no greater than 50,000 barcodes per sample; no greater than 51,000 barcodes per sample; no greater than 52,000 barcodes per sample; no greater than 53,000 barcodes per sample; no greater than 54,000 barcodes per sample; no greater than 55,000 barcodes per sample; no greater than 56,000 barcodes per sample; no greater than 57,000 barcodes per sample; no greater than 58,000 barcodes per sample; no greater than 59,000 barcodes per sample; no greater than 60,000 barcodes per sample; no greater than 61,000 barcodes per sample; no greater than 62,000 barcodes per sample; no greater than 63,000 barcodes per sample; no greater than 64,000 barcodes per sample; no greater than 65,000 barcodes per sample; no greater than 66,000 barcodes per sample; no greater than 67,000 barcodes per sample; no greater than 68,000 barcodes per sample; no greater than 69,000 barcodes per sample; no greater than 70,000 barcodes per sample; no greater than 71,000 barcodes per sample; no greater than 72,000 barcodes per sample; no greater than 73,000 barcodes per sample; no greater than 74,000 barcodes per sample; no greater than 75,000 barcodes per sample; no greater than 76,000 barcodes per sample; no greater than 77,000 barcodes per sample; no greater than 78,000 barcodes per sample; no greater than 79,000 barcodes per sample; no greater than 80,000 barcodes per sample; no greater than 81,000 barcodes per sample; no greater than 82,000 barcodes per sample; no greater than 83,000 barcodes per sample; no greater than 84,000 barcodes per sample; no greater than 85,000 barcodes per sample; no greater than 86,000 barcodes per sample; no greater than 87,000 barcodes per sample; no greater than 88,000 barcodes per sample; no greater than 89,000 barcodes per sample; no greater than 90,000 barcodes per sample; no greater than 91,000 barcodes per sample; no greater than 92,000 barcodes per sample; no greater than 93,000 barcodes per sample; no greater than 94,000 barcodes per sample; no greater than 95,000 barcodes per sample; no greater than 96,000 barcodes per sample; no greater than 97,000 barcodes per sample; no greater than 98,000 barcodes per sample; no greater than 99,000 barcodes per sample; or no greater than 100,000 barcodes per sample.

An identified error rate within a sequence read can be of about 1 nucleotide per sequencing read, about 2 nucleotides per sequencing read, about 3 nucleotides per sequencing read, about 4 nucleotides per sequencing read, about 5 nucleotides per sequencing read, about 6 nucleotides per sequencing read, about 7 nucleotides per sequencing read, about 8 nucleotides per sequencing read, about 9 nucleotides per sequencing read, about 10 nucleotides per sequencing read, about 11 nucleotides per sequencing read, about 12 nucleotides per sequencing read, about 13 nucleotides per sequencing read, about 14 nucleotides per sequencing read, about 15 nucleotides per sequencing read, about 16 nucleotides per sequencing read, about 17 nucleotides per sequencing read, about 18 nucleotides per sequencing read, about 19 nucleotides per sequencing read, about 20 nucleotides per sequencing read, about 21 nucleotides per sequencing read, about 22 nucleotides per sequencing read, about 23 nucleotides per sequencing read, about 24 nucleotides per sequencing read, about 25 nucleotides per sequencing read, about 26 nucleotides per sequencing read, about 27 nucleotides per sequencing read, about 28 nucleotides per sequencing read, about 29 nucleotides per sequencing read, about 30 nucleotides per sequencing read, about 31 nucleotides per sequencing read, about 32 nucleotides per sequencing read, about 33 nucleotides per sequencing read, about 34 nucleotides per sequencing read, about 35 nucleotides per sequencing read, about 36 nucleotides per sequencing read, about 37 nucleotides per sequencing read, about 38 nucleotides per sequencing read, about 39 nucleotides per sequencing read, or about 40 nucleotides per sequencing read.

An identified error rate within a sample can be about 0.00000000001%, about 0.00000000002%, about 0.00000000003%, about 0.00000000004%, about 0.00000000005%, about 0.00000000006%, about 0.00000000007%, about 0.00000000008%, about 0.00000000009%, about 0.0000000001%, about 0.0000000002%, about 0.0000000003%, about 0.0000000004%, about 0.0000000005%, about 0.0000000006%, about 0.0000000007%, about 0.0000000008%, about 0.0000000009%, about 0.000000001%, about 0.000000002%, about 0.000000003%, about 0.000000004%, about 0.000000005%, about 0.000000006%, about 0.000000007%, about 0.000000008%, about 0.000000009%, about 0.00000001%, about 0.00000002%, about 0.00000003%, about 0.00000004%, about 0.00000005%, about 0.00000006%, about 0.00000007%, about 0.00000008%, about 0.00000009%, about 0.0000001%, about 0.0000002%, about 0.0000003%, about 0.0000004%, about 0.0000005%, about 0.0000006%, about 0.0000007%, about 0.0000008%, about 0.0000009%, about 0.000001%, about 0.000002%, about 0.000003%, about 0.000004%, about 0.000005%, about 0.000006%, about 0.000007%, about 0.000008%, about 0.000009%, about 0.00001%, about 0.00002%, about 0.00003%, about 0.00004%, about 0.00005%, about 0.00006%, about 0.00007%, about 0.00008%, about 0.00009%, about 0.0001%, about 0.0002%, about 0.0003%, about 0.0001%, about 0.004%, about 0.0005%, about 0.0006%, about 0.0007%, about 0.0008%, about 0.0009%, about 0.001%, about 0.002%, about 0.003%, about 0.004%, about 0.005%, about 0.006%, about 0.007%, about 0.008%, about 0.009%, about 0.01%, about 0.02%, about 0.03%, about 0.04%, about 0.05%, about 0.06%, about 0.07%, about 0.08%, about 0.09%, or about 0.1%.

Homology.

A sequencing read can be aligned to a reference sequence with a degree of homology. A first sequencing read can be aligned to a second sequencing read with a degree of homology. A portion ("window") of a sequencing read can share a percent homology to a reference sequence, or a second sequencing read. The entirety of a sequencing read can share a percent homology to a reference sequence, or a second sequencing read. Modules of the invention can determine a statistical significance of an alignment based on a percent of shared homology between two sequences. A sequencing read can share structural and/or base-pair ("pairwise") homology to a reference sequence or a second sequencing read. Homology can be measured oven an entire sequence or a fragment of a sequence. Homology can be measured by a computer-executable algorithm, for example, the Basic Local Alignment Search Tool (BLAST).

A sequencing read and a reference sequence can share about 1% pairwise homology, about 2% pairwise homology, about 3% pairwise homology, about 4% pairwise homology, about 5% pairwise homology, about 6% pairwise homology, about 7% pairwise homology, about 8% pairwise homology, about 9% pairwise homology, about 10% pairwise homology, about 11% pairwise homology, about 12% pairwise homology, about 13% pairwise homology, about 14% pairwise homology, about 15% pairwise homology, about 16% pairwise homology, about 17% pairwise homology, about 18% pairwise homology, about 19% pairwise homology, about 20% pairwise homology, about 21% pairwise homology, about 22% pairwise homology, about 23% pairwise homology, about 24% pairwise homology, about 25% pairwise homology, about 26% pairwise homology, about 27% pairwise homology, about 28% pairwise homology, about 29% pairwise homology, about 30% pairwise homology, about 31% pairwise homology, about 32% pairwise homology, about 33% pairwise homology, about 34% pairwise homology, about 35% pairwise homology, about 36% pairwise homology, about 37% pairwise homology, about 38% pairwise homology, about 39% pairwise homology, about 40% pairwise homology, about 41% pairwise homology, about 41% pairwise homology, about 42% pairwise homology, about 43% pairwise homology, about 44% pairwise homology, about 45% pairwise homology, about 46% pairwise homology, about 47% pairwise homology, about 48% pairwise homology, about 49% pairwise homology, about 50% pairwise homology, about 51% pairwise homology, about 52% pairwise homology, about 53% pairwise homology, about 54% pairwise homology, about 55% pairwise homology, about 56% pairwise homology, about 57% pairwise homology, about 58% pairwise homology, about 59% pairwise homology, about 60% pairwise homology, about 61% pairwise homology, about 62% pairwise homology, about 63% pairwise homology, about 64% pairwise homology, about 65% pairwise homology, about 66% pairwise homology, about 67% pairwise homology, about 68% pairwise homology, about 69% pairwise homology, about 70% pairwise homology, about 71% pairwise homology, about 72% pairwise homology, about 73% pairwise homology, about 74% pairwise homology, about 75% pairwise homology, about 76% pairwise homology, about 77% pairwise homology, about 78% pairwise homology, about 79% pairwise homology, about 80% pairwise homology, about 81% pairwise homology, about 82% pairwise homology, about 83% pairwise homology, about 84% pairwise homology, about 85% pairwise homology, about 86% pairwise homology, about 87% pairwise homology, about 88% pairwise homology, about 89% pairwise homology, about 90% pairwise homology, about 91% pairwise homology, about 92% pairwise homology, about 93% pairwise homology, about 94% pairwise homology, about 95% pairwise homology, about 96% pairwise homology, about 97% pairwise homology, about 98% pairwise homology, about 99% pairwise homology, or about 100% pairwise homology to a reference sequence or a second sequencing read.

An algorithm can allow for gaps in an alignment. An alignment gap can be of about 1 residue, about 2 residues, about 3 residues, about 4 residues, about 5 residues, about 6 residues, about 7 residues, about 8 residues, about 9 residues, about 10 residues, about 11 residues, about 12 residues, about 13 residues, about 14 residues, about 15 residues, about 16 residues, about 17 residues, about 18 residues, about 19 residues, about 20 residues, about 21 residues, about 22 residues, about 23 residues, about 24 residues, about 25 residues, about 26 residues, about 27 residues, about 28 residues, about 29 residues, about 30 residues, about 31 residues, about 32 residues, about 33 residues, about 34 residues, about 35 residues, about 36 residues, about 37 residues, about 38 residues, about 39 residues, about 40 residues, about 41 residues, about 42 residues, about 43 residues, about 44 residues, about 45 residues, about 46 residues, about 47 residues, about 48 residues, about 49 residues, or about 50 residues. In some embodiments, an alignment gap can be more than 50 residues.

Computer Architectures.

Figure 18:
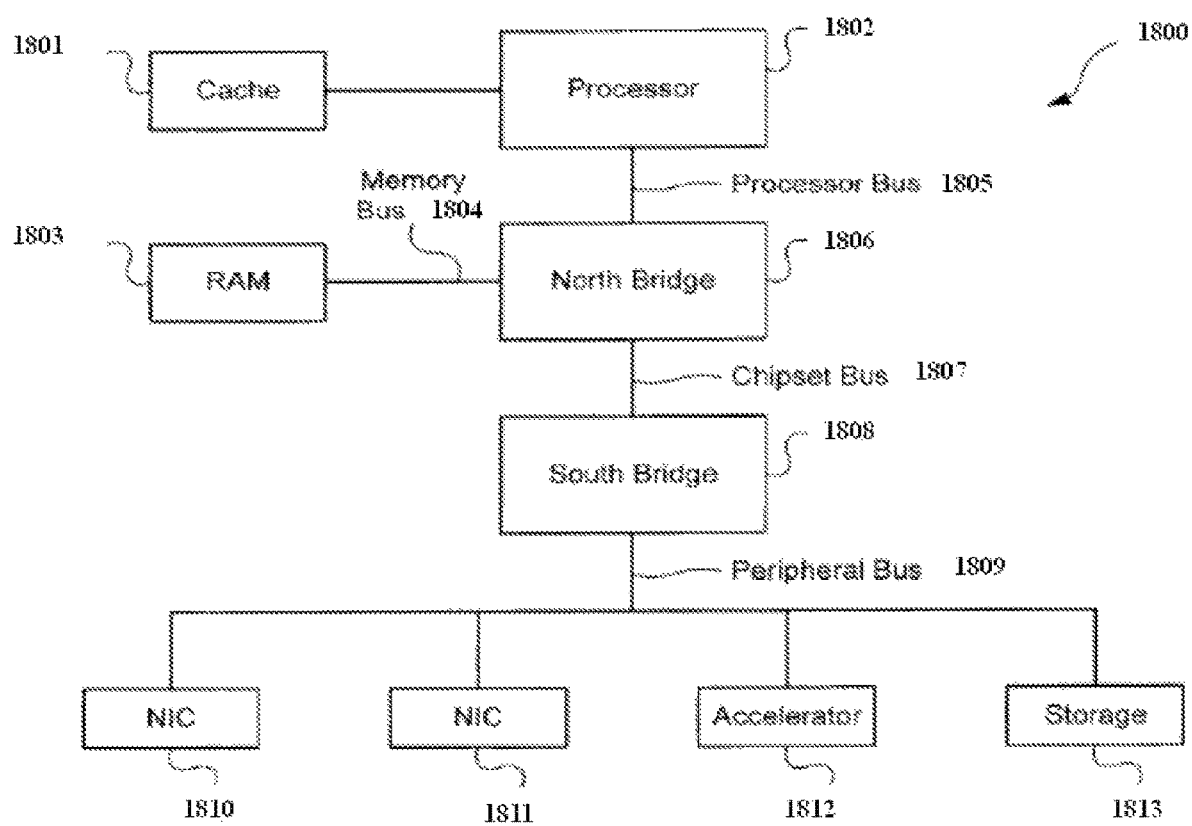
FIG. 18 is a block diagram illustrating a first example architecture of a computer system that can be used in connection with example embodiments of the present invention.

Sequencing data can be analyzed by a plurality of computers, with various computer architectures. Various computer architectures are suitable for use with the invention. FIG. 18 is a block diagram illustrating a first example architecture of a computer system 1800 that can be used in connection with example embodiments of the present invention. As depicted in FIG. 18, the example computer system can include a processor 1802 for processing instructions. Non-limiting examples of processors include: Intel Core i7™ processor, Intel Core i5™ processor, Intel Core i3 ™ processor, Intel Xeon™ processor, AMD Opteron™ processor, Samsung 32-bit RISC ARM 1176JZ(F)-S v1.0™ processor, ARM Cortex-A8 Samsung S5PC100™ processor, ARM Cortex-A8 Apple A4™ processor, Marvell PXA 930™ processor, or a functionally-equivalent processor. Multiple threads of execution can be used for parallel processing. In some embodiments, multiple processors or processors with multiple cores can be used, whether in a single computer system, in a cluster, or distributed across systems over a network comprising a plurality of computers, cell phones, and/or personal data assistant devices.

As illustrated in FIG. 18, a high speed cache 1801 can be connected to, or incorporated in, the processor 1802 to provide a high speed memory for instructions or data that have been recently, or are frequently, used by processor 1802. The processor 1802 is connected to a north bridge 1806 by a processor bus 1805. The north bridge 1806 is connected to random access memory (RAM) 1803 by a memory bus 1804 and manages access to the RAM 1803 by the processor 1802. The north bridge 1806 is also connected to a south bridge 1808 by a chipset bus 1807. The south bridge 1808 is, in turn, connected to a peripheral bus 1809. The peripheral bus can be, for example, PCI, PCI-X, PCI Express, or other peripheral bus. The north bridge and south bridge are often referred to as a processor chipset and manage data transfer between the processor, RAM, and peripheral components on the peripheral bus 1809. In some architectures, the functionality of the north bridge can be incorporated into the processor instead of using a separate north bridge chip.

In some embodiments, system 1800 can include an accelerator card 1812 attached to the peripheral bus 1809. The accelerator can include field programmable gate arrays (FPGAs) or other hardware for accelerating certain processing.

Software and data are stored in external storage 1813 and can be loaded into RAM 1803 and/or cache 1801 for use by the processor. The system 1800 includes an operating system for managing system resources; non-limiting examples of operating systems include: Linux, Windows™, MACOS™, BlackBerry OS™, iOS™, and other functionally-equivalent operating systems, as well as application software running on top of the operating system.

In this example, system 1800 also includes network interface cards (NICs) 1810 and 1811 connected to the peripheral bus for providing network interfaces to external storage, such as Network Attached Storage (NAS) and other computer systems that can be used for distributed parallel processing.

Figure 19:
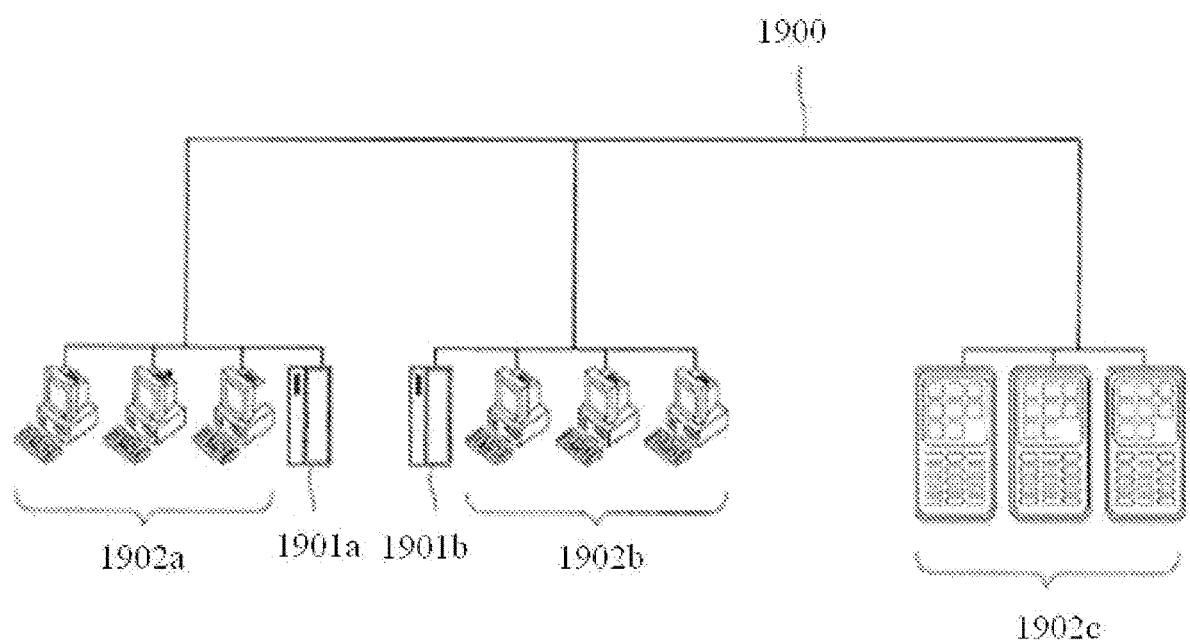
FIG. 19 is a diagram illustrating a computer network that can be used in connection with example embodiments of the present invention.

FIG. 19 is a diagram showing a network 1900 with a plurality of computer systems 1902*a*, and 1902*b*, a plurality of cell phones and personal data assistants 1902*c*, and Network Attached Storage (NAS) 1901*a*, and 1901*b*. In some embodiments, systems 1902*a*, 1902*b*, and 1902*c* can manage data storage and optimize data access for data stored in Network Attached Storage (NAS) 1901*a* and 1902*b*. A mathematical model can be used for the data and be evaluated using distributed parallel processing across computer systems 1902*a*, and 1902*b*, and cell phone and personal data assistant systems 1902*c*. Computer systems 1902*a*, and 1902*b*, and cell phone and personal data assistant systems 1902*c* can also provide parallel processing for adaptive data restructuring of the data stored in Network Attached Storage (NAS) 1901*a* and 1901*b*. FIG. 19 illustrates an example only, and a wide variety of other computer architectures and systems can be used in conjunction with the various embodiments of the present invention. For example, a blade server can be used to provide parallel processing. Processor blades can be connected through a back plane to provide parallel processing. Storage can also be connected to the back plane or as Network Attached Storage (NAS) through a separate network interface. In some embodiments, processors can maintain separate memory spaces and transmit data through network interfaces, back plane, or other connectors for parallel processing by other processors. In some embodiments, some or all of the processors can use a shared virtual address memory space.

Figure 20:
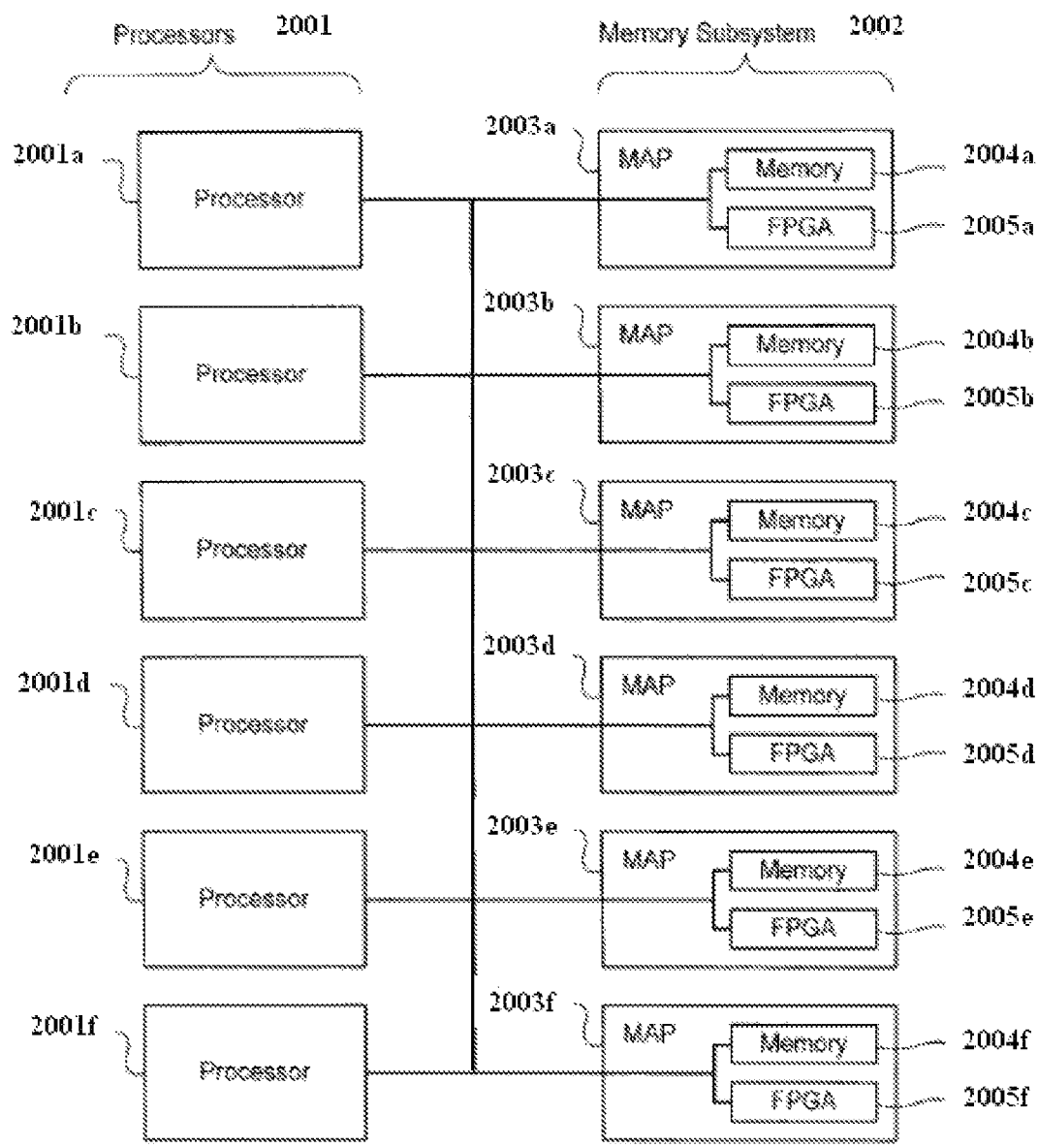
FIG. 20 is a block diagram illustrating a second example architecture of a computer system that can be used in connection with example embodiments of the present invention.

FIG. 20 is a block diagram of a multiprocessor computer system using a shared virtual address memory space. The system includes a plurality of processors 2001*a-f* that can access a shared memory subsystem 2002. The system incorporates a plurality of programmable hardware memory algorithm processors (MAPs) 2003*a-f* in the memory subsystem 2002. Each MAP 2003*a-f* can comprise a memory 2004*a-f* and one or more field programmable gate arrays (FPGAs) 2005*a-f*. The MAP provides a configurable functional unit and particular algorithms or portions of algorithms can be provided to the FPGAs 2005*a-f* for processing in close coordination with a respective processor. In this example, each MAP is globally accessible by all of the processors for these purposes. In one configuration, each MAP can use Direct Memory Access (DMA) to access an associated memory 2004*a-f*, allowing it to execute tasks independently of, and asynchronously from, the respective microprocessor 2001*a-f*. In this configuration, a MAP can feed results directly to another MAP for pipelining and parallel execution of algorithms.

The above computer architectures and systems are examples only, and a wide variety of other computer, cell phone, and personal data assistant architectures and systems can be used in connection with example embodiments, including systems using any combination of general processors, co-processors, FPGAs and other programmable logic devices, system on chips (SOCs), application specific integrated circuits (ASICs), and other processing and logic elements. Any variety of data storage media can be used in connection with example embodiments, including random access memory, hard drives, flash memory, tape drives, disk arrays, Network Attached Storage (NAS) and other local or distributed data storage devices and systems.

In example embodiments, the computer system can be implemented using software modules executing on any of the above or other computer architectures and systems. In other embodiments, the functions of the system can be implemented partially or completely in firmware, programmable logic devices such as field programmable gate arrays (FPGAs) as referenced in FIG. 20, system on chips (SOCs), application specific integrated circuits (ASICs), or other processing and logic elements. For example, the Set Processor and Optimizer can be implemented with hardware acceleration through the use of a hardware accelerator card, such as accelerator card 1812 illustrated in FIG. 18.

Embodiments

In some embodiments, the invention provides a method of analyzing sequencing data associated with a sample, the method comprising: a) receiving by a computer system a first sequencing read associated with a sequencing assay while the sequencing assay is in progress, wherein the computer system comprises a processor; and b) comparing by the processor the first sequencing read with another sequence to provide a comparison before the sequencing assay is complete. In some embodiments, the other sequence is a second sequencing read. Some embodiments further comprise determining whether the first sequencing read and the other sequence share a common subsequence. Some embodiments further comprise determining whether the first sequencing read and the other sequence correspond to a common biomolecule. Some embodiments further comprise aligning the first sequencing read and the other sequence. Some embodiments further comprise determining whether the first sequencing read and the other sequence share a common barcode. In some embodiments, the other sequence is a reference sequence. Some embodiments further comprise identifying a mutation in the sample based on the comparison. Some embodiments further comprise identifying a single nucleotide polymorphism in the sample based on the comparison. Some embodiments further comprise identifying a translocation in the sample based on the comparison. Some embodiments further comprise determining a candidate sequence, wherein the candidate sequence incorporates a portion of the first sequencing read. In some embodiments, determining the candidate sequence is performed at a rate, wherein the computer system receives a number of sequencing reads, wherein the rate increases as the number of sequencing reads increases. Some embodiments further comprise determining to which haplotype in a pair of haplotypes the first sequencing read corresponds. In some embodiments, the sample is associated with a plurality of distinct barcodes. In some embodiments, the sequencing data is DNA sequencing data. In some embodiments, the sequencing data is RNA sequencing data. In some embodiments, the sequencing data is genomic sequencing data. In some embodiments, the sequencing data is peptide sequencing data. Some embodiments further comprise outputting a result of the comparing. Some embodiments further comprise providing a therapeutic intervention to a subject based on a result of analyzing the sequencing data. In some embodiments, the first sequencing read is a partial sequencing read. In some embodiments, the first sequencing read is a complete sequencing read.

In some embodiments, the invention provides a method of analyzing sequencing data associated with a sample, the method comprising: a) receiving by a computer system a set of sequencing reads, each sequencing read independently comprising a common barcode, wherein the computer system comprises a processor; and b) aligning by the processor each sequencing read of the set of sequencing reads against a reference sequence, wherein the sample is associated with a plurality of distinct barcodes. Some embodiments further comprise receiving an additional sequencing read that does not comprise the common barcode, and filtering out the additional sequencing read that does not comprise the common barcode. Some embodiments further comprise determining a candidate sequence based on the alignment of the sequencing reads against the reference sequence. Some embodiments further comprise identifying neighboring sequencing reads in the alignment, and determining whether the neighboring sequencing reads overlap at a non-barcode subsequence. Some embodiments further comprise determining whether the sequencing reads that comprise the common barcode correspond to a common haplotype. In some embodiments, the determining whether the sequencing reads that comprise the common barcode correspond to the common haplotype comprises identifying a non-barcode subsequence common to a plurality of the sequencing reads that comprise the common barcode, and determining whether the sequencing reads of the plurality share a common single nucleotide polymorphism at the non-barcode common subsequence. Some embodiments further comprise determining a candidate sequence corresponding to one haplotype of a pair of haplotypes, wherein the candidate sequence is based on a plurality of sequencing reads, each of which comprise the common barcode, each of which share a common single nucleotide polymorphism at a common position. Some embodiments further comprise receiving a plurality of additional sequencing reads, wherein each additional sequencing read independently comprises a distinct barcode. Some embodiments further comprise aligning each additional sequencing read with the reference sequence. Some embodiments further comprise: c) receiving a plurality of additional sequencing reads, wherein each additional sequencing read independently comprises a distinct barcode; d) aligning each additional sequencing read with the reference sequence; e) selecting a window of the reference sequence; and f) determining a total of distinct barcodes associated with the additional sequencing reads that correspond to the window of the reference sequence. Some embodiments further comprise estimating a likelihood that the sample comprises a mutation. Some embodiments further comprise determining which haplotype in a pair of haplotypes possesses the mutation. In some embodiments, the mutation is a copy number variant. Some embodiments further comprise estimating the number of copies in the copy number variant. In some embodiments, the sequencing data is DNA sequencing data. In some embodiments, the sequencing data is RNA sequencing data. In some embodiments, the sequencing data is genomic sequencing data. Some embodiments further comprise outputting a result of the aligning. Some embodiments further comprise providing a therapeutic intervention to a subject based on a result of analyzing the sequencing data.

In some embodiments, the invention provides a method of distinguishing a first haplotype and a second haplotype in a pair of haplotypes based on sequencing data, the method comprising: a) receiving by a computer system a first set of sequencing reads, wherein the computer system comprises a processor; b) determining by the processor that each sequencing read in the first set of sequencing reads possesses a common nucleic acid residue at a common position; and c) associating each sequencing read in the first set of sequencing reads with the first haplotype based on the possession of the common nucleic acid residue at the common position. In some embodiments, the common nucleic acid residue at the common position is a single nucleotide polymorphism. In some embodiments, the single nucleotide polymorphism is identified based on a comparison of the common nucleic acid residue at the common position with a corresponding position in a reference sequence. Some embodiments further comprise estimating a likelihood that one of the haplotypes possesses a mutation. In some embodiments, the mutation is a copy number variant. Some embodiments further comprise estimating the number of copies in the copy number variant. Some embodiments further comprise: d) receiving a second set of sequencing reads; e) determining that each sequencing read in the second set of sequencing reads possesses the common position and does not possess the common nucleic acid residue at the common position; and f) associating each sequencing read in the second set of sequencing reads with the second haplotype based on the non-possession of the common nucleic acid residue at the common position. In some embodiments, each sequencing read in the first set of sequencing reads comprises a common barcode. In some embodiments, each sequencing read in the second set of sequencing reads comprises the common barcode. Some embodiments further comprise: g) identifying a window of a reference sequence that corresponds to the sequencing reads in the first set of sequencing reads and the second set of sequencing reads; and h) comparing the total number of sequencing reads in the first set of sequencing reads that occur within the window and the total number of sequencing reads in the second set of sequencing reads that occur within the window. In some embodiments, the associating each sequencing read in the first set of sequencing reads with the first haplotype has an error rate of no greater than 1%. In some embodiments, the sequencing data is DNA sequencing data. In some embodiments, the sequencing data is RNA sequencing data. In some embodiments, the sequencing data is genomic sequencing data. Some embodiments further comprise outputting a result of the associating. Some embodiments further comprise providing a therapeutic intervention to a subject based on a result of the method.

In some embodiments, the invention provides a method of analyzing sequencing data associated with a sample, the method comprising: a) receiving by a computer system a first sequencing read, wherein the computer system comprises a processor; b) determining by the processor that the first sequencing read has a single polynucleotide polymorphism at a position; c) receiving a second sequencing read, wherein the second sequencing read comprises the position; d) determining that the second sequencing read has the single polynucleotide polymorphism at the position; and e) selecting the first sequencing read and the second sequencing read for alignment based on the presence of the single polynucleotide polymorphism at the position in both the first sequencing read and the second sequencing read. Some embodiments further comprise generating a candidate sequence by aligning the first sequencing read and the second sequencing read. In some embodiments, the presence of the single nucleotide polymorphism in the first sequencing read is determined by comparison of the first sequencing read with another sequence. In some embodiments, the presence of the single nucleotide polymorphism in the first sequencing read is determined by comparison of the first sequencing read with a reference sequence. In some embodiments, the sample is associated with a plurality of distinct barcodes. In some embodiments, the first sequencing read and the second sequencing read share a common barcode. Some embodiments further comprise receiving a third sequencing read, wherein the third sequencing read does not comprise the common barcode, and filtering out the third sequencing read. Some embodiments further comprise: f) receiving a third sequencing read, wherein the third sequencing read comprises the position; g) determining that the third sequencing read does not have the single polynucleotide polymorphism at the position; and h) excluding the third sequencing read from alignment with the first sequencing read based on the absence of the single polynucleotide polymorphism at the position of the third sequencing read. Some embodiments further comprise estimating a likelihood that the third sequencing read and the first sequencing read correspond to regions of a common chromosome. In some embodiments, the determining whether the third sequencing read and the first sequencing read correspond to regions of a common chromosome has an error rate of no greater than 1%. Some embodiments further comprise determining that the first sequencing read corresponds to a first haploid in a haploid pair, and that the third sequencing read corresponds to the second haploid in the haploid pair. In some embodiments, the determination that the first sequencing read corresponds to the first haploid in the haploid pair and that the third sequencing read corresponds to the second haploid in the haploid pair comprises determining a level of homology between the first sequencing read and the third sequencing read. In some embodiments, the sequencing data is DNA sequencing data. In some embodiments, the sequencing data is RNA sequencing data. In some embodiments, the sequencing data is genomic sequencing data. Some embodiments further comprise outputting the selection of the first sequencing read and the second sequencing read for alignment. Some embodiments further comprise providing a therapeutic intervention to a subject based on a result of the method.

In some embodiments, the invention provides a method of analyzing sequencing data associated with a sample, the method comprising: a) receiving by a computer system a first candidate sequence and a second candidate sequence, wherein the computer system comprises a processor; b) determining by the processor a pattern of single nucleotide polymorphisms or lack thereof within the first candidate sequence; c) determining a pattern of single nucleotide polymorphisms or lack thereof within the second candidate sequence; and d) estimating a likelihood that the first candidate sequence and the second candidate sequence correspond to a common chromosome based on the pattern of single nucleotide polymorphisms or lack thereof within the first candidate sequence and the pattern of single nucleotide polymorphisms or lack thereof within the second candidate sequence. In some embodiments, the estimation of the likelihood that the first candidate sequence and the second candidate sequence correspond to a common chromosome is based on a statistical analysis of the pattern of single nucleotide polymorphisms or lack thereof within the first candidate sequence and the pattern of single nucleotide polymorphisms or lack thereof within the second candidate sequence. In some embodiments, the estimating the likelihood that the first candidate sequence and the second candidate sequence correspond to a common chromosome has an error rate of no greater than 1%. In some embodiments, the sequencing data is DNA sequencing data. In some embodiments, the sequencing data is RNA sequencing data. In some embodiments, the sequencing data is genomic sequencing data. Some embodiments further comprise outputting the selection of the first sequencing read and the second sequencing read for alignment. Some embodiments further comprise providing a therapeutic intervention to a subject based on a result of the method.

In some embodiments, the invention provides a method of analyzing sequencing data associated with a sample, the method comprising: a) receiving by a computer system a set of sequencing reads, wherein all of the sequencing reads comprise a common position, wherein the computer system comprises a processor; b) determining by the processor that all of the sequencing reads in the set of sequencing reads correspond to a common haplotype; c) checking an identity of a nucleic acid residue at the common position in each sequencing read in the set of sequencing reads; and e) estimating a likelihood that an error exists in at least one of the sequencing reads based on the checking. Some embodiments further comprise determining that each sequencing read shares a common nucleic acid residue at the common position. In some embodiments, the common nucleic acid residue at the common position is a single nucleotide polymorphism. Some embodiments further comprise determining that the identity of the nucleic acid residue at the common position in one of the sequencing reads is different from the identity of the nucleic acid residue at the common position in another one of the sequencing reads. In some embodiments, all of the sequencing reads in the set of sequencing reads share a common barcode. In some embodiments, the sample is associated with a plurality of distinct barcodes. Some embodiments further comprise receiving an additional sequencing read, wherein the additional sequencing read does not correspond to the common haplotype, and excluding the additional sequencing read from the set of sequencing reads. Some embodiments further comprise determining that the additional sequencing read corresponds to a second haplotype complementary to the common haplotype. In some embodiments, the sequencing data is DNA sequencing data. In some embodiments, the sequencing data is RNA sequencing data. In some embodiments, the sequencing data is genomic sequencing data. Some embodiments further comprise outputting the estimated likelihood that an error exists in at least one of the sequencing reads.

In some embodiments, the invention provides a method of analyzing sequencing data associated with a sample, the method comprising: a) receiving by a computer system a first sequencing read and a second sequencing read, wherein the first sequencing read and the second sequencing read each comprise a common barcode, wherein the computer system comprises a processor; b) aligning the first sequencing read to a reference genome, wherein the reference genome comprises at least two reference chromosomes, and determining that the first sequencing read corresponds to a first reference chromosome in the reference genome; and c) aligning the second sequencing read to the reference genome and determining to which reference chromosome in the reference genome the second sequencing read corresponds, wherein the sample is associated with a plurality of distinct barcodes. In some embodiments, the aligning the second sequencing read to the reference genome determines that the second sequencing read corresponds to the first reference chromosome in the reference genome. In some embodiments, the aligning the second sequencing read to the reference genome determines that the second sequencing read corresponds to a second reference chromosome in the reference genome. Some embodiments further comprise estimating a likelihood that the sample contains a mutation from the reference genome. In some embodiments, the estimating the likelihood that the sample contains the mutation from the reference genome is based on the alignment of the first sequencing read to the reference genome and the alignment of the second sequencing read to the reference genome. Some embodiments further comprise determining a candidate site of the mutation in the reference genome. In some embodiments, the mutation is a translocation. Some embodiments further comprise: d) receiving by the computer system a plurality of further sequencing reads, wherein each further sequencing read comprises the common barcode; e) aligning each further sequencing read against the first reference chromosome in the reference genome; f) identifying a portion of the first reference chromosome that does not align to any of the further sequencing reads; and g) identifying the portion of the first reference chromosome that does not align to any of the further sequencing reads as the candidate breakpoint. Some embodiments further comprise determining a candidate breakpoint in the reference genome. In some embodiments, the candidate breakpoint is within 100 nucleotide residues of a sequencing read that aligns with the first reference chromosome. In some embodiments, the candidate breakpoint is within 50 nucleotide residues of a sequencing read that aligns with the first reference chromosome. In some embodiments, the candidate breakpoint is within 10 nucleotide residues of a sequencing read that aligns with the first reference chromosome. Some embodiments further comprise determining which haplotype in a pair of haplotypes possesses the mutation. In some embodiments, the determining which haplotype in the pair of haplotypes possesses the mutation comprises identifying a common position among a subset of the further sequencing reads and identifying a common single nucleotide polymorphism at the common position of the further sequencing reads. In some embodiments, the sequencing data is DNA sequencing data. In some embodiments, the sequencing data is RNA sequencing data. In some embodiments, the sequencing data is genomic sequencing data. Some embodiments further comprise outputting the determination of the reference chromosome in the reference genome to which the second sequencing read corresponds. Some embodiments further comprise providing a therapeutic intervention to a subject based on a result of the method.

In some embodiments, the invention provides a method of analyzing sequencing data associated with a sample, the method comprising: a) receiving by a computer system a set of sequencing reads, wherein each sequencing read independently comprises a barcode, wherein the computer system comprises a processor; b) sorting by the processor the sequencing reads of the set of sequencing reads into subsets, wherein each sequencing read of a first subset comprises a first common barcode, and each sequencing read of a second subset comprises a second common barcode, wherein the first common barcode and the second common barcode are not identical; and c) comparing the sequencing reads of the first subset to determine whether any sequencing reads of the first subset share a common subsequence in addition to the first barcode, wherein the sample is associated with a plurality of distinct barcodes. Some embodiments further comprise mutually aligning the sequencing reads of the first subset. Some embodiments further comprise excluding the sequencing reads of the second subset from the alignment. Some embodiments further comprise determining a candidate sequence based on the sequencing reads of the first subset. Some embodiments further comprise comparing the candidate sequence to a reference sequence. Some embodiments further comprise incorporating at least one of the sequencing reads of the second subset into the candidate sequence. Some embodiments further comprise determining a pattern of the first common barcode and the second common barcode based on the candidate sequence. Some embodiments further comprise scoring the candidate sequence based on the pattern of the first common barcode and the second common barcode. In some embodiments, the sequencing data is DNA sequencing data. In some embodiments, the sequencing data is RNA sequencing data. In some embodiments, the sequencing data is genomic sequencing data. Some embodiments further comprise outputting a result of the comparing. Some embodiments further comprise providing a therapeutic intervention to a subject based on a result of analyzing the sequencing data.

In some embodiments, the invention provides a method of identifying sequencing errors in sequencing data associated with a sample, the method comprising: a) receiving by a computer system a first sequencing read and a second sequencing read, wherein the first sequencing read and the second sequencing read comprise a common barcode, wherein the first sequencing read and the second sequencing read share at least 90% homology, and wherein the computer system comprises a processor; b) comparing by the processor the first sequencing read and the second sequencing read to find at least one site at which the first sequencing read and the second sequencing read differ; and c) determining that the site in the second sequencing read is an error based on the comparing, wherein the sample is associated with a plurality of distinct barcodes. Some embodiments further comprise comparing the second sequencing read with a number of additional sequencing reads, wherein each of the additional sequencing reads comprises the common barcode and shares at least 90% homology with the second sequencing read. In some embodiments, a confidence level of the determining that the site in the second sequencing read is an error increases as the number of additional sequencing reads compared to the second sequencing read increases. Some embodiments further comprise fixing the error by changing a nucleic acid identity at the site in the second sequencing read. In some embodiments, the first sequencing read is longer than the second sequencing read. In some embodiments, the first sequencing read and the second sequencing read share at least 95% homology. In some embodiments, the first sequencing read and the second sequencing read share at least 99% homology. In some embodiments, the first sequencing read and the second sequencing read share at least 99.9% homology. In some embodiments, the sequencing data is DNA sequencing data. In some embodiments, the sequencing data is RNA sequencing data. In some embodiments, the sequencing data is genomic sequencing data. Some embodiments further comprise outputting that the site in the second sequencing read is an error.

In some embodiments, the invention provides a method of analyzing sequencing data, the method comprising: a) receiving by a computer system a candidate sequence, wherein the candidate sequence is based on a set of sequencing reads, wherein each sequencing read is independently associated with one of at least two distinct barcodes, wherein the computer system comprises a processor; and b) analyzing by the processor the candidate sequence to identify a pattern of the barcodes associated with the candidate sequence. Some embodiments further comprise: c) selecting a sequencing read from the set of sequencing reads; and d) comparing the pattern of the barcodes associated with the candidate sequence and the barcode associated with the selected sequencing read. Some embodiments further comprise: e) relocating the selected sequencing based on the comparison of the pattern of the barcodes associated with the candidate sequence and the barcode associated with the selected sequencing read. In some embodiments, the candidate sequence corresponds to a reference chromosome, and the method further comprises relocating one of the sequencing reads to another position on the reference chromosome. In some embodiments, the candidate sequence corresponds to a reference chromosome, and the method further comprises relocating one of the sequencing reads to another reference chromosome. In some embodiments, the sequencing data is DNA sequencing data. In some embodiments, the sequencing data is RNA sequencing data. In some embodiments, the sequencing data is genomic sequencing data. Some embodiments further comprise providing an output based on the analyzing.

In some embodiments, the invention provides a method of analyzing sequencing data, the method comprising: a) receiving by a computer system a first candidate sequence and a second candidate sequence, wherein the computer system comprises a processor; b) processing by the processor the first candidate sequence and the second candidate sequence to provide display data for both first candidate sequence and the second candidate sequence; and c) displaying contemporaneously the first candidate sequence and the second candidate sequence. In some embodiments, the first candidate sequence is based on data obtained from a sequencing instrument. In some embodiments, the first candidate sequence is received before the sequencing assay is complete. In some embodiments, the display of the first candidate sequence is updated before the sequencing assay is complete. In some embodiments, the display of the second candidate sequence is updated contemporaneously with the update of the display of the first candidate sequence. In some embodiments, the second candidate sequence is based on data obtained from the sequencing instrument. In some embodiments, the second candidate sequence is based on data obtained from a different sequencing instrument. In some embodiments, the second candidate sequence is based on data obtained from a database. In some embodiments, the first candidate sequence and the second candidate sequence correspond to different chromosomes. In some embodiments, the different chromosomes are associated with a common sample. In some embodiments, the different chromosomes are each independently associated with a different sample. In some embodiments, the sequencing data is DNA sequencing data. In some embodiments, the sequencing data is RNA sequencing data. In some embodiments, the sequencing data is genomic sequencing data. In some embodiments, the sequencing data is peptide sequencing data.

In some embodiments, the invention provides a computer program product comprising a computer-readable medium having computer-executable code encoded therein, the computer-executable code adapted to be executed to implement a method of analyzing sequencing data, the method comprising: a) providing a sequencing data analysis system, wherein the sequencing data analysis system comprises: i) a receiving module configured to receive sequencing data associated with a sequencing assay while the sequencing assay is in progress; and ii) an alignment module configured to align sequencing data while the sequencing assay is in progress; b) receiving by the receiving module a set of sequencing reads associated with the sequencing assay while the sequencing assay is in progress; and c) performing an alignment by the alignment module of at least one received sequencing read with another sequence while the sequencing assay is in progress. In some embodiments, the sequencing data analysis system further comprises a database access module, wherein the method further comprises accessing a database to obtain the other sequence. In some embodiments, the sequencing data analysis system further comprises a reference sequence, wherein the other sequence aligned with the sequencing read is the reference sequence. In some embodiments, the sequencing data analysis system further comprises a barcode module, wherein the method further comprises identifying by the barcode module at least two sequencing reads in the set of sequencing reads that share a common barcode. In some embodiments, the sequencing data analysis system further comprises a candidate module, wherein the method further comprises building by the candidate module a candidate sequence based on the alignment. In some embodiments, the sequencing data analysis system further comprises a mutation module, wherein the method further comprises estimating by the mutation module a likelihood that the candidate sequence comprises a mutation. In some embodiments, the mutation is a single nucleotide polymorphism. In some embodiments, the mutation is a copy number variant. In some embodiments, the mutation is a translocation. In some embodiments, the sequencing data analysis system further comprises a haplotype module, wherein the method further comprises determining by the haplotype module to which haplotype in a pair of haplotypes one of sequencing reads of the set of sequencing reads corresponds. In some embodiments, the sequencing reads associated with the sequencing assay are received from an instrument conducting the sequencing assay. In some embodiments, the sequencing reads associated with the sequencing assay are received from a database. In some embodiments, the computer program product is in communication with a sequencing instrument. In some embodiments, the sequencing data analysis system further comprises a user information module, wherein the method further comprises obtaining by the user information module user information from the sequencing instrument. In some embodiments, the sequencing data analysis system further comprises a user information module, wherein the method further comprises obtaining by the user information module user information associated with a configuration of the sequencing instrument. In some embodiments, the computer program product is in communication with a plurality of sequencing instruments. In some embodiments, the sequencing data analysis system analyzes DNA sequencing data. In some embodiments, the sequencing data analysis system analyzes RNA sequencing data. In some embodiments, the sequencing data analysis system analyzes genomic sequencing data. In some embodiments, the sequencing data analysis system analyzes peptide sequencing data. In some embodiments, the sequencing data analysis system further comprises an output module, wherein the method further comprises outputting by the output module a result of the alignment.

In some embodiments, the invention provides a computer program product comprising a computer-readable medium having computer-executable code encoded therein, the computer-executable code adapted to be executed to implement a method of analyzing sequencing data, the method comprising: a) providing a sequencing data analysis system, wherein the sequencing data analysis system comprises: i) a receiving module; ii) an alignment module; iii) a database access module; iv) a window module; and v) a barcode module; b) receiving by the receiving module a set of sequencing reads, wherein each sequencing read independently comprises a barcode; c) accessing by the database access module a database to obtain a reference sequence stored in the database; d) performing an alignment by the alignment module of each sequencing read of the set of sequencing reads with the reference sequence; e) selecting by the window module a window of the reference sequence; and f) counting by the barcode module a total number of distinct barcodes associated with the reference sequence within the window of the reference sequence based on the alignment. In some embodiments, the sequencing data analysis system further comprises a mutation module, wherein the method further comprises estimating by the mutation module a likelihood that a sample associated with the set of sequencing reads comprises a mutation based on the counting. In some embodiments, the sequencing data analysis system further comprises a haplotype module, wherein the method further comprises determining by the haplotype module which haplotype in a pair of haplotypes comprises the mutation. In some embodiments, the mutation is a copy number variant. In some embodiments, the method further comprises estimating by the mutation module the number of copies in the copy number variant. In some embodiments, the sequencing data analysis system analyzes DNA sequencing data. In some embodiments, the sequencing data analysis system analyzes RNA sequencing data. In some embodiments, the sequencing data analysis system analyzes genomic sequencing data. In some embodiments, the sequencing data analysis system further comprises an output module, wherein the method further comprises outputting by the output module a result of the counting.

In some embodiments, the invention provides a computer program product comprising a computer-readable medium having computer-executable code encoded therein, the computer-executable code adapted to be executed to implement a method of analyzing sequencing data, the method comprising: a) providing a sequencing data analysis system, wherein the sequencing data analysis system comprises: i) a receiving module; ii) an alignment module; iii) a database access module; and iv) a sorting module; b) receiving by the receiving module a set of sequencing reads, wherein each sequencing read shares a common position; c) accessing by the database access module a database to obtain a reference sequence stored in the database; d) performing an alignment by the alignment module of each sequencing read of the set of sequencing reads with the reference sequence; and e) sorting by the sorting module the sequencing reads of the set of sequencing reads into two subsets of sequencing reads, wherein a first subset of sequencing reads contains sequencing reads that match the reference sequence at the common position, and a second subset of sequencing reads contains sequencing reads that do not match the reference sequence at the common position. In some embodiments, each sequencing read of the second subset of sequencing reads possesses a single nucleotide polymorphism at the common position. In some embodiments, the sequencing data analysis system further comprises a haplotype module, wherein the method further comprises associating by the haplotype module the first subset of sequencing reads with a first haplotype of a pair of haplotypes, and the second subset of sequencing reads with the second haplotype of the pair of haplotypes. In some embodiments, the sequencing data analysis system further comprises a mutation module, wherein the method further comprises estimating by the mutation module a likelihood that either haplotype of the pair of haplotypes comprises a mutation based on a total number of sequencing reads in the first subset of sequencing reads and a total number of sequencing reads in the second subset of sequencing reads. In some embodiments, the sequencing data analysis system further comprises a barcode module, wherein the method further comprises identifying a common barcode within the a set of sequencing reads and excluding from the first subset of sequencing reads and the second subset of sequencing reads any sequencing read that does not comprise the common barcode. In some embodiments, the sequencing data analysis system analyzes DNA sequencing data. In some embodiments, the sequencing data analysis system analyzes RNA sequencing data. In some embodiments, the sequencing data analysis system analyzes genomic sequencing data. In some embodiments, the sequencing data analysis system further comprises an output module, wherein the method further comprises outputting by the output module a result of the sorting.

In some embodiments, the invention provides a computer program product comprising a computer-readable medium having computer-executable code encoded therein, the computer-executable code adapted to be executed to implement a method of analyzing sequencing data, the method comprising: a) providing a sequencing data analysis system, wherein the sequencing data analysis system comprises: i) a receiving module; ii) an alignment module; iii) a database access module; and iv) a selection module; b) receiving by the receiving module a first sequencing read and a second sequencing read, wherein the first sequencing read and the second sequencing read overlap at a common position; c) accessing by the database access module a database to obtain a reference sequence stored in the database; d) performing an alignment by the alignment module of the first sequencing read with the reference sequence, thereby determining a presence of a single nucleotide polymorphism at the common position in the first sequencing read; e) performing an alignment by the alignment module of the second sequencing read with the reference sequence, thereby determining a presence of the single nucleotide polymorphism at the common position in the second sequencing read; and f) selecting by the selection module the first sequencing read and the second sequencing read for mutual alignment based on the presence of the single nucleotide polymorphism at the common position in the first sequencing read and the second sequencing read. In some embodiments, the method further comprises aligning by the alignment module the first sequencing read and the second sequencing read. In some embodiments, the sequencing data analysis system further comprises a candidate module, wherein the method further comprises building by the candidate module a candidate sequence based on the alignment of the first sequencing read and the second sequencing read. In some embodiments, the sequencing data analysis system further comprises a barcode module, wherein the method further comprises determining by the barcode module that the first sequencing read and the second sequencing read share a common barcode. In some embodiments, the selecting by the selection module the first sequencing read and the second sequencing read for mutual alignment is further based on the first sequencing read and the second sequencing read sharing a common barcode. In some embodiments, the sequencing data analysis system further comprises a chromosome module, wherein the receiving module receives a third sequencing read, and wherein the method further comprises estimating by the chromosome module a likelihood that the third sequencing read and the first sequencing read correspond to regions of a common chromosome. In some embodiments, the sequencing data analysis system analyzes DNA sequencing data. In some embodiments, the sequencing data analysis system analyzes RNA sequencing data. In some embodiments, the sequencing data analysis system analyzes genomic sequencing data. In some embodiments, the sequencing data analysis system further comprises an output module, wherein the method further comprises outputting by the output module a result based on the selecting the first sequencing read and the second sequencing read for alignment.

In some embodiments, the invention provides a computer program product comprising a computer-readable medium having computer-executable code encoded therein, the computer-executable code adapted to be executed to implement a method of analyzing sequencing data, the method comprising: a) providing a sequencing data analysis system, wherein the sequencing data analysis system comprises: i) a receiving module; ii) a pattern module; and iii) a chromosome module; b) receiving by the receiving module a first candidate sequence and a second candidate sequence; c) determining by the pattern module a pattern of single nucleotide polymorphisms or lack thereof within the first candidate sequence; d) determining by the pattern module a pattern of single nucleotide polymorphisms or lack thereof within the second candidate sequence; and e) estimating by the chromosome module a likelihood that the first candidate sequence and the second candidate sequence correspond to a common chromosome based on the pattern of single nucleotide polymorphisms or lack thereof within the first candidate sequence and the pattern of single nucleotide polymorphisms or lack thereof within the second candidate sequence. In some embodiments, the sequencing data analysis system further comprises a statistical database access module, wherein the statistical database comprises statistical information associated with single nucleotide polymorphisms, wherein the estimating by the chromosome module the likelihood that the first candidate sequence and the second candidate sequence correspond to the common chromosome comprises comparing, by the chromosome module, the pattern of single nucleotide polymorphisms or lack thereof within the first candidate sequence and the pattern of single nucleotide polymorphisms or lack thereof within the second candidate sequence to information in the statistical database via the statistical database access module. In some embodiments, the sequencing data analysis system analyzes DNA sequencing data. In some embodiments, the sequencing data analysis system analyzes RNA sequencing data. In some embodiments, the sequencing data analysis system analyzes genomic sequencing data. In some embodiments, the sequencing data analysis system further comprises an output module, wherein the method further comprises outputting by the output module an estimated likelihood that the first candidate sequence and the second candidate sequence correspond to a common chromosome.

In some embodiments, the invention provides a computer program product comprising a computer-readable medium having computer-executable code encoded therein, the computer-executable code adapted to be executed to implement a method of analyzing sequencing data, the method comprising: a) providing a sequencing data analysis system, wherein the sequencing data analysis system comprises: i) a receiving module; ii) a haplotype module; iii) a nucleotide-recognition module; and iv) an error module; b) receiving by the receiving module a set of sequencing reads, wherein all of the sequencing reads comprise a common position; c) determining by the haplotype module that all of the sequencing reads in the set of sequencing reads correspond to a common halpotype; d) recognizing by the nucleotide-recognition module a nucleic acid residue at the common position in each of the sequencing reads in the set of sequencing reads independently; and e) estimating by the error module a likelihood that an error exists in at least one of the sequencing reads in the set of sequencing reads based on the identifying. In some embodiments, the sequencing data analysis system further comprises a reference sequence and an alignment module, wherein the method further comprises determining by the alignment module that at least one sequencing read in the set of sequencing reads has a single nucleotide polymorphism at the common position based on an alignment of the sequencing read with the reference sequence. In some embodiments, the sequencing data analysis system further comprises a barcode module, wherein the method further comprises determining by the barcode module that the sequencings reads in the set of sequencing reads share a common barcode. In some embodiments, the sequencing data is DNA sequencing data. In some embodiments, the sequencing data is RNA sequencing data. In some embodiments, the sequencing data is genomic sequencing data. In some embodiments, the sequencing data analysis system further comprises a correction module, wherein the method further comprises correcting the error by the correction module. In some embodiments, the correcting the error by the correction module comprises replacing a nucleic acid residue in one of the sequencing reads with an alternative nucleic acid residue. In some embodiments, the sequencing data analysis system further comprises an output module, wherein the method further comprises outputting by the output module an estimated likelihood that an error exists in at least one of the sequencing reads.

In some embodiments, the invention provides a computer program product comprising a computer-readable medium having computer-executable code encoded therein, the computer-executable code adapted to be executed to implement a method of analyzing sequencing data, the method comprising: a) providing a sequencing data analysis system, wherein the sequencing data analysis system comprises: i) a receiving module; ii) an alignment module; iii) a database access module; and iv) a mutation module; b) receiving by the receiving module a first sequencing read and a second sequencing read; c) accessing by the database access module a database to obtain a reference genome stored in the database, wherein the reference genome comprises at least two reference chromosomes; d) performing an alignment by the alignment module of the first sequencing read with the reference genome, thereby determining that the first sequencing read corresponds to a first reference chromosome in the reference genome; e) performing an alignment by the alignment module of the second sequencing read with the reference genome, thereby determining that the second sequencing read corresponds to a second reference chromosome in the reference genome; and f) estimating by the mutation module a likelihood that a mutation exists in a sample associated with the first sequencing read and the second sequencing read based on the alignments of the first sequencing read and the second sequencing read with the reference genome. In some embodiments, the method further comprises determining by the mutation module a candidate site of the mutation based on the alignments of the first sequencing read and the second sequencing read with the reference genome. In some embodiments, the mutation module is configured to identify a translocation, and wherein the estimating by the mutation module a likelihood that a mutation exists in the sample associated with the first sequencing read and the second sequencing read comprises estimating a likelihood that a translocation exists in the sample associated with the first sequencing read and the second sequencing read. In some embodiments, the mutation module is configured to identify a candidate breakpoint associated with the translocation, wherein the method further comprises identifying by the mutation module a candidate breakpoint associated with the translocation based on the alignments of the first sequencing read and the second sequencing read with the reference genome. In some embodiments, the sequencing data analysis system further comprises a barcode module, and the method further comprises: g) receiving by the receiving module a plurality of further sequencing reads; h) determining by the barcode module that the first sequencing read and the further sequencing reads comprise a common barcode; i) aligning by the alignment module each further sequencing read against the first reference chromosome in the reference genome; and j) identifying by the alignment module a portion of the first reference chromosome that does not align to any of the further sequencing reads. In some embodiments, the sequencing data analysis system further comprises a haplotype module, wherein the method further comprises determining by the haplotype module which haplotype in a pair of haplotypes has the mutation. In some embodiments, the sequencing data is DNA sequencing data. In some embodiments, the sequencing data is RNA sequencing data. In some embodiments, the sequencing data is genomic sequencing data. In some embodiments, the sequencing data analysis system further comprises an output module, wherein the method further comprises outputting by the output module an estimated likelihood that that the mutation exists in the sample associated with the first sequencing read and the second sequencing.

In some embodiments, the invention provides a computer program product comprising a computer-readable medium having computer-executable code encoded therein, the computer-executable code adapted to be executed to implement a method of analyzing sequencing data, the method comprising: a) providing a sequencing data analysis system, wherein the sequencing data analysis system comprises: i) a receiving module; ii) a barcode module; and iii) an alignment module; b) receiving by the receiving module a first set of sequencing reads and a second set of sequencing reads; c) determining by the barcode module that the sequencing reads of the first set of sequencing reads share a first common barcode; d) determining by the barcode module that the sequencing reads of the second set of sequencing reads share a second common barcode, wherein the first common barcode and the second common barcode are not identical; and e) performing an alignment by the alignment module of one sequencing read of the first set of sequencing reads with one sequencing read of the second set of sequencing reads. In some embodiments, the sequencing data analysis system further comprises a candidate module, wherein the method further comprises determining a candidate sequence by the candidate module based on the alignment of one sequencing read of the first set of sequencing reads with one sequencing read of the second set of sequencing reads. In some embodiments, the sequencing data analysis system further comprises a pattern module, wherein the method further comprises determining a pattern by the pattern module of the first common barcode and the second common barcode based on the candidate sequence. In some embodiments, the sequencing data analysis system further comprises a scoring module, wherein the method further comprises scoring by the scoring module the candidate sequence based on the pattern of the first common barcode and the second common barcode. In some embodiments, the sequencing data is DNA sequencing data. In some embodiments, the sequencing data is RNA sequencing data. In some embodiments, the sequencing data is genomic sequencing data. In some embodiments, the sequencing data analysis system further comprises an output module, wherein the method further comprises outputting by the output module the alignment of one sequencing read of the first set of sequencing reads with one sequencing read of the second set of sequencing reads.

In some embodiments, the invention provides a computer program product comprising a computer-readable medium having computer-executable code encoded therein, the computer-executable code adapted to be executed to implement a method of analyzing sequencing data, the method comprising: a) providing a sequencing data analysis system, wherein the sequencing data analysis system comprises: i) a receiving module; ii) a barcode module; and iii) a pattern module; b) receiving by the receiving module a candidate sequence; c) determining by the barcode module that the candidate sequence is associated with a plurality of distinct barcodes; and d) determining by the pattern module a pattern of the barcodes associated with the sequencing reads. In some embodiments, the candidate sequence is based on a set of sequencing reads, wherein the method further comprises determining by the barcode module which barcode of the plurality of distinct barcodes is independently associated with each sequencing read in the set of sequencing reads. In some embodiments, the sequencing data analysis system further comprises a selection module, wherein the method further comprises selecting by the selection module one of the sequencing reads, and comparing by the pattern module the pattern of barcodes associated with the candidate sequence and the barcode associated with the selected sequencing read. In some embodiments, the sequencing data analysis system further comprises a relocation module, wherein the method further comprises relocating by the relocation module the selected sequencing read based on the comparison of the pattern of barcodes associated with the candidate sequence and the barcode associated with the selected sequencing read. In some embodiments, the candidate sequence corresponds to a candidate chromosome, and the selected sequencing read is relocated to another position on the candidate chromosome. In some embodiments, the candidate sequence corresponds to a candidate chromosome, and the selected sequencing read is relocated to another candidate chromosome. In some embodiments, the sequencing data is DNA sequencing data. In some embodiments, the sequencing data is RNA sequencing data. In some embodiments, the sequencing data is genomic sequencing data. In some embodiments, the sequencing data analysis system further comprises an output module, wherein the method further comprises outputting by the output module an output based on the pattern of the barcodes associated with the sequencing reads.

In some embodiments, the invention provides a computer program product comprising a computer-readable medium having computer-executable code encoded therein, the computer-executable code adapted to be executed to implement a method of analyzing sequencing data, the method comprising: a) providing a sequencing data analysis system, wherein the sequencing data analysis system comprises: i) a receiving module; ii) a first display module; and iii) a second display module; b) receiving by the receiving module a first candidate sequence and a second candidate sequence; c) displaying by the first display module the first candidate sequence; and d) displaying by the second display module the second candidate sequence contemporaneously with the displaying by the first display module of the first candidate sequence. In some embodiments, the first candidate sequence is received before a sequencing assay that generated the first candidate sequence is complete. In some embodiments, the sequencing data analysis system further comprises an update module, wherein the method further comprises updating by the update module the display of the first candidate sequence before a sequencing assay that generated the first candidate sequence is complete. In some embodiments, the method further comprises updating by the update module the display of the second candidate sequence contemporaneously with the update of the display of the first candidate sequence. In some embodiments, the sequencing data analysis system is in communication with a sequencing instrument, wherein the first candidate sequence is based on sequencing data received from the sequencing instrument. In some embodiments, the second candidate sequence is based on sequencing data received from the sequencing instrument by the receiving module. In some embodiments, the second candidate sequence is based on sequencing data received from a different sequencing instrument by the receiving module. In some embodiments, the second candidate sequence is received from a database by the receiving module. In some embodiments, the sequencing data is DNA sequencing data. In some embodiments, the sequencing data is RNA sequencing data. In some embodiments, the sequencing data is genomic sequencing data. In some embodiments, the sequencing data is peptide sequencing data.

What is claimed is:

1. A method comprising:
   (a) sequencing a plurality of biomolecules and generating a plurality of partial sequence data from the plurality of biomolecules using a sequencer in communication with a remote server;
   (b) while the sequencer is sequencing the plurality of biomolecules, receiving, at the remote server, the plurality of partial sequence data, wherein the plurality of partial sequence data is streamed from the sequencer over a network to the remote server; and
   (c) while the sequencer is sequencing the plurality of biomolecules, processing the plurality of partial sequence data at the remote server.

2. The method of claim 1, wherein the plurality of partial sequence data is generated by sequencing-by-synthesis.

3. The method of claim 1, wherein the processing the plurality of partial sequence data is performed in real time.

4. The method of claim 1, wherein the processing the plurality of partial sequence data is performed using parallel processing.

5. The method of claim 1, wherein the plurality of partial sequence data comprises a first partial sequencing read having a first barcode sequence, wherein the processing the plurality of partial sequence data comprises aligning the first partial sequencing read to a reference biomolecule.

6. The method of claim 1, further comprising determining a statistical parameter for the plurality of partial sequence data.

7. The method of claim 6, wherein the statistical parameter is a probability of a sequencing error.

8. The method of claim 1, wherein the plurality of partial sequence data comprises sequence alignment data.

9. The method of claim 1, wherein the plurality of partial sequence data comprises gene expression data.

10. The method of claim 1, wherein the plurality of partial sequence data comprises genome annotation data.

11. The method of claim 1, wherein the plurality of partial sequence data comprises genomic data from one or more cycles of the sequencer.

12. The method of claim 11, wherein the processing the plurality of partial sequence data is performed during the one or more cycles of the sequencer.

13. The method of claim 1, wherein the plurality of partial sequence data is stored in a local database.

14. The method of claim 1, wherein the plurality of partial sequence data is stored in a distributed database.

15. The method of claim 1, further comprising obtaining the plurality of biomolecules from a biological sample of a subject.

16. The method of claim 1, wherein the plurality of biomolecules comprises nucleic acid molecules.

17. The method of claim 1, wherein the plurality of biomolecules comprises one or more proteins.

18. The method of claim 1, wherein the plurality of biomolecules are from a sample, wherein the sample comprises a tissue sample.

19. A computer program product comprising a computer readable storage medium having program instructions embodied therewith, the program instructions executable by a processor of a remote server in communication with a sequencer configured to sequence a plurality of biomolecules and generate a plurality of partial sequence data from the plurality of biomolecules, wherein the program instructions are configured to cause the processor to perform a method comprising:
- (a) while the sequencer is sequencing the plurality of biomolecules, receiving the plurality of partial sequence data, wherein the plurality of partial sequence data is streamed from the sequencer over a network to the processor of the remote server; and
- (b) while the sequencer is sequencing the plurality of biomolecules, processing the plurality of partial sequence data.

20. A system comprising
a genomic data database; and
a computing node comprising a computer readable storage medium having program instructions embodied therewith, the program instructions executable by at least one processor of a remote server in communication with a sequencer configured to sequence a plurality of biomolecules and generate a plurality of partial sequence data from the plurality of biomolecules, wherein the program instructions are configured to cause the at least one processor to perform a method comprising:
- (a) while the sequencer is sequencing the plurality of biomolecules, receiving the plurality of partial sequence data, wherein the plurality of partial sequence data is streamed from the sequencer over a network to the at least one processor of the remote server and stored in the genomic data database; and
- (b) while the sequencer is sequencing the plurality of biomolecules, processing the plurality of partial sequence data.

* * * * *